(12) United States Patent
Edwards et al.

(10) Patent No.: US 12,227,576 B2
(45) Date of Patent: *Feb. 18, 2025

(54) METHODS OF TREATING A TUMOR USING AN ANTI-PD-1 ANTIBODY

(71) Applicant: Bristol-Myers Squibb Company, Princeton, NJ (US)

(72) Inventors: Robin Edwards, Newtown, PA (US); William J. Geese, Pipersville, PA (US); Danielle M. Greenawalt, Philadelphia, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/161,713

(22) Filed: Jan. 30, 2023

(65) Prior Publication Data

US 2023/0279114 A1 Sep. 7, 2023

Related U.S. Application Data

(63) Continuation of application No. 16/617,725, filed as application No. PCT/US2018/035670 on Jun. 1, 2018, now Pat. No. 11,566,073.

(60) Provisional application No. 62/513,831, filed on Jun. 1, 2017.

(51) Int. Cl.
*C07K 16/28* (2006.01)
*A61P 35/00* (2006.01)

(52) U.S. Cl.
CPC .......... *C07K 16/2818* (2013.01); *A61P 35/00* (2018.01)

(58) Field of Classification Search
CPC .............................. C07K 16/2818; A61P 35/00
See application file for complete search history.

(56) References Cited

U.S. PATENT DOCUMENTS

| | | |
|---|---|---|
| 6,808,710 B1 | 10/2004 | Wood et al. |
| 7,488,802 B2 | 2/2009 | Collins et al. |
| 7,943,743 B2 | 5/2011 | Korman et al. |
| 8,008,449 B2 | 8/2011 | Korman et al. |
| 8,168,757 B2 | 5/2012 | Finnefrock et al. |
| 8,217,149 B2 | 7/2012 | Irving et al. |
| 8,354,509 B2 | 1/2013 | Carven et al. |
| 8,779,105 B2 | 7/2014 | Korman et al. |
| 8,900,587 B2 | 12/2014 | Carven et al. |
| 9,084,776 B2 | 7/2015 | Korman et al. |
| 9,212,224 B2 | 12/2015 | Cogswell et al. |
| 9,358,289 B2 | 6/2016 | Korman et al. |
| 9,387,247 B2 | 7/2016 | Korman et al. |
| 9,492,539 B2 | 11/2016 | Korman et al. |
| 9,492,540 B2 | 11/2016 | Korman et al. |
| 9,580,507 B2 | 2/2017 | Korman et al. |
| 9,856,320 B2 | 1/2018 | Cogswell et al. |
| 10,072,082 B2 | 9/2018 | Cogswell et al. |
| 10,138,299 B2 | 11/2018 | Cogswell et al. |
| 10,266,594 B1 | 4/2019 | Cogswell et al. |
| 10,266,595 B2 | 4/2019 | Cogswell et al. |
| 10,266,596 B1 | 4/2019 | Cogswell et al. |
| 10,308,714 B2 | 6/2019 | Cogswell et al. |
| 10,316,090 B2 | 6/2019 | Cogswell et al. |
| 10,316,091 B2 | 6/2019 | Cogswell et al. |
| 10,323,092 B2 | 6/2019 | Cogswell et al. |
| 10,323,093 B2 | 6/2019 | Cogswell et al. |
| 10,441,655 B2 | 10/2019 | Korman et al. |
| 10,577,423 B2 | 3/2020 | Cogswell et al. |
| 10,584,170 B2 | 3/2020 | Cogswell et al. |
| 10,604,575 B2 | 3/2020 | Cogswell et al. |
| 2015/0079109 A1 | 3/2015 | Li et al. |
| 2016/0272708 A1 | 9/2016 | Chen |
| 2017/0130271 A1 | 5/2017 | Wong |
| 2020/0138945 A1 | 5/2020 | Korman et al. |
| 2020/0308282 A1 | 10/2020 | Cogswell et al. |
| 2020/0325226 A1 | 10/2020 | Edwards et al. |

FOREIGN PATENT DOCUMENTS

| | | |
|---|---|---|
| CN | 106062004 A | 10/2016 |
| CN | 113249483 A | 8/2021 |
| WO | WO-2008156712 A1 | 12/2008 |
| WO | WO-2011066389 A1 | 6/2011 |
| WO | WO-2012145493 A1 | 10/2012 |
| WO | WO-2013079174 A1 | 6/2013 |
| WO | WO-2013173223 A1 | 11/2013 |

(Continued)

OTHER PUBLICATIONS

Wang et al (PD-L1 expression in human cancers and its association with clinical outcomes, OncoTargets and Therapy, 2016), (Year: 2016).*

Vogelstein, B., and Kinzler, K.W., "Cancer genes and the pathways they control," Nat Med 10(8):789-799, Nature Portfolio, Germany (Aug. 2004).

Auvaro, P., et al., OPDIVO NHI Price cut decision released [online] Retrieved from the internet, Retrieved on Sep. 9, 2021 Nov. 24, 2016, Linkedin <url:https://www.linkedin.com/pulse/opdivo-nhi-price-cut-decision-released-philippe-auvaro> (Year: 2016).

Kazandijan, D., et al., "FDA Approval Summary: Nivolumab for the Treatment of Metastatic Non-Small Cell Lung Cancer With Progression On or After Platinum-Based Chemotherapy," Oncologist 21(5):634-642, Oxford Academic Press, United Kingdom (May 2016).

(Continued)

*Primary Examiner* — Mark Halvorson
*Assistant Examiner* — Dennis J Sullivan
(74) *Attorney, Agent, or Firm* — Sterne, Kessler, Goldstein & Fox P.L.L.C.

(57) ABSTRACT

This disclosure provides a method for treating a subject afflicted with tumor, which method comprises administering to the subject an antibody or an antigen-binding portion thereof that specifically binds to a Programmed Death-1 (PD-1) receptor and inhibits PD-1 activity. In some embodiments, the tumor is derived from a non-small cell lung cancer (NSCLC). In some embodiments, the tumor expresses Programmed Death Ligand 1. In some embodiments, the subject carries a wild-type STK11 gene.

20 Claims, 31 Drawing Sheets

(56) References Cited

FOREIGN PATENT DOCUMENTS

| | | |
|---|---|---|
| WO | WO-2013181634 A2 | 12/2013 |
| WO | WO-2014179664 A2 | 11/2014 |
| WO | WO-2014194302 A2 | 12/2014 |
| WO | WO-2014206107 A1 | 12/2014 |
| WO | WO-2015035606 A1 | 3/2015 |
| WO | WO-2015085847 A1 | 6/2015 |
| WO | WO-2015112800 A1 | 7/2015 |
| WO | WO-2015112900 A1 | 7/2015 |
| WO | WO-2015116868 A2 | 8/2015 |
| WO | WO-2016106159 A1 | 6/2016 |
| WO | WO-2016149201 A2 | 9/2016 |
| WO | WO-2016191751 A1 | 12/2016 |
| WO | WO-2016197367 A1 | 12/2016 |
| WO | WO-2017019846 A1 | 2/2017 |
| WO | WO-2017020291 A1 | 2/2017 |
| WO | WO-2017020858 A1 | 2/2017 |
| WO | WO-2017024465 A1 | 2/2017 |
| WO | WO-2017024515 A1 | 2/2017 |
| WO | WO-2017025016 A1 | 2/2017 |
| WO | WO-2017025051 A1 | 2/2017 |
| WO | WO-2017034916 A1 | 3/2017 |
| WO | WO-2017040790 A1 | 3/2017 |
| WO | WO-2017040990 A1 | 3/2017 |
| WO | WO-2017106061 A1 | 6/2017 |
| WO | WO-2017123557 A1 | 7/2017 |
| WO | WO-2017132825 A1 | 8/2017 |
| WO | WO-2017132827 A1 | 8/2017 |
| WO | WO-2017133540 A1 | 8/2017 |
| WO | WO-2017210624 A1 | 12/2017 |
| WO | WO-2018223040 A1 | 6/2018 |

OTHER PUBLICATIONS

Festino, L., et al., "Cancer Treatment with Anti-PD-1/PD-L1 Agents: Is PD-L1 Expression a Biomarker for Patient Selection?," Drugs 76(9):925-945, Springer Nature, Germany (Jun. 2016).

Borghaei, H., et al., "Nivolumab versus Docetaxel in Advanced Nonsquamous Non-Small-Cell Lung Cancer," N Engl J Med 373(17):1627-1639, Massachusetts Medical Society, United States (Oct. 2015).

Dolan, D.E., and Gupta, S., "PD-1 pathway inhibitors: changing the landscape of cancer immunotherapy," Cancer Control 21(3):231-237, SAGE Publications, United States (Jul. 2014).

Schrock, A., et al., "Updated Dataset Assessing Tumor Mutation (TMB) as a Biomarker for Response to PD-1/PD-L1 Targeted Therapies in Lung Cancer," Journal of Thoracic Oncology 12(1):S422, Elsevier, Netherlands (Jan. 2017).

Brahmer, J. R., et al., "Phase I study of single-agent anti-programmed death-1 (MDX-1106) in refractory solid tumors: safety, clinical activity, pharmacodynamics, and immunologic correlates," Journal of Clinical Oncology 28(19):3167-75, American Society of Clinical Oncology, United States (2010).

Condeelis, J., and Weissleder, R., "In Vivo Imaging in Cancer," Cold Spring Harbor Perspectives in Biology 2(12):a003848, Cold Spring Harbor Laboratory Press, United States (Dec. 2010).

Creelan, B. C., "Update on Immune Checkpoint Inhibitors in Lung Cancer," Cancer Control: Journal of the Moffitt Cancer Center 21(1):80-89, H. Lee Moffitt Cancer Center and Research Institute, United States (Jan. 2014).

Exosome Diagnostics, Inc., "Plasma-Based Solid Tumor Mutation Panel" Liquid Biopsy, Exosomedx.com, accessed at URL:[https://web.archive.org/web/20161223185114/http://exosomedx.com/sites/default/files/uploads/diagnostics/pharma_services_051816_v4.pdf] on Jun. 16, 2021, 2 pages.

Foundation Medicine, "FOUNDATIONONE® CDx: Technical Information," FoundationMedicine.com, accessed at URL:[https://www.accessdata.fda.gov/cdrh_docs/pdf17/P170019S006C.pdf] on Nov. 3, 2020, 45 pages.

Foundation Medicine, "FOUNDATIONONE® HEME: Technical Specifications," FoundationMedicine.com, published Nov. 2017, accessed at URL:[https://assets.ctfassets.net/vhribv121mne/zBxaQC12cScqgsEk8seMO/abf6133874fle5929403f66d90c3b900/F1H_TechnicalInformation_06_digital.pdf] on Nov. 3, 2020, 3 pages.

Foundation Medicine, "FOUNDATIONONE® Technical Information and Test Overview," FoundationMedicine.com, published on Aug. 18, 2014 accessed at URL:[https://assets.ctfassets.net/vhribv121mne/6YRrchSINOeSu48YwuesoY/caeec492925a7d569ce4e070866f709b/F1_-_Tech_Specs.pdf] on Nov. 3, 2020, 2 pages.

GenBank, "Serine/threonine-protein kinase STK11," Accession No. Q15831-1, accessed at URL:[https://www.ncbi.nlm.nih.gov/protein/Q15831.1] on Dec. 21, 2021, 19 pages.

GenBank, "Programmed cell death 1 ligand 1," Accession No. Q9NZQ7, accessed at https://www.ncbi.nlm.nih.gov/protein/Q9NZQ7 on Nov. 3, 2020, 5 pages.

GenBank, "Human hPD-1 (hPD-1) mRNA, complete cds," Accession No. U64863, accessed at https://www.ncbi.nlm.nih.gov/nuccore/U64863 on Nov. 3, 2020, 2 pages.

Gorelik, L., et al., "Abstract 4606: Preclinical characterization of a novel fully human IgG1 anti-PD-L1 mAb CK-301," Proceedings of 2017 AACR Annual Meeting 77(13_Supplement): Abstract 4606, Apr. 1-5, 2017, 4 pages, American Association for Cancer Research, United States (Jul. 2017).

Guardant Health, "The Guardant360® Assay Specifications," GuardantHealth.com, accessed from URL:[https://www.therapyselect.de/sites/default/files/downloads/guardant360/guardant360_specification-sheet_en.pdf] on Nov. 3, 2020, 2 pages.

Hanna, N., et al., "Randomized phase III trial of pemetrexed versus docetaxel in patients with non-small-cell lung cancer previously treated with chemotherapy," Journal of Clinical Oncology 22(9):1589-97, American Society of Clinical Oncology, United States (2004).

Herbst, R.S., et al., "A study of MPDL3280A, an engineered PD-L1 antibody in patients with locally advanced or metastatic tumors," Journal of Clinical Oncology 31(15_Suppl):3000, American Society of Clinical Oncology, United States (2013).

Hiltermann, T. J. N., et al., "Very early molecular marker of tumor response to PD-1 inhibition in plasma of patients with advanced non-small cell lung cancer (NSCLC)," Journal of Clinical Oncology 35(15_suppl):3030, American Society of Clinical Oncology, United States (May 2017).

International Search Report and Written Opinion for International Application No. PCT/US2018/035670, European Patent Office, Netherlands, mailed on Nov. 19, 2018, 18 pages.

Jamal-Hanjani, M., et al., "Translational implications of tumor heterogeneity," Clin Cancer Res 21(6):1258-66, American Association for Cancer Research Inc., United States (2015).

Kim, J. H., et al., "Prognostic value of KRAS mutation in advanced non-small-cell lung cancer treated with immune checkpoint inhibitors: A meta-analysis and review," Oncotarget 8(29):48248-48252, Impact Journals LLC, United States (Jul. 2017).

Koyama, S., et al., "STK11/LKB1 Deficiency Promotes Neutrophil Recruitment and Proinflammatory Cytokine Production to Suppress T-cell Activity in the Lung Tumor Microenvironment," Cancer Res 76(5):999-1008, American Association for Cancer Research Inc., United States (Mar. 2016).

Liu, S. Y., et al., "Ongoing Clinical Trials of PD-1 and PD-L1 Inhibitors for Lung Cancer in China," Journal of Hematology & Oncology 10(1):136, Biomed Central, United Kingdom (Jul. 2017).

McCabe, K. E., and Wu, A. M., "Positive Progress in ImmunoPET—not Just a Coincidence," Cancer Biotherapy & Radiopharmaceuticals 25(3):253-261, Mary Ann Liebert, Inc, United States (Jun. 2010).

McGranahan, N., et al., "Clonal neoantigens elicit T cell immunoreactivity and sensitivity to immune checkpoint blockade," Science 351(6280):1463-1469, American Association for the Advancement of Science, United States (Mar. 2016).

NCCN Guidelines®, "Non-Small Cell Lung Cancer Version 3.2014," National Comprehensive Cancer Network, accessed at http://www.24hmb.com/voimages/web_image//upload/file/20140416/28501397633488076.pdf on Nov. 3, 2020, 148 pages.

Olafsen, T., et al., "ImmunoPET Imaging of B-Cell Lymphoma Using 124I-Anti-CD20 scFv Dimers (Diabodies)," Protein Engineering, Design & Selection 23(4):243-249, Oxford University Press, United Kingdom (Apr. 2010).

(56) References Cited

OTHER PUBLICATIONS

Shien, K., et al., "Predictive biomarkers of response to PD-1/PD-L1 immune checkpoint inhibitors in non-small cell lung cancer," Lung Cancer 99:79-87, Elsevier Ireland Ltd., Netherlands (Sep. 2016).
Siegel, R., et al., "Cancer statistics, 2014," CA Cancer J Clin 64(1):9-29, Wiley-Blackwell, United States (2014).
Sjoblom, T., et al., "The Consensus Coding Sequences of Human Breast and Colorectal Cancers," Science 314(5797):268-274, American Association for the Advancement of Science, United States (Oct. 2006).
Skoulidis, F., et al., "Co-occurring genomic alterations define major subsets of KRAS-mutant lung adenocarcinoma with distinct biology, immune profiles, and therapeutic vulnerabilities," Cancer Discov 5(8):860-877, American Association for Cancer Research Inc., United States (Aug. 2015).
Skoulidis, F., et al., "STK11/LKB1 co-mutations to predict for de novo resistance to PD-1/PD-L1 axis blockade in KRAS-mutant lung adenocarcinoma," Journal of Clinical Oncology 35(15_Suppl):9016, American Society of Clinical Oncology, United States (May 2017).
Skoulidis, F., et al., "MA 05.02 STK11/LKB1 Loss of Function Genomic Alterations Predict Primary Resistance to PD-1/PD-L1 Axis Blockade in KRAS-Mutant NSCLC," Journal of Thoracic Oncology 12(11_Suppl 2):S1815, Elsevier, Netherlands (Nov. 2017).
Skoulidis, F., et al., "STK11/LKB1 Mutations and PD-1 Inhibitor Resistance in KRAS-Mutant Lung Adenocarcinoma," Cancer Discov 8(7):822-835, American Association for Cancer Research Inc., United States (Jul. 2018).
Taube, J. M., et al., "Colocalization of inflammatory response with B7-h1 expression in human melanocytic lesions supports an adaptive resistance mechanism of immune escape," Sci Transl Med 4(127):127ra37, American Association for the Advancement of Science, United States (2012).
United States Food and Drug Administration, "Evaluation of Automatic Class III Designation for MSK-IMPACT (Integrated Mutation Profiling of Actionable Cancer Targets): Decision Summary," accessdata.fda.gov, accessed at URL:[https://www.accessdata.fda.gov/cdrh_docs/reviews/den170058.pdf] on Nov. 4, 2020, 57 pages.
Vogelstein, B., et al., "Cancer genome landscapes," Science 339(6127):1546-1558, American Association for the Advancement of Science, United States (2013).
Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (Sep. 2014).
Yap, T. A., et al., "Intratumor Heterogeneity: Seeing the Wood for the Trees," Sci Tranl Med 4(127): 127ps10, pp. 1-5, American Association for the Advancement of Science, United States (2012).
Zhang, F., et al., "Structural basis of a novel PD-L1 nanobody for immune checkpoint blockade," Cell Discov 3:17004, Nature Publishing Group, United Kingdom (Mar. 2017).
Hellmann, M., et al., "Genomic profile, smoking, and response to anti-PD-1 therapy in non-small cell lung carcinoma," Mol Cell Oncology 3(1):e1048929, Taylor & Francis, United Kingdom (Jan. 2016).
Carbognin, L., et al., "Differential Activity of Nivolumab, Pembrolizumab and MPDL3280A according to the Tumor Expression of Programmed Death-Ligand-1 (PD-L1): Sensitivity Analysis of Trials in Melanoma, Lung and Genitourinary Cancers," PLoS One 10(6):e0130142, Public Library of Science, United States (Jun. 2015).
Scheel, A.H., et al., "PD-L1 expression in non-small cell lung cancer: Correlations with genetic alterations," Oncoimmunology 5(5):e1131379, Landes Bioscience, United States (Mar. 2016).
Dong, Z.Y., et al. "Potential Predictive Value of TP53 and KRAS Mutation Status for Response to PD-1 Blockade Immunotherapy in Lung Adenocarcinoma," Clin Cancer Res 23(12):3012-3024, American Association for Cancer Research, United States (Jun. 2017).
Peyser, N.D., et al. "Loss-of-Function PTPRD Mutations Lead to Increased STAT3 Activation and Sensitivity to STAT3 Inhibition in Head and Neck Cancer," PLoS One 10(8):e0135750, PLOS, United States (Aug. 2015).

\* cited by examiner

Diffuse

Tumor-stroma interface

Heterogeneous

Negative

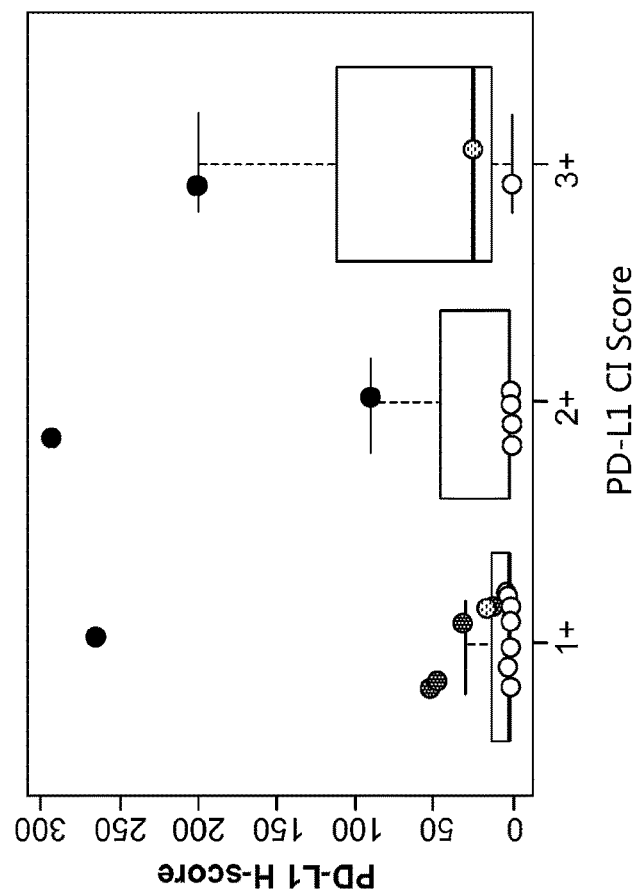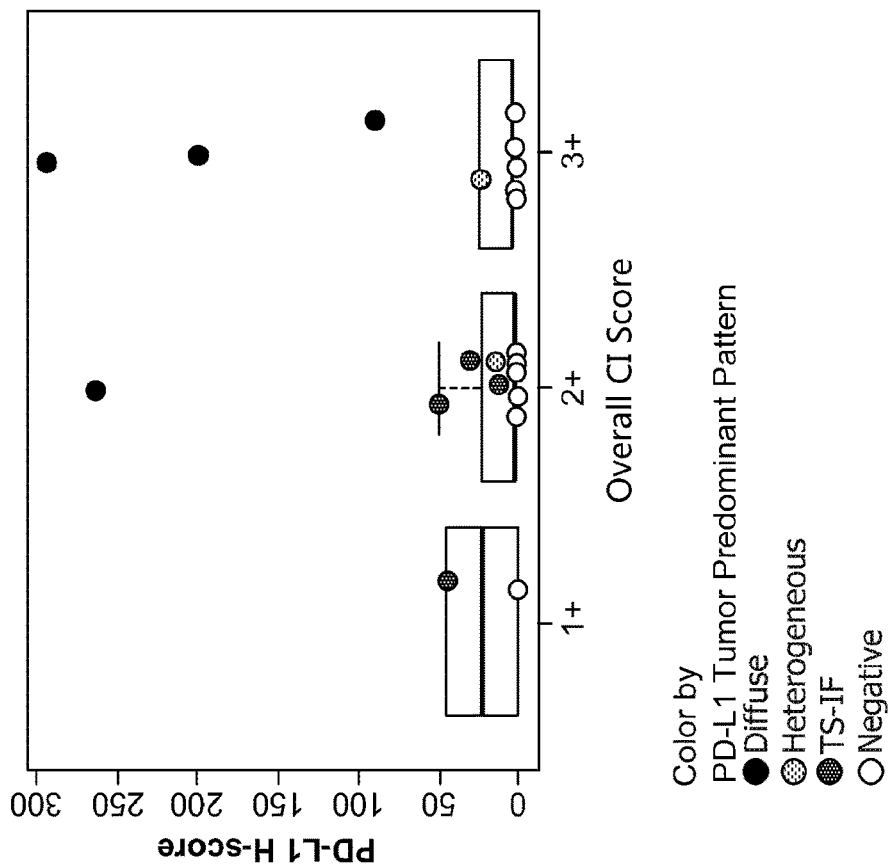

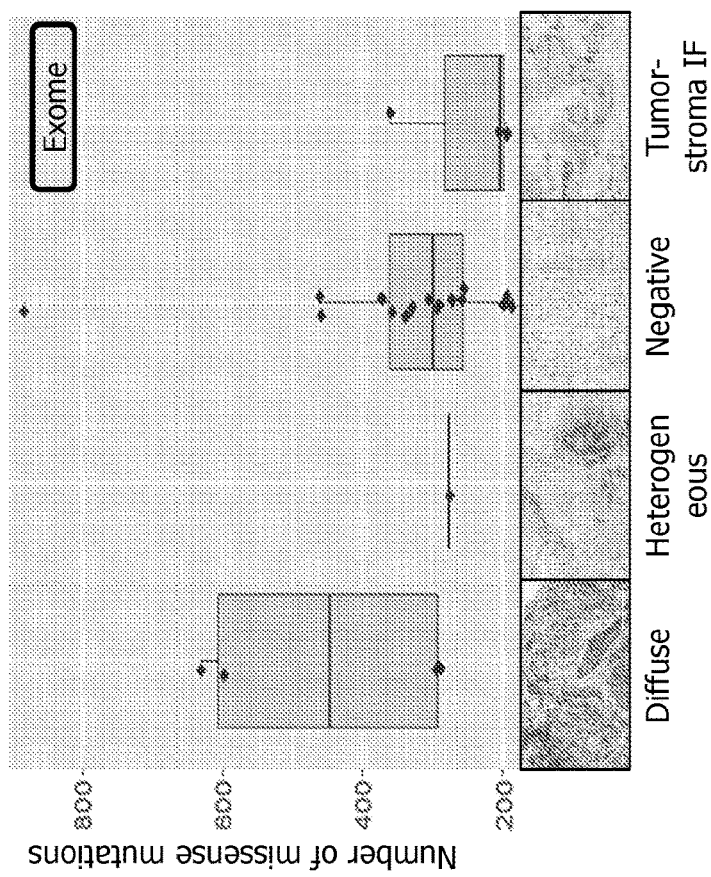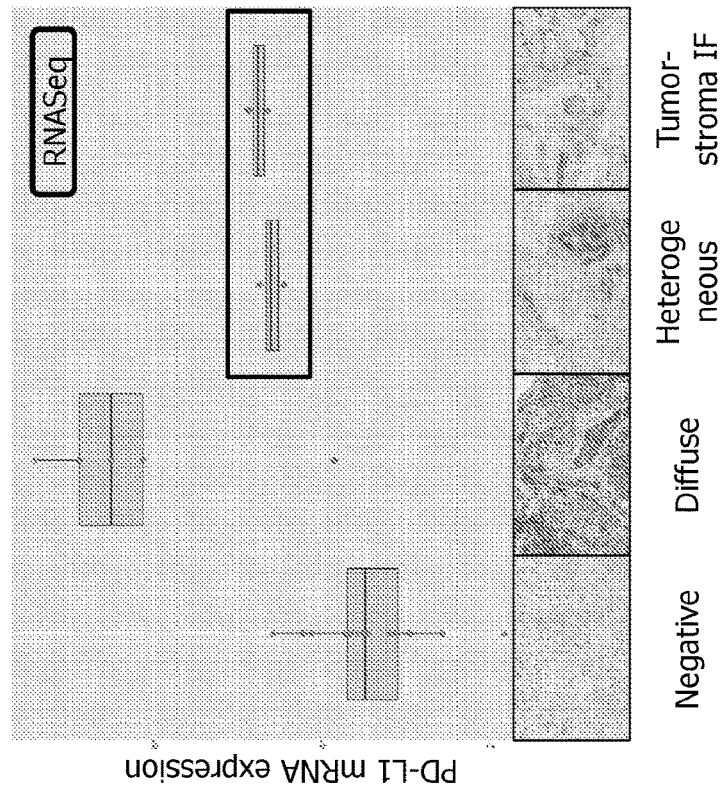
FIG. 7

STK11 vs. PDL1 IHC pattern
Fisher exact test p=0.077

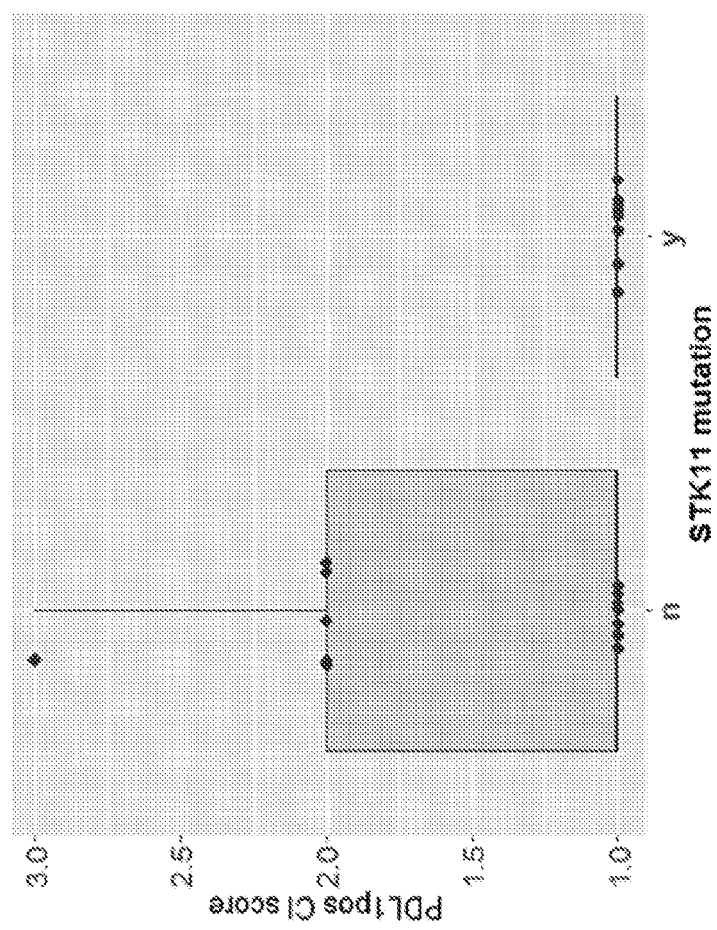

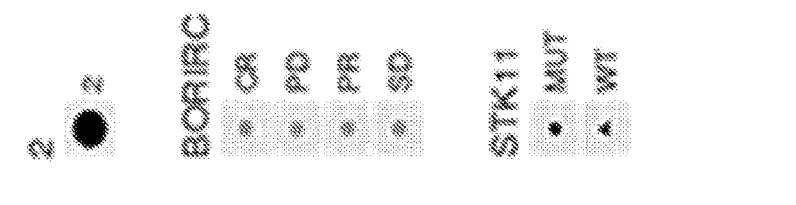
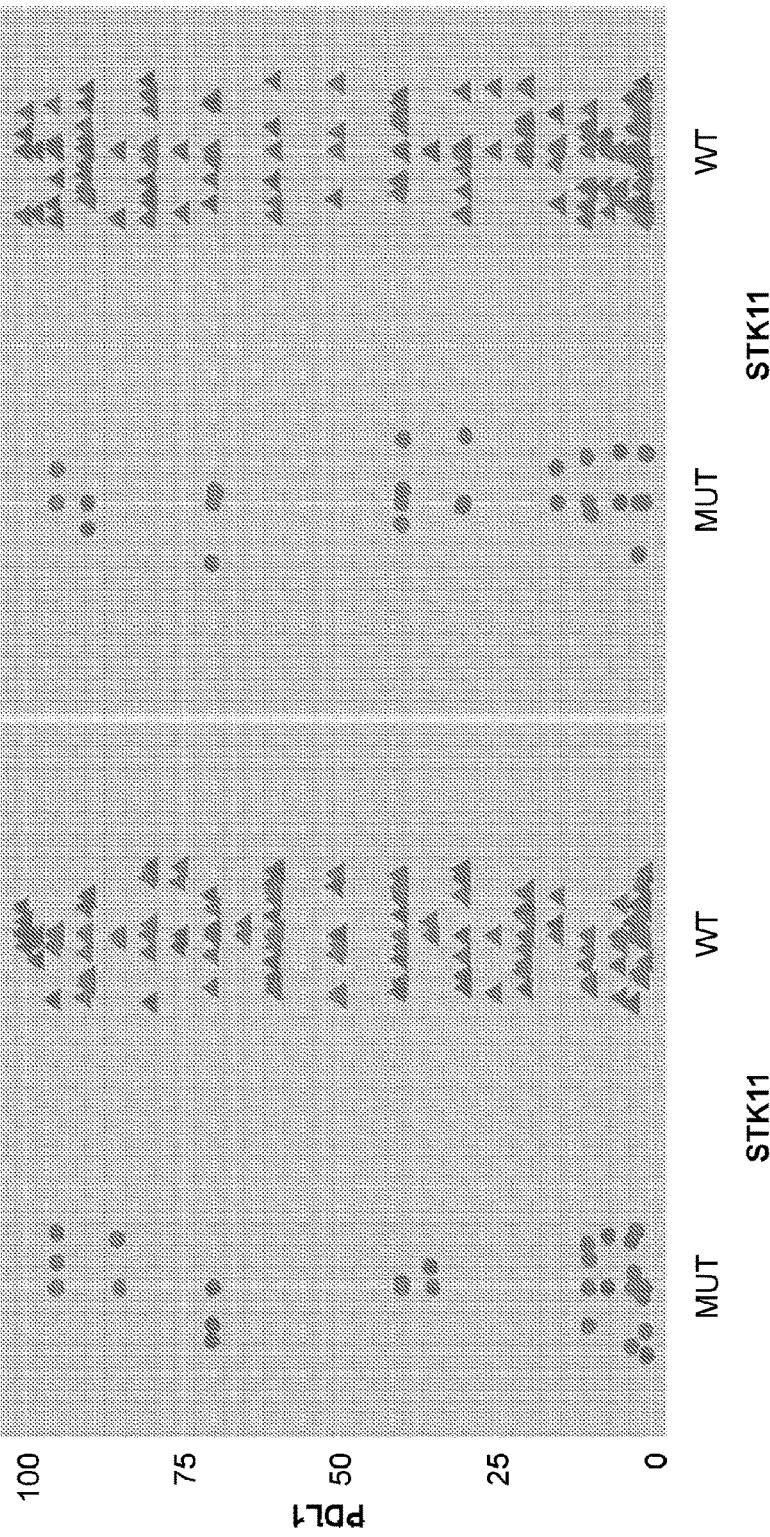

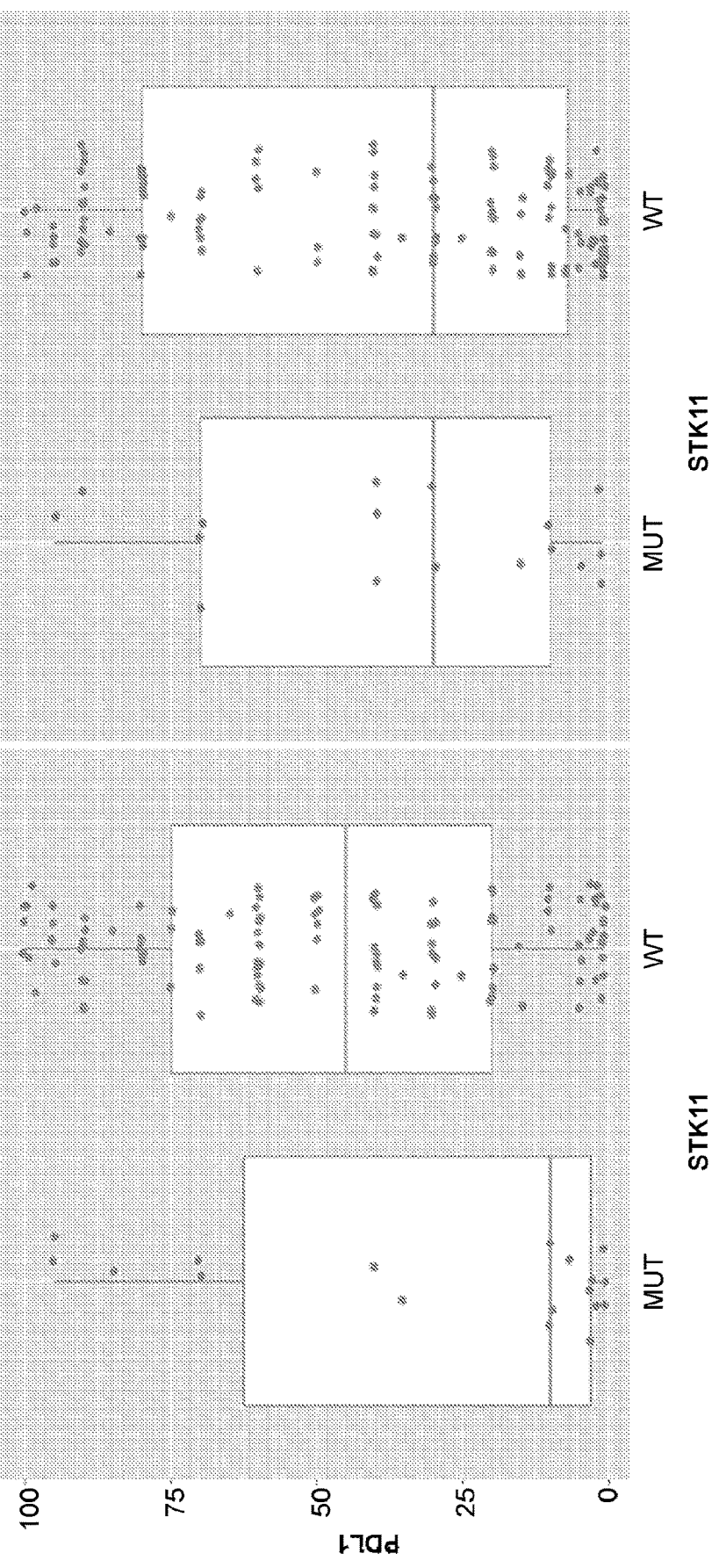

| HGVSp_Short | ACTARM | STRAT17C | BORINV | PFSIRC1 | PFSIRC1.CNSR | PDL1 | TUMLOC |
|---|---|---|---|---|---|---|---|
| p.Q37* | NIVOLUMAB 3 mg/kg | NON-SQUAMOUS | NE | 0.032854 | 1 | 40 | METASTASIS |
| p.Q214* | NIVOLUMAB 3 mg/kg | NON-SQUAMOUS | NE | 1.347023 | 0 | 1 | PRIMARY |
| p.E57Kfs*7 | NIVOLUMAB 3 mg/kg | NON-SQUAMOUS | PD | 2.102669 | 0 | 95 | PRIMARY |
| p.G171Afs*116 | NIVOLUMAB 3 mg/kg | SQUAMOUS | PD | 1.182752 | 1 | 70 | METASTASIS |
| p.R40Qfs*119 | NIVOLUMAB 3 mg/kg | NON-SQUAMOUS | PD | 0.657084 | 0 | 70 | PRIMARY |
| p.E70* | NIVOLUMAB 3 mg/kg | NON-SQUAMOUS | PD | 1.445585 | 1 | 40 | PRIMARY |
| p.K84* | NIVOLUMAB 3 mg/kg | NON-SQUAMOUS | PD | 0.394251 | 0 | 40 | METASTASIS |
| p.R310P | NIVOLUMAB 3 mg/kg | SQUAMOUS | PD | 1.215606 | 0 | 30 | METASTASIS |
| p.D194Y | NIVOLUMAB 3 mg/kg | NON-SQUAMOUS | PD | 0.985626 | 0 | 15 | PRIMARY |
| p.A153D | NIVOLUMAB 3 mg/kg | NON-SQUAMOUS | PD | 2.792608 | 0 | 10 | METASTASIS |
| p.G196V | NIVOLUMAB 3 mg/kg | NON-SQUAMOUS | PD | 1.215606 | 1 | 10 | PRIMARY |
| p.P179L | NIVOLUMAB 3 mg/kg | NON-SQUAMOUS | PD | 7.063655 | 0 | 2 | PRIMARY |
| p.D194Y | NIVOLUMAB 3 mg/kg | NON-SQUAMOUS | PR | 8.246407 | 0 | 90 | METASTASIS |
| p.Q382E | NIVOLUMAB 3 mg/kg | NON-SQUAMOUS | PR | 4.13963 | 0 | 70 | |
| p.G276V | NIVOLUMAB 3 mg/kg | NON-SQUAMOUS | PR | 24.9692 | 1 | 5 | PRIMARY |
| p.P281Rfs*6 | NIVOLUMAB 3 mg/kg | NON-SQUAMOUS | PR | 6.997947 | 0 | 1 | PRIMARY |
| p.G196V | NIVOLUMAB 3 mg/kg | NON-SQUAMOUS | SD | 1.182752 | 0 | 40 | PRIMARY |
| p.X288_splice | NIVOLUMAB 3 mg/kg | NON-SQUAMOUS | SD | 1.314168 | 0 | 30 | METASTASIS |
| p.X199_splice | NIVOLUMAB 3 mg/kg | NON-SQUAMOUS | SD | 6.833676 | 0 | 1 | METASTASIS |

FIG. 15F

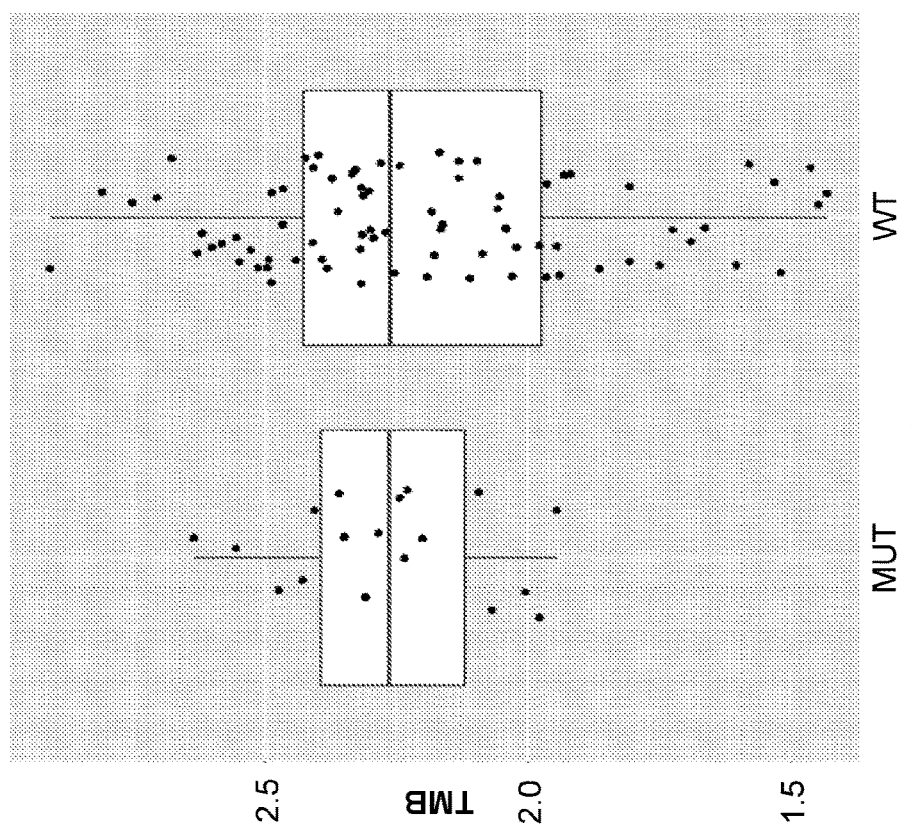
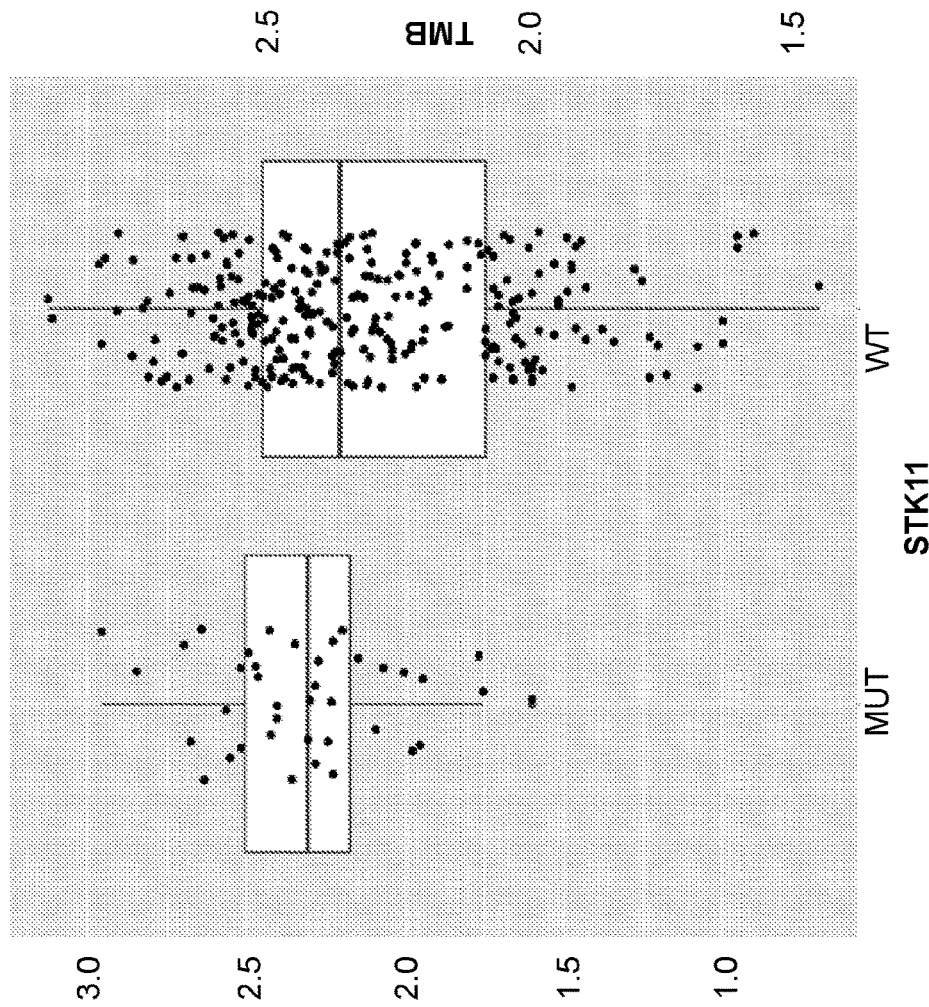
FIG. 17A
FIG. 17B

METHODS OF TREATING A TUMOR USING AN ANTI-PD-1 ANTIBODY

CROSS REFERENCE TO RELATED APPLICATIONS

This application is a continuation application of U.S. application Ser. No. 16/617,725, which is the U.S. National Phase of International Application No. PCT/US2018/035670, filed on Jun. 1, 2018, which claims the benefit of U.S. Provisional Application No. 62/513,831, filed Jun. 1, 2017, each of which is incorporated by reference herein in its entirety.

FIELD OF THE INVENTION

This disclosure relates to methods for treating a tumor comprising administering to the subject an anti-Programmed Death-1 (PD-1) antibody, wherein the subject carries wild-type STK11.

BACKGROUND OF THE INVENTION

Human cancers harbor numerous genetic and epigenetic alterations, generating neoantigens potentially recognizable by the immune system (Sjoblom et al. (2006) Science 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down-regulate T cell activation and cytokine secretion upon binding to PD-1.

Nivolumab (formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2 (9): 846-56).

NSCLC is the leading cause of cancer death in the U.S. and worldwide (NCCN GUIDELINES®, Version 3.2014-Non-Small Cell Lung Cancer, available at: nccn.org/professionals/physician_gls/pdf/nscl.pdf, last accessed May 14, 2014). NSCLCs are relatively insensitive to chemotherapy but patients with Stage IV disease who have a good performance status (PS) benefit from treatment with chemotherapeutic drugs, including platinum agents (e.g., cisplatin, carboplatin), taxanes agents (e.g., paclitaxel, albumin-bound paclitaxel, docetaxel), vinorelbine, vinblastine, etoposide, pemetrexed and gemcitabine, and various combinations of these drugs.

SUMMARY OF THE INVENTION

The present disclosure provides a method for treating a subject afflicted with a tumor comprising (i) determining a mutation status of an STK11 gene in the subject; and (ii) administering to the subject an antibody or an antigen-binding portion thereof that binds specifically to a Programmed Death-1 (PD-1) receptor and inhibits PD-1 activity ("anti-PD-1 antibody") if the STK11 gene is wild-type. In other aspects, the present disclosure relates to methods for treating a subject afflicted with a tumor comprising administering to the subject an anti-PD-1 antibody, wherein the subject is identified as having a wild-type STK11 gene. In other aspects, the present disclosure relates to methods for identifying a subject afflicted with a tumor suitable for an anti-PD-1 antibody treatment comprising (i) determining a mutation status of an STK11 gene in the subject; and (ii) administering to the subject anti-PD-1 antibody if the STK11 gene is wild-type. In some embodiments, the method further comprises detecting a mutation status of a marker gene selected from the group consisting of KRAS, TP53, CDKN2A, PTPND, CUBN, HERC1, and any combination thereof.

In other aspects, the present disclosure relates to methods for treating a subject afflicted with a tumor comprising (i) determining a mutation status of marker gene in the subject; and (ii) administering to the subject an anti-PD-1 antibody if the marker gene is mutated; wherein the marker gene is selected from the group consisting of TP53, CDKN2A, PTPND, CUBN, HERC1, and any combination thereof. In other aspects, the present disclosure relates to methods for treating a subject afflicted with a tumor comprising administering to the subject an anti-PD-1 antibody, wherein the subject is identified as having a mutated marker gene, wherein the marker gene is selected from the group consisting of TP53, CDKN2A, PTPND, CUBN, HERC1, and any combination thereof. In other aspects, the present disclosure relates to methods for identifying a subject afflicted with a tumor suitable for an anti-PD-1 antibody treatment comprising (i) determining a mutation status of a marker gene in the subject; and (ii) administering to the subject anti-PD-1 antibody if the marker gene is mutated; wherein the marker gene is selected from the group consisting of TP53, CDKN2A, PTPND, CUBN, HERC1, and any combination thereof. In some embodiments, TP53 is mutated. In some embodiments, CDKN2A is mutated. In some embodiments, PTPND, CUBN, and HERC1 are mutated.

In some embodiments, the marker gene comprises a non-synonymous mutation. In certain embodiments, the marker gene comprises a nonsense, frameshift, or splicing mutation.

In some embodiments, the tumor is derived from a lung cancer. In certain embodiments, the tumor is derived from a small cell lung cancer (SCLC) or a non-small cell lung cancer (NSCLC). In certain embodiments, the tumor is derived from an NSCLC. In particular embodiments, the tumor is derived from a non-squamous cell NSCLC. In other embodiments, the tumor is derived from a squamous cell NSCLC.

In some embodiments, the methods further comprise detecting PD-L1 expression in the tumor prior to administration. In some embodiments, the tumor expresses PD-L1 in a diffuse pattern. In some embodiments, the tumor expresses PD-L1 in a heterogeneous pattern.

In some embodiments, the mutation status of the STK11 gene is determined by sequencing the STK11 gene.

In some embodiments, the tumor has a tumor mutational burden (TMB) status that is a high TMB. In some embodiments, the tumor TMB status is determined by sequencing nucleic acids in the tumor and identifying a genomic alteration in the sequenced nucleic acids.

In some embodiments, the tumor exhibits high inflammation. In some embodiments, the inflammation is measured according to the expression of STK11.

In some embodiments, the anti-PD-1 antibody cross-competes with nivolumab for binding to human PD-1. In some embodiments, the anti-PD-1 antibody binds to the same epitope as nivolumab. In some embodiments, the anti-PD-1 antibody is a chimeric, humanized or human monoclonal antibody or a portion thereof. In some embodiments, the anti-PD-1 antibody comprises a heavy chain constant region which is of a human IgG1 or IgG4 isotype. In some embodiments, the anti-PD-1 antibody is nivolumab.

In some embodiments, the anti-PD-1 antibody is administered at a dose ranging from at least about 0.1 mg/kg to at least about 10.0 mg/kg body weight once about every 1, 2 or 3 weeks. In some embodiments, the anti-PD-1 antibody or antigen-binding portion thereof is administered at a flat dose. In some embodiments, the anti-PD-1 antibody or antigen-binding portion thereof is administered at a flat dose or about 240 mg.

In some embodiments, the administering treats the tumor. In some embodiments, the administering reduces the size of the tumor. In some embodiments, the subject exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the initial administration. In some embodiments, the subject exhibits a partial response after the administration. In some embodiments, the subject exhibits a complete response after the administration.

In other aspects, this disclosure provides a kit for treating a subject afflicted with a tumor, the kit comprising: (a) a dosage ranging from about 4 mg to about 500 mg of an anti-PD-1 antibody; and (b) instructions for using the anti-PD-1 antibody in any method disclosed herein. In some embodiments, the kit further comprises an anti-PD-L1 antibody.

Embodiments

E1. A method for treating a subject afflicted with a tumor comprising (i) determining a mutation status of an STK11 gene in the subject; and (ii) administering to the subject an antibody or an antigen-binding portion thereof that binds specifically to a Programmed Death-1 (PD-1) receptor and inhibits PD-1 activity ("anti-PD-1 antibody") if the STK11 gene is wild-type.

E2. A method for treating a subject afflicted with a tumor comprising administering to the subject an anti-PD-1 antibody, wherein the subject is identified as having a wild-type STK11 gene.

E3. A method for identifying a subject afflicted with a tumor suitable for an anti-PD-1 antibody treatment comprising (i) determining a mutation status of an STK11 gene in the subject; and (ii) administering to the subject anti-PD-1 antibody if the STK11 gene is wild-type.

E4. The method of any one of E1 to E3, further comprising detecting a mutation status of a marker gene selected from the group consisting of KRAS, TP53, CDKN2A, PTPND, CUBN, HERC1, and any combination thereof.

E5. A method for treating a subject afflicted with a tumor comprising (i) determining a mutation status of marker gene in the subject; and (ii) administering to the subject an antibody or an antigen-binding portion thereof that binds specifically to a Programmed Death-1 (PD-1) receptor and inhibits PD-1 activity ("anti-PD-1 antibody") if the marker gene is mutated; wherein the marker gene is selected from the group consisting of TP53, CDKN2A, PTPND, CUBN, HERC1, and any combination thereof.

E6. A method for treating a subject afflicted with a tumor comprising administering to the subject an anti-PD-1 antibody, wherein the subject is identified as having a mutated marker gene, wherein the marker gene is selected from the group consisting of TP53, CDKN2A, PTPND, CUBN, HERC1, and any combination thereof.

E7. A method for identifying a subject afflicted with a tumor suitable for an anti-PD-1 antibody treatment comprising (i) determining a mutation status of a marker gene in the subject; and (ii) administering to the subject anti-PD-1 antibody if the marker gene is mutated; wherein the marker gene is selected from the group consisting of TP53, CDKN2A, PTPND, CUBN, HERC1, and any combination thereof.

E8. The method of any one of E4 to E7, wherein TP53 is mutated.

E9. The method of any one of E4 to E8, wherein CDKN2A is mutated.

E10. The method of any one of E4 to E9, wherein PTPND, CUBN, and HERC1 are mutated.

E11. The method of any one of E4 to E10, wherein the marker gene comprises a non-synonymous mutation.

E12. The method of any one of E4 to E11, wherein the marker gene comprises a nonsense, frameshift, or splicing mutation.

E13. The method of any one of E1 to E12, wherein the tumor is derived from a lung cancer.

E14. The method of E13, wherein the tumor is derived from a small cell lung cancer (SCLC) or a non-small cell lung cancer (NSCLC).

E15. The method of E14, wherein the tumor is derived from an NSCLC.

E16. The method of E15, wherein the tumor is derived from a non-squamous cell NSCLC.

E17. The method of E15, wherein the tumor is derived from a squamous cell NSCLC.

E18. The method of any one of E1 to E17, further comprising detecting PD-L1 expression in the tumor prior to administration.

E19. The method of E18, wherein the tumor expresses PD-L1 in a diffuse pattern.

E20. The method of E19, wherein the diffuse pattern of PD-L1 expression is characterized by a PD-L1 H-score of from about 60 to about 500, from about 80 to about 480, from about 100 to about 460, from about 120 to about 440, from about 140 to about 420, from about 160 to about 400, from about 180 to about 380, from about 200 to about 360, from about 200 to about 340, from about 200 to about 320, or from about 200 to about 300.

E21. The method of E19, wherein the diffuse pattern of PD-L1 expression is characterized by a PD-L1 H-score of at least about 60, at least about 70, at least about 80, at least about 90, at least about 100, at least about 110, at least about 120, at least about 130, at least about 140, at least about 150, at least about 160, at least about 170, at least about 180, at least about 190, at least about 200, at least about 225, at least about 250, at least about 275, or at least about 300.

E22. The method of E21, wherein the diffuse pattern of PD-L1 expression is characterized by a PD-L1 H-score of at least about 200.

E23. The method of E18, wherein the tumor expresses PD-L1 in a heterogeneous pattern.

E24. The method of E23, wherein the heterogeneous pattern of PD-L1 expression is characterized by a PD-L1 H-score of from about 1 to about 50, from about 5 to about 45, from about 10 to about 40, or from about 15 to about 35, and wherein the PD-L1 expression is restricted to one or more distinct portions of the tumor.

E25. The method E23, wherein the heterogeneous pattern of PD-L1 expression is characterized by a PD-L1 H-score of at least about 5, at least about 10, at least about 15, at least about 20, at least about 25, at least about 30, at least about 35, or at least about 40.

E26. The method of E25, wherein the heterogeneous pattern of PD-L1 expression is characterized by a PD-L1 H-score of at least about 15.

E27. The method of any one of E1, 3, 4, and 13 to E26, wherein the mutation status of the STK11 gene is determined by sequencing the STK11 gene.

E28. The method of any one of E18 to E27, wherein PD-L1 expression is detected using an immunohistochemistry (IHC) assay.

E29. The method of E28, wherein the IHC assay is an automated IHC assay.

E30. The method of E28 or E29, wherein the IHC assay is performed using an anti-PD-L1 monoclonal antibody that specifically binds to the PD-L1 and wherein the anti-PD-L1 monoclonal antibody is selected from the group consisting of 28-8, 28-1, 28-12, 29-8, 5H1, and any combination thereof.

E31. The method of any one of E18 to E30, wherein at least about 1%, at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of tumor cells express PD-L1.

E32. The method of any one of E1 to E31, wherein the tumor has a tumor mutational burden (TMB) status that is a high TMB.

E33. The method of E32, wherein the tumor TMB status is determined by sequencing nucleic acids in the tumor and identifying a genomic alteration in the sequenced nucleic acids.

E34. The method of E33, wherein the genomic alteration comprises one or more somatic mutations.

E35. The method of E33 or E34, wherein the genomic alteration comprises one or more non-synonymous mutations.

E36. The method of any one of E33 to E35, wherein the genomic alteration comprises one or more missense mutations.

E37. The method of any one of E33 to E36, wherein the genomic alteration comprises one or more alterations selected from the group consisting of a base pair substitution, a base pair insertion, a base pair deletion, a copy number alteration (CNAs), a gene rearrangement, and any combination thereof.

E38. The method of any one of E32 to E37, wherein the high TMB has a score of at least 210, at least 215, at least 220, at least 225, at least 230, at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, at least 400, at least 405, at least 410, at least 415, at least 420, at least 425, at least 430, at least 435, at least 440, at least 445, at least 450, at least 455, at least 460, at least 465, at least 470, at least 475, at least 480, at least 485, at least 490, at least 495, or at least 500.

E39. The method of any one of E32 to E38, wherein the high TMB has a score of at least 215, at least 220, at least 221, at least 222, at least 223, at least 224, at least 225, at least 226, at least 227, at least 228, at least 229, at least 230, at least 231, at least 232, at least 233, at least 234, at least 235, at least 236, at least 237, at least 238, at least 239, at least 240, at least 241, at least 242, at least 243, at least 244, at least 245, at least 246, at least 247, at least 248, at least 249, or at least 250.

E40. The method of any one of E32 to E39, wherein the high TMB has a score of at least 243.

E41. The method of any one of E32 to E40, further comprising comparing the subject's TMB status to a reference TMB value.

E42. The method of E41, wherein the subject's TMB status is within the highest fractile of the reference TMB value.

E43. The method of E41, wherein the subject's TMB status is within the top tertile of the reference TMB value.

E44. The method of any one of E32 to E43, wherein the TMB status is determined by genome sequencing.

E45. The method of any one of E32 to E43, wherein the TMB status is determined by exome sequencing.

E46. The method of any one of E32 to E45, wherein the TMB status is determined by genomic profiling.

E47. The method of any one of E1 to E46, wherein the tumor exhibits high inflammation.

E48. The method of E47, wherein the inflammation is measured according to the expression of STK11.

E49. The method of any one of E1 to E48, wherein the anti-PD-1 antibody cross-competes with nivolumab for binding to human PD-1.

E50. The method of any one of E1 to E49, wherein the anti-PD-1 antibody binds to the same epitope as nivolumab.

E51. The method of any one of E1 to E50, wherein the anti-PD-1 antibody is a chimeric, humanized or human monoclonal antibody or a portion thereof.

E52. The method of any one of E1 to E51, wherein the anti-PD-1 antibody comprises a heavy chain constant region which is of a human IgG1 or IgG4 isotype.

E53. The method of any one of E1 to E52, wherein the anti-PD-1 antibody is nivolumab.

E54. The method of any one of E1 to E53, wherein the anti-PD-1 antibody is pembrolizumab.

E55. The method of any one of E1 to E54, wherein the anti-PD-1 antibody is administered at a dose ranging from at least about 0.1 mg/kg to at least about 10.0 mg/kg body weight once about every 1, 2 or E3 weeks.

E56. The method of E55, wherein the anti-PD-1 antibody is administered at a dose of at least about 3 mg/kg body weight once about every 2 weeks.

E57. The method of any one of E1 to E56, wherein the anti-PD-1 antibody or antigen-binding portion thereof is administered at a flat dose.

E58. The method of any one of E1 to E54 and 57, wherein the anti-PD-1 antibody or antigen-binding portion thereof is administered at a flat dose of at least about 200, at least about 220, at least about 240, at least about 260, at least about 280, at least about 300, at least about 320, at least about 340, at least about 360, at least about 380, at least about 400, at least about 420, at least about 440, at least about 460, at least about 480, at least about 500 or at least about 550 mg.

E59. The method of any one of E1 to E54, 57, and 58, wherein the anti-PD-1 antibody or antigen-binding portion thereof is administered at a flat dose of about 240 mg.

E60. The method of any one of E1 to E54, and 57 to E59, wherein the anti-PD-1 antibody or antigen-binding portion thereof is administered at a flat dose about once every 1, 2, 3 or E4 weeks.

E61. The method of any one of E1 to E60, wherein the anti-PD-1 antibody is administered for as long as clinical benefit is observed or until unmanageable toxicity or disease progression occurs.

E62. The method of any one of E1 to E61, wherein the anti-PD-1 antibody is formulated for intravenous administration.

E63. The method of any one of E1 to E62, wherein the anti-PD-1 antibody is administered at a subtherapeutic dose.

E64. The method of any one of E1 to E63, wherein the administering treats the tumor.

E65. The method of any one of E1 to E64, wherein the administering reduces the size of the tumor.

E66. The method of E65, wherein the size of the tumor is reduced by at least about 10%, about 20%, about 30%, about 40%, or about 50% compared to the tumor size prior to the administration.

E67. The method of any one of E1 to E66, wherein the subject exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the initial administration.

E68. The method of any one of E1 to E67, wherein the subject exhibits stable disease after the administration.

E69. The method of any one of E1 to E67, wherein the subject exhibits a partial response after the administration.

E70. The method of any one of E1 to E67, wherein the subject exhibits a complete response after the administration.

E71. A kit for treating a subject afflicted with a tumor, the kit comprising:
  (a) a dosage ranging from about 4 mg to about 500 mg of an anti-PD-1 antibody; and
  (b) instructions for using the anti-PD-1 antibody in the method of any of E1 to E70.

E72. The kit of E71, further comprising an anti-PD-L1 antibody.

BRIEF DESCRIPTION OF THE DRAWINGS

FIGS. 3A-3C show IHC images corresponding to diffuse (FIG. 3A), tumor-stroma interface (FIG. 3B) and negative (FIG. 3C) PD-L1 expression patters corresponding to trial biopsies from patients treated with nivolumab monotherapy.

FIGS. 5A-5B show the Overall CI Score (FIG. 5A) and PD-L1 CI Score (FIG. 5B) according to PD-L1 tumor predominant pattern.

FIGS. 7A-7B show PD-L1 expression in NSCLC tumors according to PD-L1 expression pattern as measured using RNA sequencing (FIG. 7A), and the mutation load in NSCLC tumors according to PD-L1 expression pattern as measured using exome sequencing (FIG. 7B).

FIG. 9B shows PD-L1 expression measured by RNA sequencing (RNAseq) versus presence ("y") or absence ("n") of STK11 mutations.

FIG. 10A-10C show the relationship between presence ("y") or absence ("n") of STK11 mutations and PD-L1+CI Score (FIG. 10A). The numeric data corresponding to the information presented in FIG. 10A is shown in FIG. 10B. FIG. 10C shows numeric data corresponding to overall inflammation scores in NSCLC tumors depending on the presence ("STK11-MUT") or absence ("STK11-WT") of STK11 mutations.

FIG. 12A includes mutant STK11 subjects having all non-synonymous mutations to STK11, whereas FIG. 12B includes only mutant STK11 subjects having nonsense, frameshift, or splicing mutations to STK11. The numbers of subjects at risk at each time point for each group is shown below the X axis.

FIG. 14A includes all subjects meeting this criteria, whereas FIG. 14B includes only subjects that further have a KRAS mutation. The numbers of subjects at risk at each time point for each group is shown below the X axis.

FIGS. 15A-15E are graphical representation that show the relationship between PDL1 expression levels and STK11 mutation status. FIGS. 15A and 15B show the distribution of WT or mutated STK11 subjects experiencing a complete response (CR), partial response (PR), stable disease (SD), or progressive disease (PD) following treatment with either an investigator choice chemotherapy (FIG. 15A) or first-line 3 mg/kg anti-PD-1 antibody therapy (Nivolumab; FIG. 15B). FIG. 15C is a graphical representation of the distribution of WT or mutated STK11 subjects experiencing a complete response (CR), partial response (PR), stable disease (SD), or progressive disease (PD) following treatment with either an investigator choice chemotherapy or first-line 3 mg/kg anti-PD-1 antibody therapy (Nivolumab) as related to PDL1 expression levels. FIGS. 15D and 15E show the distribution PDL1 expression in WT or mutated STK11 subjects treated with either an investigator choice chemotherapy (FIG. 15D) or first-line 3 mg/kg anti-PD-1 antibody therapy (Nivolumab; FIG. 15E). The Y axes show the percent of tumor cells that express PD-L1 (FIGS. 15A-15E). FIG. 15F is a table providing the status, including the specific mutations, for a subset of the subjects having STK11 mutations.

FIGS. 17A-17B are scatter plots, illustrating the relationship between tumor mutational burden and STK11 mutation status in all advanced NSCLC subjects analyzed (FIG. 17A) or in a subpopulation further having a KRAS mutation (FIG. 17B). FIG. 17C).

FIG. 18A includes all subjects having any non-synonymous STK11 mutation; FIG. 18B includes subjects having any non-synonymous STK11 mutation and a KRAS mutation; FIG. 18C includes all subjects having any nonsense, frameshift, or splicing mutations in STK11; and FIG. 18D includes subjects having any nonsense, frameshift, or splicing mutations in STK11 and a KRAS mutation. The numbers of subjects at risk at each time point for each group is shown below the X axes (FIGS. 18A-18D).

DETAILED DESCRIPTION OF THE INVENTION

Figure 1A:
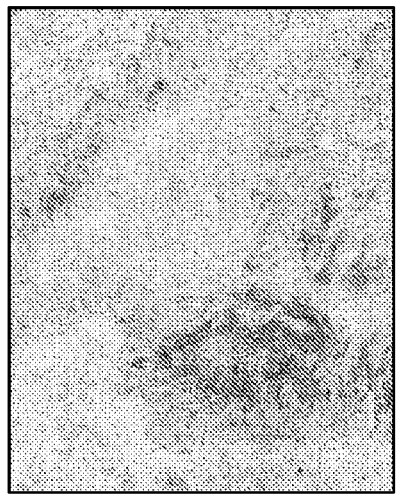
FIGS. 1A-1D present immunohistochemistry (IHC) images showing distinct patterns of PD-L1 expression in NSCLC commercial tumors. The patterns of PD-L1 expression are designated diffuse (FIG. 1A), heterogeneous (FIG. 1B), tumor-stroma interface (FIG. 1C), and negative (FIG. 1D).
Figure 1B:
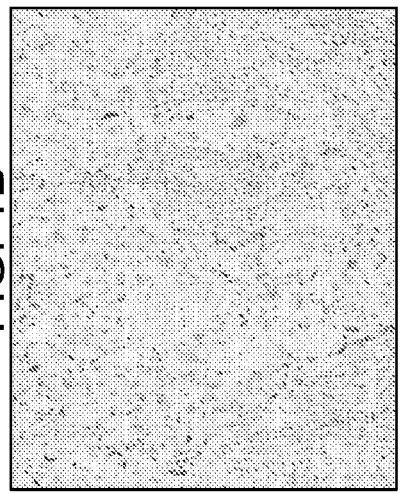
Figure 1C:
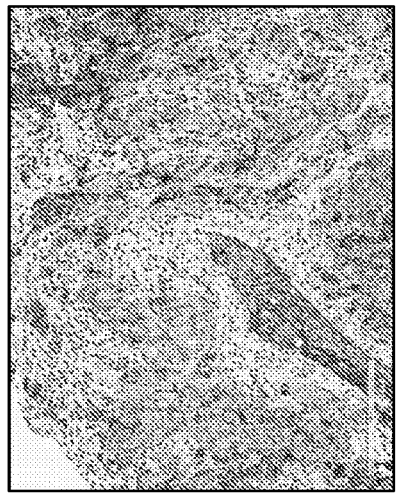
Figure 1D:

The present disclosure relates to methods for treating a subject afflicted with a tumor comprising (i) determining a mutation status of an STK11 gene in the subject; and (ii) administering to the subject an antibody or an antigen-binding portion thereof that binds specifically to a Programmed Death-1 (PD-1) receptor and inhibits PD-1 activity ("anti-PD-1 antibody") or to a Programmed Death Ligand 1 (PD-L1) and inhibits PD-1 activity ("anti-PD-L1 antibody") if the STK11 gene is wild-type. In some embodiments, the tumor is derived from a NSCLC.

Terms

In order that the present disclosure can be more readily understood, certain terms are first defined. As used in this application, except as otherwise expressly provided herein, each of the following terms shall have the meaning set forth below. Additional definitions are set forth throughout the application.

"Administering" refers to the physical introduction of a composition comprising a therapeutic agent to a subject, using any of the various methods and delivery systems known to those skilled in the art. Routes of administration for the anti-PD-1 antibody include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the combination is administered via a non-parenteral route, in some embodiments, orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. For example, an adverse event can be associated with activation of the immune system or expansion of immune system cells (e.g., T cells) in response to a treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises at least three constant domains, $C_{H1}$, $C_{H2}$ and $C_{H3}$. Each light chain comprises a light chain variable region (abbreviated herein as $V_L$) and a light chain constant region. The light chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

An immunoglobulin can derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain antibodies. A nonhuman antibody can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

An "isolated antibody" refers to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 can, however, have cross-reactivity to other antigens, such as PD-1 molecules from different species. Moreover, an isolated antibody can be substantially free of other cellular material and/or chemicals.

The term "monoclonal antibody" ("mAb") refers to a non-naturally occurring preparation of antibody molecules of single molecular composition, i.e., antibody molecules whose primary sequences are essentially identical, and which exhibits a single binding specificity and affinity for a particular epitope. A monoclonal antibody is an example of an isolated antibody. MAbs can be produced by hybridoma, recombinant, transgenic or other techniques known to those skilled in the art.

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized antibody" refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen" antibody refers to an antibody that binds specifically to the antigen. For example, an anti-PD-1 antibody binds specifically to PD-1.

An "antigen-binding portion" of an antibody (also called an "antigen-binding fragment") refers to one or more fragments of an antibody that retain the ability to bind specifically to the antigen bound by the whole antibody.

A "cancer" refers a broad group of various diseases characterized by the uncontrolled growth of abnormal cells in the body. Unregulated cell division and growth divide and grow results in the formation of malignant tumors that invade neighboring tissues and can also metastasize to distant parts of the body through the lymphatic system or bloodstream.

"Serine/Threonine Kinase 11" or "STK11" (also known as "Polarization-Related Protein LKB1," "Renal Carcinoma Antigen NY-REN-19," "Liver Kinase B1," "EC 2.7.11.1,"

and "HLKB1") refers to a member of the serine/threonine kinase family that regulates cell polarity and functions as a tumor suppressor. STK11 controls the activity of AMP-activated protein kinase (AMPK) family members, thereby playing a role in various processes such as cell metabolism, cell polarity, apoptosis and DNA damage response. STK11 is ubiquitously expressed, with the strongest expression in the testis and the fetal liver. STK11 is commonly inactivated in NSCLC, especially in tumors harboring KRAS mutations. As described herein, mutated STK11, e.g., loss of wild type expression of STK11, correlates with decreased or aberrant PD-L1 expression in tumors derived from an SCLC. In some embodiments, mutated STK11, e.g., loss of wild type expression of STK11, occurs in a tumor derived from an SCLC, wherein the tumor either expresses or does not express wild type KRAS (e.g., the tumor has or does not have a KRAS mutation). In some embodiments, the STK11 mutant is an STK11 mutant previously described in, e.g., Koyama et al., Cancer Res. 76 (5): 999-1008 (2016), Skoulidis et al., Cancer Discov. 5 (8): 860-77 (2015), and/or Skoulidis et al., Cancer Disclov., May 17, 2018, DOI: 10.1158/2159-8290.CD-18-0099, each of which is incorporated by reference herein in its entirety.

"KRAS" refers to the gene encoding the GTPase KRas protein, which is a member of the ras subfamily of small GTPases. Approximately 15-25% of patients with lung adenocarcinoma have tumor associated KRAS mutations, the majority of which mutations result in constitutively activated KRAS signaling. As used herein, "TP53" refers to the gene encoding the tumor suppressor protein p53. p53 acts to control cell division, and loss of function mutations lead to unregulated cell division and growth. Approximately half of all cancers comprise a somatic mutation of TP53. As used herein, "Cyclin Dependent Kinase Inhibitor 2A" or "CDKN2A" refers to the gene encoding cyclin dependent kinase inhibitor 2A, which acts as a tumor suppressor by inducing cell cycle arrest during G1 and G2 phases. CDKN2A loss of function mutations are common in lung cancer. As used herein, "CUBN" refers to the gene encoding cubilin, which is a receptor for intrinsic factor-vitamin B12 complexes. As used herein, "HERC1" refers to the gene encoding HECT and RLD domain containing E3 ubiquitin protein ligase family member 1 (HERC1), which is a member of the HERC family. HERC1 stimulates guanine nucleotide exchange on ARF1 and Rab proteins and may be involved in membrane transport processes.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

"PD-L1 positive" as used herein can be interchangeably used with "PD-L1 expression of at least about 1%." In one embodiment, the PD-L1 expression can be used by any methods known in the art. In another embodiment, the PD-L1 expression is measured by an automated IHC. PD-L1 positive tumors can thus have at least about 1%, at least about 2%, at least about 5%, at least about 10%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100% of the tumor cells expressing PD-L1 as measured by an automated IHC. In certain embodiments, "PD-L1 positive" means that there are at least 100 cells that express PD-L1 on the surface of the cells.

"Programmed Death-1 (PD-1)" refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

A "subject" includes any human or nonhuman animal. The term "nonhuman animal" includes, but is not limited to, vertebrates such as nonhuman primates, sheep, dogs, and rodents such as mice, rats and guinea pigs. In some embodiments, the subject is a human. The terms, "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, "subtherapeutic dose" means a dose of a therapeutic compound (e.g., an antibody) that is lower than the usual or typical dose of the therapeutic compound when administered alone for the treatment of a hyperproliferative disease (e.g., cancer).

By way of example, an "anti-cancer agent" promotes cancer regression in a subject or prevents further tumor growth. In certain embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of an anti-cancer agent can inhibit cell growth or tumor growth by at least about 20%, by at least about 40%, by at least about 60%, or by at least about 80% relative to untreated subjects. In other embodiments of the disclosure, tumor regression can be observed and continue for a period of at least about 20 days, at least about 40 days, or at least about 60 days. Notwithstanding these ultimate measurements of therapeutic effectiveness, evaluation of immunotherapeutic drugs must also make allowance for "immune-related" response patterns.

An "immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

A therapeutically effective amount of a drug includes a "prophylactically effective amount," which is any amount of the drug that, when administered alone or in combination with an anti-neoplastic agent to a subject at risk of developing a cancer (e.g., a subject having a pre-malignant condition) or of suffering a recurrence of cancer, inhibits the development or recurrence of the cancer. In certain embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

The term "wild-type," as used herein, refers to a gene that has a nucleotide sequence that encodes a protein that has an amino acid sequence known in the art to be the common sequence. For example, in some embodiments, the "wild-type" STK11 has a nucleotide sequence that encodes an STK11 protein having an amino acid sequence identical to the amino acid sequence of the protein having UniProt identifier Q15831-1. In certain aspects, a "wild-type" gene can have mutations relative to the canonical nucleotide sequence for that gene, so long as the mutations are synonymous, e.g., the nucleotide mutations do not result in changes to the amino acid sequence of the resulting protein. Conversely, "mutant" or "mutated" genes, as used herein, refer to genes that have one or more nucleotide substitution, insertion, or deletion that changes the resulting amino acid sequence, e.g., a non-synonymous mutation. Mutated genes can be expressed or unexpressed. In some embodiments, the non-synonymous mutation is a "nonsense mutation," wherein the nucleotide substitution or deletion results in the generation of a premature stop codon. In some embodiments, the non-synonymous mutation is a "frameshift mutation," wherein the nucleotide substitution or deletion comprises an insertion or deletion of a number of nucleotides not divisible by three, resulting in a shift in the translation of the sequence. In some embodiments, the non-synonymous mutation is a "splicing mutation," wherein the nucleotide substitution or deletion interferes with or creates a splice site.

The term "tumor mutation burden" (TMB) as used herein refers to the number of somatic mutations in a tumor's genome and/or the number of somatic mutations per area of the tumor's genome. Germline (inherited) variants are excluded when determining TMB, because the immune system has a higher likelihood of recognizing these as self. TMB is a genetic analysis of a tumor's genome and, thus, can be measured by applying sequencing methods well known to those of skill in the art. In one embodiment, TMB is measured using the total number of missense mutations in a tumor, identified by normalizing matched tumor with germline samples to exclude any inherited germline genetic alterations. In order to measure TMB, a sufficient amount of sample is required. In one embodiment, tissue sample (for example, a minimum of 10 slides) is used for evaluation.

The TMB status can be a numerical value or a relative value, e.g., high, medium, or low; within the highest fractile, or within the top tertile, of a reference set.

The term "high TMB" as used herein refers to a number of somatic mutations in a tumor's genome that is above a number of somatic mutations that is normal or average. In some embodiments, a TMB has a score of at least 210, at least 215, at least 220, at least 225, at least 230, at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, at least 400, at least 405, at least 410, at least 415, at least 420, at least 425, at least 430, at least 435, at least 440, at least 445, at least 450, at least 455, at least 460, at least 465, at least 470, at least 475, at least 480, at least 485, at least 490, at least 495, or at least 500; in other embodiments a high TMB has a score of at least at least 221, at least 222, at least 223, at least 224, at least 225, at least 226, at least 227, at least 228, at least 229, at least 230, at least 231, at least 232, at least 233, at least 234, at least 235, at least 236, at least 237, at least 238, at least 239, at least 240, at least 241, at least 242, at least 243, at least 244, at least 245, at least 246, at least 247, at least 248, at least 249, or at least 250; and, in a particular embodiment, a high TMB has a score of at least 243. In other embodiments, a "high TMB" refers to a TMB within the highest fractile of the reference TMB value. For example, a "reference TMB value" can be determined by grouping all subject's with evaluable TMB data according to fractile distribution of TMB, i.e., subjects are rank ordered from highest to lowest number of genetic alterations and divided into a defined number of groups. In one embodiment, all subjects with evaluable TMB data are rank ordered and divided into thirds and a "high TMB" is within the top tertile of the reference TMB value. In a particular embodiment, the tertile boundaries are 0<100 genetic alterations; 100 to 243 genetic alterations; and >243 genetic alterations. It should be understood that, once rank ordered, subjects with evaluable TMB data can be divided into any number of groups, e.g., quartiles, quintiles, etc.

As used herein, the term "medium TMB" refers to a number of somatic mutations in a tumor's genome that is at or around a number of somatic mutations that is normal or average and the term "low TMB" refers to a number of somatic mutations in a tumor's genome that is below a number of somatic mutations that is normal or average. In a particular embodiment, a "high TMB" has a score of at least 243, a "medium TMB" has a score of between 100 and 242, and a "low TMB" has a score of less than 100 (or between 0 and 100).

In some embodiments, TMB status can correlate with smoking status. In particular, subjects who currently or formerly smoke (d) often have more genetic alterations, e.g., missense mutations, than subjects who never smoke (d).

A tumor with a high TMB can also have a high neoantigen load. As used herein, the term "neoantigen" refers to a newly formed antigen that has not been previously recognized by the immune system. A neoantigen can be a protein or peptide that is recognized as foreign (or non-self) by the immune system. Transcription of a gene in the tumor genome harboring a somatic mutation results in mutated mRNA that, when translated, gives rise to a mutated protein, which is then processed and transported to the ER lumen and binds to MHC class I complex, facilitating T-cell recognition of the neoantigen. Neoantigen recognition can promote T-cell activation, clonal expansion, and differentiation into effector and memory T-cells.

The TMB status of a tumor can be used as a factor, alone or in combination with other factors, in determining whether a patient is likely to benefit from a particular anti-cancer agent or type of treatment or therapy, e.g., immuno-oncology agents, e.g., an anti-PD-1 antibody or antigen-binding portion thereof or an anti-PD-L1 antibody or antigen-binding portion thereof. In one embodiment, a high TMB status (or a high TMB) indicates an enhanced likelihood of benefit from immuno-oncology and, thus, can be used to identify patients more likely to benefit from therapy of an anti-PD-1 antibody or antigen-binding portion thereof. As used herein, the term "benefit from therapy" refers to an improvement in one or more of overall survival, progression-free survival, partial response, complete response, and overall response rate and can also include a reduction in tumor growth or size, a decrease in severity of disease symptoms, an increase in frequency and duration of disease symptom-free periods, or a prevention of impairment or disability due to the disease affliction.

The term "measuring" or "measured" or "measurement" when referring to TMB status or mutation status of a gene means determining a measurable quantity of somatic mutations in a biological sample of the subject. It will be appreciated that measuring can be performed by sequencing nucleic acids, e.g., cDNA, mRNA, exoRNA, ctDNA, and cfDNA, in the sample. The measuring is performed on a subject's sample and/or a reference sample or samples and can, for example, be detected de novo or correspond to a previous determination. The measuring can be performed, for example, using PCR methods, qPCR methods, Sanger sequencing methods, genomic profiling methods (including comprehensive gene panels), exome sequencing methods, genome sequencing methods, and/or any other method disclosed herein, as is known to a person of skill in the art. In some embodiments, the measuring identifies a genomic alteration in the sequenced nucleic acids. The genomic (or gene) profiling methods can involve panels of a predetermined set of genes, e.g., 150-500 genes, and in some instances the genomic alterations evaluated in the panel of genes are correlated with total somatic mutations evaluated.

The term "genomic alteration" as used herein refers to a change (or mutation) in the nucleotide sequence of the genome of a tumor, which change is not present in the germline nucleotide sequence, and which in some embodiments is a non-synonymous mutation including, but not limited to, a base pair substitution, a base pair insertion, a base pair deletion, a copy number alteration (CNA), a gene rearrangement, and any combination thereof. In a particular embodiment, the genomic alterations measured in the biological sample are missense mutations.

The term "biological sample" as used herein refers to biological material isolated from a subject. The biological sample can contain any biological material suitable for determining TMB, for example, by sequencing nucleic acids in the tumor (or circulating tumor cells) and identifying a genomic alteration in the sequenced nucleic acids. The biological sample can be any suitable biological tissue or fluid such as, for example, tumor tissue, blood, blood plasma, and serum. In one embodiment, the sample is a tumor tissue biopsy, e.g., a formalin-fixed, paraffin-embedded tumor tissue or a fresh-frozen tumor tissue or the like. In another embodiment, the biological sample is a liquid biopsy that, in some embodiments, comprises one or more of blood, serum, plasma, circulating tumor cells, exoRNA, ctDNA, and cfDNA.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "once about every week," "once about every two weeks," or any other similar dosing interval terms as used herein mean approximate numbers. "Once about every week" can include every seven days±one day, i.e., every six days to every eight days. "Once about every two weeks" can include every fourteen days±three days, i.e., every eleven days to every seventeen days. Similar approximations apply, for example, to once about every three weeks, once about every four weeks, once about every five weeks, once about every six weeks and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

The term "weight based dose" as referred to herein means that a dose that is administered to a patient is calculated based on the weight of the patient. For example, when a patient with 60 kg body weight requires 3 mg/kg of an anti-PD-1 antibody, one can calculate and use the appropriate amount of the anti-PD-1 antibody (i.e., 180 mg) for administration.

The use of the term "fixed dose" with regard to a method of the disclosure means that two or more different antibodies in a single composition (e.g., anti-PD-1 antibody and a second antibody) are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody (e.g., anti-PD-1 antibody) to mg second antibody. For example, the 3:1 ratio of an anti-PD-1 antibody and an second antibody can mean that a vial can contain about 240 mg of the anti-PD-1 antibody and 80 mg of the second antibody or about 3 mg/ml of the anti-PD-1 antibody and 1 mg/ml of the second antibody.

The use of the term "flat dose" with regard to the methods and dosages of the disclosure means a dose that is administered to a patient without regard for the weight or body surface area (BSA) of the patient. The flat dose is therefore not provided as a mg/kg dose, but rather as an absolute amount of the agent (e.g., the anti-PD-1 antibody). For example, a 60 kg person and a 100 kg person would receive the same dose of an antibody (e.g., 240 mg of an anti-PD-1 antibody).

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

Methods of the Disclosure

This disclosure provides for treating a subject afflicted with a tumor comprising (i) determining a mutation status of an STK11 gene in the subject; and (ii) administering to the subject an antibody or an antigen-binding portion thereof that binds specifically to a Programmed Death-1 (PD-1) receptor and inhibits PD-1 activity ("anti-PD-1 antibody"). In certain aspects, the subject afflicted with a tumor (e.g., NSCLC, e.g., non-squamous NSCLC) is administered an anti-PD-1 antibody if the STK11 gene is wild-type. In certain aspects, the disclosure relates to methods for treating a subject afflicted with a tumor (e.g., NSCLC, e.g., non-squamous NSCLC) comprising administering to the subject an anti-PD-1 antibody, wherein the subject is identified as having a wild-type STK11 gene. In some aspects, the disclosure relates to methods for identifying a subject afflicted with a tumor (e.g., NSCLC, e.g., non-squamous NSCLC) suitable for an anti-PD-1 antibody treatment comprising (i) determining a mutation status of an STK11 gene in the subject; and (ii) administering to the subject anti-PD-1 antibody if the STK11 gene is wild-type.

This disclosure further provides for treating a subject afflicted with a tumor comprising (i) determining a mutation status of an STK11 gene in the subject; and (ii) administering to the subject an antibody or an antigen-binding portion thereof that binds specifically to a Programmed Death-Ligand 1 (PD-L1) and inhibits PD-1 activity ("anti-PD-L1 antibody"). In certain aspects, the subject afflicted with a tumor (e.g., NSCLC, e.g., non-squamous NSCLC) is administered an anti-PD-L1 antibody if the STK11 gene is wild-type. In certain aspects, the disclosure relates to methods for treating a subject afflicted with a tumor (e.g., NSCLC, e.g., non-squamous NSCLC) comprising administering to the subject an anti-PD-L1 antibody, wherein the subject is identified as having a wild-type STK11 gene. In some aspects, the disclosure relates to methods for identifying a subject afflicted with a tumor (e.g., NSCLC, e.g., non-squamous NSCLC) suitable for an anti-PD-L1 antibody treatment comprising (i) determining a mutation status of an STK11 gene in the subject; and (ii) administering to the subject anti-PD-L1 antibody if the STK11 gene is wild-type.

In other aspects, the present disclosure relates to methods for treating a subject afflicted with a tumor (e.g., NSCLC, e.g., non-squamous NSCLC) comprising (i) determining a mutation status of an STK11 gene in the subject; and (ii) identifying the subject as not being eligible for the anti-PD-1 antibody administration, e.g., not administering to the subject an anti-PD-1 antibody or terminating or augmenting an anti-PD-1 antibody therapy, e.g., administering an anti-cancer agent that is not a PD-1 antagonist, if the STK11 gene comprises a non-synonymous mutation. Other aspects of the present disclosure relate to methods of identifying a subject afflicted with a tumor (e.g., NSCLC, e.g., non-squamous NSCLC) that is not suitable for an anti-PD-1 antibody treatment comprising (i) determining a mutation status of an STK11 gene in the subject; and (ii) identifying the subject as not being eligible for the anti-PD-1 antibody administration, e.g., not administering to the subject an anti-PD-1 antibody or terminating or augmenting an anti-PD-1 antibody therapy, e.g., administering an anti-cancer agent that is not a PD-1 antagonist, if the STK11 gene comprises a non-synonymous mutation.

In other aspects, the present disclosure relates to methods for treating a subject afflicted with a tumor (e.g., NSCLC, e.g., non-squamous NSCLC) comprising (i) determining a mutation status of an STK11 gene in the subject; and (ii) identifying the subject as not being eligible for the anti-PD-L1 antibody administration, e.g., not administering to the subject an anti-PD-L1 antibody or terminating or augmenting an anti-PD-L1 antibody therapy, e.g., administering an anti-cancer agent that is not a PD-L1 antagonist, if the STK11 gene comprises a non-synonymous mutation. Other aspects of the present disclosure relate to methods of identifying a subject afflicted with a tumor (e.g., NSCLC, e.g., non-squamous NSCLC) that is not suitable for an anti-PD-L1 antibody treatment comprising (i) determining a mutation status of an STK11 gene in the subject; and (ii) identifying the subject as not being eligible for the anti-PD-L1 antibody administration, e.g., not administering to the subject an anti-PD-L1 antibody or terminating or augmenting an anti-PD-1 antibody therapy, e.g., administering an anti-cancer agent that is not a PD-L1 antagonist, if the STK11 gene comprises a non-synonymous mutation.

In other aspects, the disclosure relates to methods for treating a subject afflicted with a tumor comprising (i) determining a mutation status of marker gene in the subject; and (ii) administering to the subject an anti-PD-1 antibody if the marker gene is mutated; wherein the marker gene is selected from the group consisting of TP53, CDKN2A, PTPND, CUBN, HERC1, and any combination thereof. Other aspects of the present disclosure relate to methods for treating a subject afflicted with a tumor comprising administering to the subject an anti-PD-1 antibody, wherein the subject is identified as having a mutated marker gene, wherein the marker gene is selected from the group consisting of TP53, CDKN2A, PTPND, CUBN, HERC1, and any combination thereof. Still other aspects of the present disclosure relate to methods for identifying a subject afflicted with a tumor suitable for an anti-PD-1 antibody treatment comprising (i) determining a mutation status of a marker gene in the subject; and (ii) administering to the subject anti-PD-1 antibody if the marker gene is mutated; wherein the marker gene is selected from the group consisting of TP53, CDKN2A, PTPND, CUBN, HERC1, and any combination thereof.

In other aspects, the disclosure relates to methods for treating a subject afflicted with a tumor comprising (i) determining a mutation status of marker gene in the subject; and (ii) administering to the subject an anti-PD-L1 antibody if the marker gene is mutated; wherein the marker gene is selected from the group consisting of TP53, CDKN2A, PTPND, CUBN, HERC1, and any combination thereof. Other aspects of the present disclosure relate to methods for treating a subject afflicted with a tumor comprising administering to the subject an anti-PD-L1 antibody, wherein the subject is identified as having a mutated marker gene, wherein the marker gene is selected from the group consisting of TP53, CDKN2A, PTPND, CUBN, HERC1, and any combination thereof. Still other aspects of the present disclosure relate to methods for identifying a subject afflicted with a tumor suitable for an anti-PD-L1 antibody treatment comprising (i) determining a mutation status of a marker gene in the subject; and (ii) administering to the subject anti-PD-L1 antibody if the marker gene is mutated; wherein the marker gene is selected from the group consisting of TP53, CDKN2A, PTPND, CUBN, HERC1, and any combination thereof.

In certain embodiments, the subject carries a mutated variant of TP53. In certain embodiments, the subject carries a mutated variant of CDKN2A. In certain embodiments, the subject carries a mutated variant of PTPND. In certain embodiments, the subject carries a mutated variant of CUBN. In certain embodiments, the subject carries a mutated variant of HERC1. In certain embodiments, the subject carries a mutated variant of PTPND and CUBN. In certain embodiments, the subject carries a mutated variant of PTPND and HERC1. In certain embodiments, the subject carries a mutated variant of CUBN and HERC1. In certain embodiments, the subject carries a mutated variant of PTPND, CUBN, and HERC1.

In certain embodiments the wild-type STK11 comprises one or more synonymous mutations, wherein the mutation in the genomic sequence does not affect the sequence of the expressed protein. In certain embodiments the mutated STK11 comprises a non-synonymous mutation. In some embodiments, the mutated STK11 comprises a nonsense mutation. In some embodiments, the mutated STK11 comprises a frameshift mutation. In some embodiments, the mutated STK11 comprises a splicing mutation. In some embodiments, the mutated STK11 is expressed as an mRNA and ultimately a protein. In some embodiments, the mutated STK11 protein is functional. In other embodiments, the mutated STK11 protein has reduced activity. In other embodiments, the mutated STK11 protein is non-functional.

In certain embodiments the mutated TP53 comprises a non-synonymous mutation. In some embodiments, the mutated TP53 comprises a nonsense mutation. In some embodiments, the mutated TP53 comprises a frameshift mutation. In some embodiments, the mutated TP53 comprises a splicing mutation. In some embodiments, the mutated TP53 is expressed as an mRNA and ultimately a protein. In some embodiments, the mutated TP53 protein is functional. In other embodiments, the mutated TP53 protein has reduced activity. In other embodiments, the mutated TP53 protein is non-functional.

In certain embodiments the mutated CDKN2A comprises a non-synonymous mutation. In some embodiments, the mutated CDKN2A comprises a nonsense mutation. In some embodiments, the mutated CDKN2A comprises a frameshift mutation. In some embodiments, the mutated CDKN2A comprises a splicing mutation. In some embodiments, the mutated CDKN2A is expressed as an mRNA and ultimately a protein. In some embodiments, the mutated CDKN2A protein is functional. In other embodiments, the mutated CDKN2A protein has reduced activity. In other embodiments, the mutated CDKN2A protein is non-functional.

In certain embodiments the mutated PTPND comprises a non-synonymous mutation. In some embodiments, the mutated PTPND comprises a nonsense mutation. In some embodiments, the mutated PTPND comprises a frameshift mutation. In some embodiments, the mutated PTPND comprises a splicing mutation. In some embodiments, the mutated PTPND is expressed as an mRNA and ultimately a protein. In some embodiments, the mutated PTPND protein is functional. In other embodiments, the mutated PTPND protein has reduced activity. In other embodiments, the mutated PTPND protein is non-functional.

In certain embodiments the mutated CUBN comprises a non-synonymous mutation. In some embodiments, the mutated CUBN comprises a nonsense mutation. In some embodiments, the mutated CUBN comprises a frameshift mutation. In some embodiments, the mutated CUBN comprises a splicing mutation. In some embodiments, the mutated CUBN is expressed as an mRNA and ultimately a protein. In some embodiments, the mutated CUBN protein is functional. In other embodiments, the mutated CUBN protein has reduced activity. In other embodiments, the mutated CUBN protein is non-functional.

In certain embodiments the mutated HERC1 comprises a non-synonymous mutation. In some embodiments, the mutated HERC1 comprises a nonsense mutation. In some embodiments, the mutated HERC1 comprises a frameshift mutation. In some embodiments, the mutated HERC1 comprises a splicing mutation. In some embodiments, the mutated HERC1 is expressed as an mRNA and ultimately a protein. In some embodiments, the mutated HERC1 protein is functional. In other embodiments, the mutated HERC1 protein has reduced activity. In other embodiments, the mutated HERC1 protein is non-functional.

In certain embodiments, the tumor is derived from a lung cancer. In some embodiments, the tumor is derived from a NSCLC. In some embodiments, the subject is a human patient. In certain embodiments, the subject is a chemotherapy-naïve patient (e.g., a patient who has not previously received any chemotherapy). In other embodiments, the subject for the present combination therapy has received another cancer therapy (e.g., a chemotherapy), but is resistant or refractory to such another cancer therapy.

In certain embodiments, the disclosure provides for treating a subject afflicted with a squamous NSCLC comprising (i) determining a mutation status of an STK11 gene in the subject; and (ii) administering to the subject an anti-PD-1 antibody (or an anti-PD-L1 antibody) if the STK11 gene is mutated. In certain aspects, the disclosure relates to methods for treating a subject afflicted with a squamous NSCLC comprising administering to the subject an anti-PD-1 antibody, wherein the subject is identified as having a mutated STK11 gene. In some aspects, the disclosure relates to methods for identifying a subject afflicted with a squamous NSCLC suitable for an anti-PD-1 antibody treatment comprising (i) determining a mutation status of an STK11 gene in the subject; and (ii) administering to the subject anti-PD-1 antibody if the STK11 gene is mutated.

In other aspects, the present disclosure relates to methods for treating a subject afflicted with a squamous NSCLC comprising (i) determining a mutation status of an STK11 gene in the subject; and (ii) administering to the subject an anti-PD-1 antibody (or an anti-PD-L1 antibody) or terminating or augmenting an anti-PD-1 antibody (or an anti-PD-L1 antibody) therapy if the STK11 gene comprises a non-synonymous mutation.

In certain embodiments, the therapy of the present disclosure (e.g., administration of an anti-PD-1 antibody or an anti-PD-L1 antibody) effectively increases the duration of survival of the subject. In some embodiments, the anti-PD-1 antibody therapy of the present disclosure increases the progression-free survival of the subject. In certain embodiments, the anti-PD-1 antibody therapy of the present disclosure increases the progression-free survival of the subject in comparison to standard-of-care therapies. After the administration of an anti-PD-1 antibody therapy, the subject having a tumor can exhibit an overall survival of at least about 10 months, at least about 11 months, at least about 12 months, at least about 13 months, at least about 14 months at least about 15 months, at least about 16 months, at least about 17 months, at least about 18 months, at least about 19 months, at least about 20 months, at least about 21 months, at least about 22 months, at least about 23 months, at least about 2 years, at least about 3 years, at least about 4 years, or at least about 5 years after the administration.

In other embodiments, the duration of survival or the overall survival of the subject is increased by at least about 1 month, at least about 2 months, at least about 3 months, at least about 4 months, at least about 6 months, or at least about 1 year when compared to another subject treated with only a standard-of-care therapy (e.g., docetaxel) or a different dosing schedule of the therapy. For example, the duration of survival or the overall survival of the subject treated with an anti-PD-1 antibody disclosed herein is increased by at least about 5%, at least about 10%, at least about 15%, at least about 20%, at least about 25%, at least about 30%, at least about 40%, at least about 50% or at least about 75% when compared to another subject treated with only a standard-of-care therapy (e.g., docetaxel) or a different dosing schedule of the combination therapy.

In certain embodiments, the therapy of the present disclosure effectively increases the duration of progression free survival of the subject. In some embodiments, the subject exhibits a progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years.

In some embodiments, the administering of the anti-PD-1 antibody treats the tumor. In certain embodiments, the administering reduces the size of the tumor. In one embodiment, the size of the tumor is reduced by at least about 10%, about 20%, about 30%, about 40%, about 50%, about 60%, about 70%, about 80%, about 90%, about 95%, or about 100% compared to the tumor size prior to the administration. In other embodiments, the subject exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the initial administration. In some embodiments, the subject exhibits stable disease after the administration. In some embodiments, the subject exhibits a partial response after the administration. In some embodiments, the subject exhibits a complete response after the administration. In some embodiments, the subject exhibits an improved objective response rate (ORR) after the administration as compared to a subject treated with a standard of care treatment.

PD-L1 Expression

In certain embodiments, the subject has tumor cells that are PD-L1+. In certain embodiments, the subject has cancer cells that are PD-L1−. In some embodiments, the subject never smoked. In certain embodiments, the subject formerly smoked. In one embodiments, the subject currently smokes. In certain embodiments, the subject has cancer cells that are squamous. In certain embodiments, the subject has cancer cells that are non-squamous.

In some embodiments, the tumor exhibits a diffuse pattern of PD-L1 expression. In some embodiments, the diffuse pattern of PD-L1 expression is characterized by a PD-L1 H-score of from about 60 to about 500, from about 70 to about 490, from about 80 to about 480, from about 90 to about 470, from about 100 to about 460, from about 110 to about 450, from about 120 to about 440, from about 130 to about 430, from about 140 to about 420, from about 150 to about 410, from about 160 to about 400, from about 170 to about 390, from about 180 to about 380, from about 190 to about 370, from about 200 to about 360, from about 20 to about 350, from about 200 to about 340, from about 200 to about 330, from about 200 to about 320, from about 200 to about 310, or from about 200 to about 300. In certain embodiments, the diffuse pattern of PD-L1 expression is characterized by a PD-L1 H-score of at least about 60, at least about 70, at least about 80, at least about 90, at least about 100, at least about 110, at least about 120, at least about 130, at least about 140, at least about 150, at least about 160, at least about 170, at least about 180, at least about 190, at least about 200, at least about 210, at least about 220, at least about 225, at least about 230, at least about 240, at least about 250, at least about 260, at least about 270, at least about 275, at least about 280, at least about 290, or at least about 300. In certain embodiments, the diffuse pattern of PD-L1 expression is characterized by a PD-L1 H-score of at least about 200. In other embodiments, the diffuse pattern of PD-L1 expression is characterized by a PD-L1 H-score of at least about 240. In certain embodiments, the diffuse pattern of PD-L1 expression is characterized by a PD-L1 H-score of at least about 260.

In some embodiments, the tumor exhibits a heterogeneous pattern of PD-L1 expression. In some embodiments, the heterogeneous pattern of PD-L1 expression is characterized by a PD-L1 H-score of from about 1 to about 50, from about 5 to about 45, from about 10 to about 40, or from about 15 to about 35, and wherein the PD-L1 expression is restricted to one or more distinct portions of the tumor. In some embodiments, the heterogeneous pattern of PD-L1 expression is characterized by a PD-L1 H-score of at least about 5, at least about 10, at least about 15, at least about 20, at least about 25, at least about 30, at least about 35, or at least about 40. In one embodiment, the heterogeneous pattern of PD-L1 expression is characterized by a PD-L1 H-score of at least about 15. In another embodiment, the heterogeneous pattern of PD-L1 expression is characterized by a PD-L1 H-score of at least about 20. In some embodiments, the heterogeneous pattern of PD-L1 expression is characterized by a portion of the tumor comprising at least 10, at least 20, at least 30, at least 40, at least 50, at least 60, at least 70, at least 80, at least 90, at least 100, at least 150, or at least 150 expressing PD-L1. In certain embodiments, at least about 30%, at least about 40%, at least about 50%, at least about 60%, at least about 70%, at least about 80%, at least about 90%, at least about 95%, or about 100% of the cells within the portion of the tumor express PD-L1.

In some embodiments, the tumor exhibits PD-L1 expression at the tumor-stroma interface. In some embodiments, the tumor-stroma interface PD-L1 expression is characterized by expression of PD-L1 by tumor cells adjacent (e.g., with in about 1 cell diameter, about 2 cell diameters, about 3 cell diameters, about 4 cell diameters, about 5 cell diameters, about 6 cell diameters, about 7 cell diameters, about 8 cell diameters, about 9 cell diameters, or about 10 cell diameters) of the stroma. In certain embodiments, the tumor-stroma interface PD-L1 expression is characterized by PD-L1 expression on the surface of the tumor.

The PD-L1 expression status of a tumor in a subject can be measured prior to administering any composition or utilizing any method disclosed herein. In one embodiment, the PD-L1 expression level of a tumor is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100%. In another embodiment, the PD-L1 status of a tumor is at least about 1%. In other embodiments, the PD-L1 status of the subject is at least about 5%. In a certain embodiment, the PD-L1 status of a tumor is at least about 10%. In a one embodiment, the PD-L1 status of the tumor is at least about 25%. In a particular embodiment, the PD-L1 status of the tumor is at least about 50%.

In some embodiments, the method of the present disclosure comprises (i) determining a mutation status of an STK11 gene in the subject afflicted with a tumor (e.g., NSCLC, e.g., non-squamous NSCLC); (ii) detecting PD-L1 expression in the tumor; and (iii) administering to the subject an anti-PD-1 antibody if the STK11 gene is wild-type and if the PD-L1 expression is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100%. In some embodiments, the method of the present disclosure comprises (i) determining a mutation status of an STK11 gene in the subject afflicted with a tumor (e.g., NSCLC, e.g., non-squamous NSCLC); (ii) detecting PD-L1 expression in the tumor; and (iii) administering to the subject an anti-PD-1 antibody if the STK11 gene is wild-type and if the PD-L1 expression is at least about 15%. In some embodiments, the method of the present disclosure comprises (i) determining a mutation status of an STK11 gene in the subject afflicted with a tumor (e.g., NSCLC, e.g., non-squamous NSCLC); (ii) detecting PD-L1 expression in the tumor; and (iii) administering to the subject an anti-PD-1 antibody if the STK11 gene is wild-type and if the PD-L1 expression is at least about 25%. In some embodiments, the method of the present disclosure comprises (i) determining a mutation status of an STK11 gene in the subject afflicted with a tumor (e.g., NSCLC, e.g., non-squamous NSCLC); (ii) detecting PD-L1 expression in the tumor; and (iii) administering to the subject an anti-PD-1 antibody if the STK11 gene is wild-type and if the PD-L1 expression is at least about 50%.

In some embodiments, the method of the present disclosure comprises (i) determining a mutation status of an STK11 gene in the subject afflicted with a tumor (e.g., NSCLC, e.g., non-squamous NSCLC); (ii) detecting PD-L1 expression in the tumor; and (iii) identifying the subject as not being eligible for the anti-PD-1 antibody administration, e.g., not administering to the subject an anti-PD-1 antibody or terminating or augmenting an anti-PD-1 antibody therapy, e.g., administering an anti-cancer agent that is not a PD-1 antagonist, if the STK11 gene comprises a non-synonymous mutation and the tumor PD-L1 expression is less than about 50%. In some embodiments, the method of the present disclosure comprises (i) determining a mutation status of an STK11 gene in the subject afflicted with a tumor (e.g., NSCLC, e.g., non-squamous NSCLC); (ii) detecting PD-L1 expression in the tumor; and (iii) identifying the subject as not being eligible for the anti-PD-1 antibody administration, e.g., not administering to the subject an anti-PD-1 antibody or terminating or augmenting an anti-PD-1 antibody therapy, e.g., administering an anti-cancer agent that is not a PD-1 antagonist, if the STK11 gene comprises a non-synonymous mutation and the tumor PD-L1 expression is less than about 40%. In some embodiments, the method of the present disclosure comprises (i) determining a mutation status of an STK11 gene in the subject; (ii) detecting PD-L1 expression in the tumor afflicted with a tumor (e.g., NSCLC, e.g., non-squamous NSCLC); and (iii) identifying the subject as not being eligible for the anti-PD-1 antibody administration, e.g., not administering to the subject an anti-PD-1 antibody or terminating or augmenting an anti-PD-1 antibody therapy, e.g., administering an anti-cancer agent that is not a PD-1 antagonist, if the STK11 gene comprises a non-synonymous mutation and the tumor PD-L1 expression is less than about 30%. In some embodiments, the method of the present disclosure comprises (i) determining a mutation status of an STK11 gene in the subject; (ii) detecting PD-L1 expression in the tumor; and (iii) identifying the subject as not being eligible for the anti-PD-1 antibody administration, e.g., not administering to the subject an anti-PD-1 antibody or terminating or augmenting an anti-PD-1 antibody therapy, e.g., administering an anti-cancer agent that is not a PD-1 antagonist, if the STK11 gene comprises a non-synonymous mutation and the tumor PD-L1 expression is less than about 25%. In some embodiments, the method of the present disclosure comprises (i) determining a mutation status of an STK11 gene in the subject; (ii) detecting PD-L1 expression in the tumor; and (iii) identifying the subject as not being eligible for the anti-PD-1 antibody administration, e.g., not administering to the subject an anti-PD-1 antibody or terminating or augmenting an anti-PD-1 antibody therapy, e.g., administering an anti-cancer agent that is not a PD-1 antagonist, if the STK11 gene comprises a non-synonymous mutation and the tumor PD-L1 expression is less than about 20%. In some embodiments, the method of the present disclosure comprises (i) determining a mutation status of an STK11 gene in the subject; (ii) detecting PD-L1 expression in the tumor; and (iii) identifying the subject as not being eligible for the anti-PD-1 antibody administration, e.g., not administering to the subject an anti-PD-1 antibody or terminating or augmenting an anti-PD-1 antibody therapy, e.g., administering an anti-cancer agent that is not a PD-1 antagonist, if the STK11 gene comprises a non-synonymous mutation and the tumor PD-L1 expression is less than about 15%. In some embodiments, the method of the present disclosure comprises (i) determining a mutation status of an STK11 gene in the subject; (ii) detecting PD-L1 expression in the tumor; and (iii) identifying the subject as not being eligible for the anti-PD-1 antibody administration, e.g., not administering to the subject an anti-PD-1 antibody or terminating or augmenting an anti-PD-1 antibody therapy, e.g., administering an anti-cancer agent that is not a PD-1 antagonist, if the STK11 gene comprises a non-synonymous mutation and the tumor PD-L1 expression is less than about 10%. In some embodiments, the method of the present disclosure comprises (i) determining a mutation status of an STK11 gene in the subject; (ii) detecting PD-L1 expression in the tumor; and (iii) identifying the subject as not being eligible for the anti-PD-1 antibody administration, e.g., not administering to the subject an anti-PD-1 antibody or terminating or augmenting an anti-PD-1 antibody therapy, e.g., administering an anti-cancer agent that is not a PD-1 antagonist, if the STK11 gene comprises a non-synonymous mutation and the tumor PD-L1 expression is less than about 5%. In some embodiments, the method of the present disclosure comprises (i) determining a mutation status of an STK11 gene in the subject; (ii) detecting PD-L1 expression in the tumor; and (iii) identifying the subject as not being eligible for the anti-PD-1 antibody administration, e.g., not administering to the subject an anti-PD-1 antibody or terminating or augmenting an anti-PD-1 antibody therapy, e.g., administering an anti-cancer agent that is not a PD-1 antagonist, if the STK11 gene comprises a non-synonymous mutation and the tumor PD-L1 expression is less than about 3%. In some embodiments, the method of the present disclosure comprises (i) determining a mutation status of an STK11 gene in the subject; (ii) detecting PD-L1 expression in the tumor; and (iii) identifying the subject as not being eligible for the anti-PD-1 antibody administration, e.g., not administering to the subject an anti-PD-1 antibody or terminating or augmenting an anti-PD-1 antibody therapy, e.g., administering an anti-cancer agent that is not a PD-1 antagonist, if the STK11 gene comprises a non-synonymous mutation and the tumor PD-L1 expression is less than about 2%. In some embodiments, the method of the present disclosure comprises (i) determining a mutation status of an STK11 gene in the subject; (ii) detecting PD-L1 expression in the tumor; and (iii) identifying the subject as not being eligible for the anti-PD-1 antibody administration, e.g., not administering to the subject an anti-PD-1 antibody or terminating or augmenting an anti-PD-1 antibody therapy, e.g., administering an anti-cancer agent that is not a PD-1 antagonist, if the STK11 gene comprises a non-synonymous mutation and the tumor PD-L1 expression is less than about 1%.

In certain embodiments, the tumor can exhibit a high level of inflammation. Increased inflammation can be indicative of a diffuse PD-L1 expression pattern. Accordingly, high tumor inflammation can be indicative of responsiveness to an anti-PD-1 antibody therapy.

Methods of Detection

Certain aspects of the present disclosure relate to determining the mutational status of one or more marker genes, e.g., STK11, in a subject. Any methods known in the art can be used to determine whether a subject carries wild-type or mutant variants of a marker gene. In certain embodiments, the target marker gene is sequenced using any means available in the art, and the sequence of the marker gene is compared to the known sequence of the same marker gene in the art. In certain embodiments, the marker gene has a non-synonymous mutation. In some embodiments, the marker gene has a nonsense mutation. In some embodiments, the marker gene has a frameshift mutation. In some embodiments, the marker gene has a splicing mutation. In certain embodiments, the mutant marker gene is expressed. In other embodiments, the mutant marker gene is not expressed.

In some embodiments, the mutational status of the marker gene is determined by detecting the expression of the marker gene. In certain embodiments, the mutant variant of the target gene is not expressed, and a lack of the resulting mRNA and/or protein indicates the presence of the mutant variant. In certain embodiments, the mutational status of the marker gene is determined by sequencing the resulting mRNA and/or the resulting protein. In some embodiments, the mutational status of the marker gene is determined by immunohistochemistry directed to the resulting protein.

In some embodiments, the subject has one wild-type copy of the marker gene and one mutant copy of the marker gene. In some embodiment, the subject has two wild-type copies of the marker gene and no mutant copies of the marker gene. In some embodiments, the subject has two mutant copies of the marker gene and no copies of the wild-type marker gene. In some embodiments the two mutant copies of the marker gene are the same. In some embodiments, the subject has two different mutant copies of the marker gene.

Some aspects of the present disclosure relate to determining and/or measuring the expression level of one or more marker genes in the tumor of a subject. In order to assess the PD-L1 expression, in one embodiment, a test tissue sample can be obtained from the patient who is in need of the therapy. In another embodiment, the assessment of PD-L1 expression can be achieved without obtaining a test tissue sample. In some embodiments, selecting a suitable patient includes (i) optionally providing a test tissue sample obtained from a patient with cancer of the tissue, the test tissue sample comprising tumor cells and/or tumor-infiltrating inflammatory cells; and (ii) assessing the proportion of cells in the test tissue sample that express PD-L1 on the surface of the cells based on an assessment that the proportion of cells in the test tissue sample that express PD-L1 on the cell surface is higher than a predetermined threshold level.

In any of the methods comprising the measurement of PD-L1 expression in a test tissue sample, however, it should be understood that the step comprising the provision of a test tissue sample obtained from a patient is an optional step. It should also be understood that in certain embodiments the "measuring" or "assessing" step to identify, or determine the number or proportion of, cells in the test tissue sample that express PD-L1 (e.g., the expression of PD-L1 on the cell surface) is performed by a transformative method of assaying for PD-L1 expression, for example by performing a reverse transcriptase-polymerase chain reaction (RT-PCR) assay or an IHC assay. In certain other embodiments, no transformative step is involved and PD-L1 expression is assessed by, for example, reviewing a report of test results from a laboratory. In certain embodiments, the steps of the methods up to, and including, assessing PD-L1 expression provides an intermediate result that may be provided to a physician or other healthcare provider for use in selecting a suitable candidate for the anti-PD-1 antibody or anti-PD-L1 antibody therapy. In certain embodiments, the steps that provide the intermediate result is performed by a medical practitioner or someone acting under the direction of a medical practitioner. In other embodiments, these steps are performed by an independent laboratory or by an independent person such as a laboratory technician.

In certain embodiments of any of the present methods, the proportion of cells that express PD-L1 is assessed by performing an assay to determine the presence of PD-L1 RNA. In further embodiments, the presence of PD-L1 RNA is determined by RT-PCR, in situ hybridization or RNase protection. In other embodiments, the proportion of cells that express PD-L1 is assessed by performing an assay to determine the presence of PD-L1 polypeptide. In further embodiments, the presence of PD-L1 polypeptide is determined by immunohistochemistry (IHC), enzyme-linked immunosorbent assay (ELISA), in vivo imaging, or flow cytometry. In some embodiments, PD-L1 expression is assayed by IHC. In other embodiments of all of these methods, cell surface expression of PD-L1 is assayed using, e.g., IHC or in vivo imaging.

Imaging techniques have provided important tools in cancer research and treatment. Recent developments in molecular imaging systems, including positron emission tomography (PET), single-photon emission computed tomography (SPECT), fluorescence reflectance imaging (FRI), fluorescence-mediated tomography (FMT), bioluminescence imaging (BLI), laser-scanning confocal microscopy (LSCM) and multiphoton microscopy (MPM), will likely herald even greater use of these techniques in cancer research. Some of these molecular imaging systems allow clinicians to not only see where a tumor is located in the body, but also to visualize the expression and activity of specific molecules, cells, and biological processes that influence tumor behavior and/or responsiveness to therapeutic drugs (Condeelis and Weissleder, "In vivo imaging in cancer," *Cold Spring Harb. Perspect. Biol.* 2 (12): a003848 (2010)). Antibody specificity, coupled with the sensitivity and resolution of PET, makes immunoPET imaging particularly attractive for monitoring and assaying expression of antigens in tissue samples (McCabe and Wu, "Positive progress in immunoPET—not just a coincidence," *Cancer Biother. Radiopharm.* 25 (3): 253-61 (2010); Olafsen et al., "ImmunoPET imaging of B-cell lymphoma using 124I-anti-CD20 scFv dimers (diabodies)," *Protein Eng. Des. Sel.* 23 (4): 243-9 (2010)). In certain embodiments of any of the present methods, PD-L1 expression is assayed by immuno-PET imaging. In certain embodiments of any of the present methods, the proportion of cells in a test tissue sample that express PD-L1 is assessed by performing an assay to determine the presence of PD-L1 polypeptide on the surface of cells in the test tissue sample. In certain embodiments, the test tissue sample is a FFPE tissue sample. In other embodiments, the presence of PD-L1 polypeptide is determined by IHC assay. In further embodiments, the IHC assay is performed using an automated process. In some embodiments, the IHC assay is performed using an anti-PD-L1 monoclonal antibody to bind to the PD-L1 polypeptide.

In one embodiment of the present methods, an automated IHC method is used to assay the expression of PD-L1 on the surface of cells in FFPE tissue specimens. This disclosure provides methods for detecting the presence of human PD-L1 antigen in a test tissue sample, or quantifying the level of human PD-L1 antigen or the proportion of cells in the sample that express the antigen, which methods comprise contacting the test sample, and a negative control sample, with a monoclonal antibody that specifically binds to human PD-L1, under conditions that allow for formation of a complex between the antibody or portion thereof and human PD-L1. In certain embodiments, the test and control tissue samples are FFPE samples. The formation of a complex is then detected, wherein a difference in complex formation between the test sample and the negative control sample is indicative of the presence of human PD-L1 antigen in the sample. Various methods are used to quantify PD-L1 expression.

In a particular embodiment, the automated IHC method comprises: (a) deparaffinizing and rehydrating mounted tissue sections in an autostainer; (b) retrieving antigen using a decloaking chamber and pH 6 buffer, heated to 110° C. for 10 min; (c) setting up reagents on an autostainer; and (d) running the autostainer to include steps of neutralizing endogenous peroxidase in the tissue specimen; blocking non-specific protein-binding sites on the slides; incubating the slides with primary Ab; incubating with a postprimary blocking agent; incubating with NovoLink Polymer; adding a chromogen substrate and developing; and counterstaining with hematoxylin.

For assessing PD-L1 expression in tumor tissue samples, a pathologist examines the number of membrane PD-L1$^+$ tumor cells in each field under a microscope and mentally estimates the percentage of cells that are positive, then averages them to come to the final percentage. The different staining intensities are defined as 0/negative, 1+/weak, 2+/moderate, and 3+/strong. Typically, percentage values are first assigned to the 0 and 3+buckets, and then the intermediate 1+ and 2+intensities are considered. For highly heterogeneous tissues, the specimen is divided into zones, and each zone is scored separately and then combined into a single set of percentage values. The percentages of negative and positive cells for the different staining intensities are determined from each area and a median value is given to each zone. A final percentage value is given to the tissue for each staining intensity category: negative, 1+, 2+, and 3+. The sum of all staining intensities needs to be 100%. In one embodiment, the threshold number of cells that needs to be PD-L1 positive is at least about 100, at least about 125, at least about 150, at least about 175, or at least about 200 cells. In certain embodiments, the threshold number or cells that needs to be PD-L1 positive is at least about 100 cells.

Staining is also assessed in tumor-infiltrating inflammatory cells such as macrophages and lymphocytes. In most cases macrophages serve as an internal positive control since staining is observed in a large proportion of macrophages. While not required to stain with 3+intensity, an absence of staining of macrophages should be taken into account to rule out any technical failure. Macrophages and lymphocytes are assessed for plasma membrane staining and only recorded for all samples as being positive or negative for each cell category. Staining is also characterized according to an outside/inside tumor immune cell designation. "Inside" means the immune cell is within the tumor tissue and/or on the boundaries of the tumor region without being physically intercalated among the tumor cells. "Outside" means that there is no physical association with the tumor, the immune cells being found in the periphery associated with connective or any associated adjacent tissue.

In certain embodiments of these scoring methods, the samples are scored by two pathologists operating independently, and the scores are subsequently consolidated. In certain other embodiments, the identification of positive and negative cells is scored using appropriate software.

A histoscore, or "H-score," is used as a more quantitative measure of the IHC data. The histoscore is calculated as follows:

Histoscore=[(% tumor×1(low intensity))+(% tumor×2(medium intensity))+(% tumor×3(high intensity)]

To determine the histoscore, the pathologist estimates the percentage of stained cells in each intensity category within a specimen. Because expression of most biomarkers is heterogeneous the histoscore is a truer representation of the overall expression. The final histoscore range is 0 (no expression) to 300 (maximum expression).

An alternative means of quantifying PD-L1 expression in a test tissue sample IHC is to determine the adjusted inflammation score (AIS) score defined as the density of inflammation multiplied by the percent PD-L1 expression by tumor-infiltrating inflammatory cells (Taube et al., "Colocalization of inflammatory response with B7-h1 expression in human melanocytic lesions supports an adaptive resistance mechanism of immune escape," *Sci. Transl. Med.* 4 (127): 127ra37 (2012)).

Tumor Mutational Burden (TMB)

Other aspects of the present disclosure are directed to measuring TMB in a tumor tissue obtained from a subject. As a tumor grows, it accumulates somatic mutations not present in germline DNA. Tumor mutation burden (TMB) refers to the number of somatic mutations in a tumor's genome and/or the number of somatic mutations per area of the tumor genome (after taking into account germline variant DNA). The acquisition of somatic mutations and, thus, a higher TMB can be influenced by distinct mechanisms, such as exogenous mutagen exposure (e.g., tobacco smoking or UV light exposure) and DNA mismatch repair mutations (e.g., MSI in colorectal and esophageal cancers). In solid tumors, about 95% of mutations are single-base substitutions. (Vogelstein et al., Science (2013) 339:1546-1558.) A "non-synonymous mutation" herein refers to a nucleotide mutation that alters the amino acid sequence of a protein. Missense mutations and nonsense mutations can be both non-synonymous mutations. A "missense mutation" herein refers to a non-synonymous point mutation in which a single nucleotide change results in a codon that codes for a different amino acid. A "non-sense mutation" herein refers to a non-synonymous point mutation in which a codon is changed to a premature stop codon that leads to truncation of the resulting protein.

In one embodiment, somatic mutations can be expressed at the RNA and/or protein level, resulting in neoantigens (also referred to as neoepitopes). Neoantigens can influence an immune-mediated anti-tumor response. For example, neoantigen recognition can promote T-cell activation, clonal expansion, and differentiation into effector and memory T-cells.

As a tumor develops, early clonal mutations (or "trunk mutations") can be carried by most or all tumor cells, while late mutations (or "branch mutations") can occur in only a subset of tumor cells or regions. (Yap et al., Sci Tranl Med (2012) 4:1-5; Jamai-Hanjani et al., (2015) Clin Cancer Res 21:1258-1266.) As a result, neoantigens derived from clonal "trunk" mutations are more widespread in the tumor genome than "branch" mutations and, thus, can lead to a high number of T cells reactive against the clonal neoantigen. (McGranahan et al., (2016) 351:1463-1469.) Generally, tumors with a high TMB can also have a high neoantigen load, which can lead to high tumor immunogenicity and increased T-cell reactivity and anti-tumor response. As such, cancers with a high TMB can respond well to treatment with immune-therapies, e.g., an anti-PD-1 antibody or anti-PD-L1 antibody.

Advances in sequencing technologies allow for evaluation of the tumor's genomic mutation landscape. Any sequencing methods known to those of skill in the art can be used to sequence nucleic acids from the tumor genome (e.g., obtained from a biological sample from a subject afflicted with a tumor). In one embodiment, PCR or qPCR methods, Sanger sequencing methods, or next-generation sequencing methods (such as genomic profiling, exome sequencing, or genome sequencing) can be used to measure TMB. In some embodiments, the TMB status is measured using genomic profiling. Genomic profiling involves analyzing nucleic acids from tumor samples, including coding and non-coding regions, and can be performed using methods having integrated optimized nucleic acid selection, read alignment, and mutation calling. In some embodiments, gene profiling provides next generation sequencing (NGS)-based analysis of tumors that can be optimized on a cancer-by-cancer, gene-by-gene and/or site-by-site basis. Genome profiling can integrate the use of multiple, individually tuned, alignment methods or algorithms to optimize performance in sequencing methods, particularly in methods that rely on massively parallel sequencing of a large number of diverse genetic events in a large number of diverse genes. Genomic profiling provides for a comprehensive analysis of a subject's cancer genome, with clinical grade quality, and the output of the genetic analysis can be contextualized with relevant scientific and medical knowledge to increase the quality and efficiency of cancer therapy.

Genomic profiling involves a panel of a predefined set of genes comprising as few as five genes or as many as 1000 genes, about 25 genes to about 750 genes, about 100 genes to about 800 genes, about 150 genes to about 500 genes, about 200 genes to about 400 genes, about 250 genes to about 350 genes. In one embodiment, the genomic profile comprises at least 300 genes, at least 305 genes, at least 310 genes, at least 315 genes, at least 320 genes, at least 325 genes, at least 330 genes, at least 335 genes, at least 340 genes, at least 345 genes, at least 350 genes, at least 355 genes, at least 360 genes, at least 365 genes, at least 370 genes, at least 375 genes, at least 380 genes, at least 385 genes, at least 390 genes, at least 395 genes, or at least 400 genes. In another embodiment, the genomic profile comprises at least 325 genes. In a particular embodiment, the genomic profile comprises at least 315 cancer-related genes and introns in 28 genes (FOUNDATIONONE®) or the complete DNA coding sequence of 406 genes, introns in 31 genes with rearrangements, and the RNA sequence (cDNA) of 265 genes (FOUNDATIONONE® Heme). In another embodiment, the genomic profile comprises 26 genes and 1000 associated mutations (EXODX® Solid Tumor). In yet another embodiment, the genomic profile comprises 76 genes (Guardant360). In yet another embodiment, the genomic profile comprises 73 genes (Guardant360). In another embodiment, the genomic profile comprises 354 genes and introns in 28 genes for rearrangements (FOUN- DATIONONE® CDX™). In certain embodiments, the genomic profile is FOUNDATIONONE® F1CDx. In another embodiment, the genomic profile comprises 468 genes (MSK-IMPACT™). One or more genes can be added to the genome profile as more genes are identified to be related to oncology.

In yet another particular embodiment, the genomic profiling detects all mutation types, i.e., single nucleotide variants, insertions/deletions (indels), copy number variations, and rearrangements, e.g., translocations, expression, and epigenetic markers.

Comprehensive gene panels often contain predetermined genes selected based on the type of tumor to be analyzed. Accordingly, the genomic profile used to measure TMB status can be selected based on the type of tumor the subject has. In one embodiment, the genomic profile can include a set of genes particular to a solid tumor. In another embodiment, the genomic profile can include a set of genes particular to hematologic malignancies and sarcomas.

In one embodiment, the genomic profile comprises one or more genes selected from the group consisting of ABL1, BRAF, CHEK1, FANCC, GATA3, JAK2, MITE, PDCDILG2, RBM10, STAT4, ABL2, BRCA1, CHEK2, FANCD2, GATA4, JAK3, MLH1, PDGFRA, RET, STK11, ACVR1B, BRCA2, CIC, FANCE, GATA6, JUN, MPL, PDGFRB, RICTOR, SUFU, AKT1, BRD4, CREBBP, FANCE, GID4 ((17orf39), KAT6A (MYST3), MRE11A, PDK1, RNF43, SYK, AKT2, BRIP1, CRKL, FANCG, GLI1, KDM5A, MSH2, PIK3C2B, ROS1, TAF1, AKT3, BTG1, CRLF2, FANCL, GNA11, KDM5C, MSH6, PIK3CA, RPTOR, TBX3, ALK, BTK, CSF1R, FAS, GNA13, KDM6A, MTOR, PIK3CB, RUNX1, TERC, AMER1 (FAM123B), C11orf30 (EMSY), CTCF, FAT1, GNAQ, KDR, MUTYH, PIK3CG, RUNX1T1, TERT (promoter only), APC, CARD11, CTNNA1, FBXW7, GNAS, KEAP1, MYC, PIK3R1, SDHA, TET2, AR, CBFB, CTNNB1, FGF10, GPR124, KEL, MYCL (MYCL1), PIK3R2, SDHB, TGFBR2, ARAF, CBL, CUL3, FGF14, GRIN2A, KIT, MYCN, PLCG2, SDHC, TNFAIP3, ARFRP1, CCND1, CYLD, FGF19, GRM3, KLHL6, MYD88, PMS2, SDHD, TNFRSF14, ARID1A, COND2, DAXX, FGF23, GSK3B, KMT2A (MLL), NF1, POLD1, SETD2, TOP1, ARID1B, CCND3, DDR2, FGF3, H3F3A, KMT2C (MLL3), NF2, POLE, SF3B1, TOP2A, ARID2, CCNE1, DICER1, FGF4, HGF, KMT2D (MLL2), NFE2L2, PPP2R1A, SLIT2, TP53, ASXL1, CD274, DNMT3A, FGF6, HNF1A, KRAS, NFKBIA, PRDM1, SMAD2, TSC1, ATM, CD79A, DOT1L, FGFR1, HRAS, LMO1, NKX2-1, PREX2, SMAD3, TSC2, ATR, CD79B, EGFR, FGFR2, HSD3B1, LRP1B, NOTCH1, PRKAR1A, SMAD4, TSHR, ATRX, CDC73, EP300, FGFR3, HSP90AAI, LYN, NOTCH2, PRKC1, SMARCA4, U2AF1, AURKA, CDH1, EPHA3, FGFR4, IDH1, LZTR1, NOTCH3, PRKDC, SMARCB1, VEGFA, AURKB, CDK12, EPHA5, FH, IDH2, MAGI2, NPM1, PRSS8, SMO, VHL, AXIN1, CDK4, EPHA7, FLCN, IGF1R, MAP2K1, NRAS, PTCH1, SNCA1P, WISP3, AXL, CDK6, EPHB1, FLT1, IGF2, MAP2K2, NSD1, PTEN, SOCS1, WT1, BAP1, CDK8, ERBB2, FLT3, IKBKE, MAP2K4, NTRK1, PTPN11, SOX10, XPO1, BARD1, CDKN1A, ERBB3, FLT4, IKZF1, MAP3K1, NTRK2, QK1, SOX2, ZBTB2, BCL2, CDKN1B, ERBB4, FOXL2, IL7R, MCLI, NTRK3, RAC1, SOX9, ZNF217, BCL2L1, CDKN2A, ERG, FOXP1, INHBA, MDM2, NUP93, RAD50, SPEN, ZNF703, BCL2L2, CDKN2B, ERRF11, FRS2, INPP4B, MDM4, PAK3, RAD51, SPOP, BCL6, CDKN2C, ESR1, FUBP1, IRF2, MED12, PALB2, RAF1, SPTA1, BCOR, CEBPA, EZH2, GABRA6, IRF4, MEF2B, PARK2, RANBP2, SRC, BCORL1, CHD2, FAM46C, GATA1, IRS2, MEN1, PAX5, RARA, STAG2, BLM, CHD4, FANCA, GATA2, JAKI, MET, PBRM1, RB1, STAT3, and any combination thereof. In other embodiments, the TMB analysis further comprises identifying a genomic alteration in one or more of ETV4, TMPRSS2, ETV5, BCR, ETV1, ETV6, and MYB. In other embodiments, the mutation status of SKT11 gene can be assessed as part of the TMB analysis or as described above.

In one embodiment, TMB status based on genomic profiling is highly correlated with TMB status based on whole-exome or whole-genome sequencing.

TMB can be measured using a tissue biopsy sample or, alternatively, ctDNA and/or a liquid biopsy sample. ctDNA can be used to measure TMB status according to whole-exome or whole-genome sequencing or genomic profiling using available methodologies, e.g., GRAIL, Inc.

TMB status can be used alone or in combination with other factors as a means to predict a tumor's response to therapy and, in particular, treatment with an immuno-oncology agent, such as an anti-PD-1 antibody or an anti-PD-L1 antibody. In some embodiments, only the TMB status of a tumor is used to identify patients with a tumor more likely to respond to therapy with an anti-PD-1 antibody or an anti-PD-L1 antibody. In other embodiments, the PD-L1 status and TMB status is used to identify patients with a tumor more likely to respond to therapy with an anti-PD-1 antibody or an anti-PD-L1 antibody.

In some embodiments, the methods of the present disclosure further comprise measuring the TMB status of the subject prior to administering the anti-PD-1 antibody. In certain embodiments, the methods comprise administering an anti-PD-1 antibody to a subject who carries wild-type STK11 and has a high TMB status. In other embodiments, the methods comprise not administering to the subject an anti-PD-1 antibody or terminating or augmenting an anti-PD-1 antibody therapy if the subject carries a mutant variant of STK11 and the subject has a high TMB status. In some embodiments, the methods of the present disclosure further comprise measuring the TMB status of the subject prior to administering the anti-PD-1 antibody. In certain embodiments, the methods comprise administering an anti-PD-1 antibody to a subject who carries wild-type STK11 and has a medium TMB status. In other embodiments, the methods comprise not administering to the subject an anti-PD-1 antibody or terminating or augmenting an anti-PD-1 antibody therapy if the subject carries a mutant variant of STK11 and the subject has a medium TMB status. In other embodiments, the methods comprise not administering to the subject an anti-PD-1 antibody or terminating or augmenting an anti-PD-1 antibody therapy if the subject carries a mutant variant of STK11 and the subject has a low TMB status.

FOUNDATIONONE® Assay

The FOUNDATIONONE® assay is comprehensive genomic profiling assay for solid tumors, including but not limited to solid tumors of the lung, colon, and breast, melanoma, and ovarian cancer. The FOUNDATIONONE® assay uses a hybrid-capture, next-generation sequencing test to identify genomic alterations (base substitutions, insertions and deletions, copy number alterations, and rearrangements) and select genomic signatures (e.g., TMB and microsatellite instability). The assay covers 322 unique genes, including the entire coding region of 315 cancer-related genes, and selected introns from 28 genes. The full list of FOUNDATIONONE® assay genes is provided in Tables 1 and 2. See FOUNDATIONONE: Technical Specifications, Foundation Medicine, Inc., available at FoundationMedicine.com, last visited Mar. 16, 2018, which is incorporated by reference herein in its entirety.

TABLE 1

List of genes wherein entire coding sequences are assayed in the FOUNDATIONONE ® assay.

| | | | | | | | | | |
|---|---|---|---|---|---|---|---|---|---|
| ABL1 | BRAF | CHEK1 | FANCC | GATA3 | JAK2 | MITF | PDCD1LG2 (PD-L2) | RBM10 | STAT4 |
| ABL2 | BRCA1 | CHEK2 | FANCD2 | GATA4 | JAK3 | MLH1 | PDGFRA | RET | STK11 |
| ACVR1B | BRCA2 | CIC | FANCE | GATA6 | JUN | MPL | PDGFRB | RICTOR | SUFU |
| AKT1 | BRD4 | CREBBP | FANCF | GID4 (C17orf39) | KAT6A (MYST3) | MRE11A | PDK1 | RNF43 | SYK |
| AKT2 | BRIP1 | CRKL | FANCG | GLI1 | KDM5A | MSH2 | PIK3C2B | ROS1 | TAF1 |
| AKT3 | BTG1 | CRLF2 | FANCL | GNA11 | KDM5C | MSH6 | PIK3CA | RPTOR | TBX3 |
| ALK | BTK | CSF1R | FAS | GNA13 | KDM6A | MTOR | PIK3CB | RUNX1 | TERC |
| AMER1 (FAM123B) | C11orf30 (EMSY) | CTCF | FAT1 | GNAQ | KDR | MUTYH | PIK3CG | RUNX1T1 | TERT (Promoter only) |
| APC | CARD11 | CTNNA1 | FBXW7 | GNAS | KEAP1 | MYC | PIK3R1 | SDHA | TET2 |
| AR | CBFB | CTNNB1 | FGF10 | GPR124 | KEL | MYCL (MYCL1) | PIK3R2 | SDHB | TGFBR2 |
| ARAF | CBL | CUL3 | FGF14 | GRIN2A | KIT | MYCN | PLCG2 | SDHC | TNFAIP3 |
| ARFRP1 | CCND1 | CYLD | FGF19 | GRM3 | KLHL6 | MYD88 | PMS2 | SDHD | TNFRSF14 |
| ARID1A | CCND2 | DAXX | FGF23 | GSK3B | KMT2A (MLL) | NF1 | POLD1 | SETD2 | TOP1 |
| ARID1B | CCND3 | DDR2 | FGF3 | H3F3A | KMT2C (MLL3) | NF2 | POLE | SF3B1 | TOP2A |
| ARID2 | CCNE1 | DICER1 | FGF4 | HGF | KMT2D (MLL2) | NFE2L2 | PPP2R1A | SLIT2 | TP53 |
| ASXL1 | CD274 (PD-L1) | DNMT3A | FGF6 | HNF1A | KRAS | NFKBIA | PRDM1 | SMAD2 | TSC1 |
| ATM | CD79A | DOT1L | FGFR1 | HRAS | LMO1 | NKX2-1 | PREX2 | SMAD3 | TSC2 |
| ATR | CD79B | EGFR | FGFR2 | HSD3B1 | LRP1B | NOTCH1 | PRKAR1A | SMAD4 | TSHR |
| ATRX | CDC73 | EP300 | FGFR3 | HSP90AA1 | LYN | NOTCH2 | PRKCI | SMARCA4 | U2AF1 |
| AURKA | CDH1 | EPHA3 | FGFR4 | IDH1 | LZTR1 | NOTCH3 | PRKDC | SMARCB1 | VEGFA |
| AURKB | CDK12 | EPHA5 | FH | IDH2 | MAGI2 | NPM1 | PRSS8 | SMO | VHL |
| AXIN1 | CDK4 | EPHA7 | FLCN | IGF1R | MAP2K1 (MEK1) | NRAS | PTCH1 | SNCAIP | WISP3 |
| AXL | CDK6 | EPHB1 | FLT1 | IGF2 | MAP2K2 (MEK2) | NSD1 | PTEN | SOCS1 | WT1 |
| BAP1 | CDK8 | ERBB2 | FLT3 | IKBKE | MAP2K4 | NTRK1 | PTPN11 | SOX10 | XPO1 |
| BARD1 | CDKN1A | ERBB3 | FLT4 | IKZF1 | MAP3K1 | NTRK2 | QKI | SOX2 | ZBTB2 |
| BCL2 | CDKN1B | ERBB4 | FOXL2 | IL7R | MCL1 | NTRK3 | RAC1 | SOX9 | ZNF217 |
| BCL2L1 | CDKN2A | ERG | FOXP1 | INHBA | MDM2 | NUP93 | RAD50 | SPEN | ZNF703 |
| BCL2L2 | CDKN2B | ERRFI1 | FRS2 | INPP4B | MDM4 | PAK3 | RAD51 | SPOP | |
| BCL6 | CDKN2C | ESR1 | FUBP1 | IRF2 | MED12 | PALB2 | RAF1 | SPTA1 | |
| BCOR | CEBPA | EZH2 | GABRA6 | IRF4 | MEF2B | PARK2 | RANBP2 | SRC | |
| BCORL1 | CHD2 | FAM46C | GATA1 | IRS2 | MEN1 | PAX5 | RARA | STAG2 | |
| BLM | CHD4 | FANCA | GATA2 | JAK1 | MET | PBRM1 | RB1 | STAT3 | |

TABLE 2

List of genes wherein selected introns are assayed in the FOUNDATIONONE ® assay.

| | | | | | | |
|---|---|---|---|---|---|---|
| ALK | BRCA1 | ETV1 | FGFR1 | MSH2 | NTRK1 | RARA |
| BCL2 | BRCA2 | ETV4 | FGFR2 | MYB | NTRK2 | RET |
| BCR | BRD4 | ETV5 | FGFR3 | MYC | PDGFRA | ROS1 |
| BRAF | EGFR | ETV6 | KIT | NOTCH2 | RAF1 | TMPRSS2 |

FOUNDATIONONE® Heme Assay

The FOUNDATIONONE® Heme assay is comprehensive genomic profiling assay for hematologic malignancies and sarcomas. The FOUNDATIONONE® Heme assay uses a hybrid-capture, next-generation sequencing test to identify genomic alterations (base substitutions, insertions and deletions, copy number alterations, and rearrangements). The assay analyzes the coding regions of 406 genes, selected introns of 31 genes, and the RNA sequences of 265 genes commonly rearranged in cancer. The full list of FOUNDATIONONE® Heme assay genes is provided in Tables 3, 4, and 5. See FOUNDATIONONE® HEME: Technical Specifications, Foundation Medicine, Inc., available at FoundationMedicine.com, last visited Mar. 16, 2018, which is incorporated by reference herein in its entirety.

TABLE 3

List of genes wherein entire coding sequences are assayed in the FOUNDATIONONE ® Heme assay.

| | | | | | | | | | |
|---|---|---|---|---|---|---|---|---|---|
| ABL1 | BRIP1 (BACH1) | CREBBP | FANCC | GNAS | JAK1 | MET | PBRM1 | ROS1 | TCF3 (E2A) |
| ACTB | BRSK1 | CRKL | FANCD2 | GPR124 | JAK2 | MIB1 | PC | RPTOR | TCL1A (TCL1) |
| AKT1 | BTG2 | CRLF2 | FANCE | GRIN2A | JAK3 | MITF | PCBP1 | RUNX1 | TET2 |
| AKT2 | BTK | CSF1R | FANCF | GSK3B | JARID2 | MKI67 | PCLO | S1PR2 | TGFBR2 |
| AKT3 | BTLA | CSF3R | FANCG | GTSE1 | JUN | MLH1 | PDCD1 (PD-1) | SDHA | TLL2 |
| ALK | C11orf30 (EMSY) | CTCF | FANCL | HDAC1 | KAT6A (MYST3) | MPL | PDCD11 | SDHB | TMEM30A |

TABLE 3-continued

List of genes wherein entire coding sequences are assayed in the FOUNDATIONONE ® Heme assay.

| | | | | | | | | | |
|---|---|---|---|---|---|---|---|---|---|
| AMER1 (FAM123B or WTX) | CAD | CTNNA1 | FAS (TNFRSF6) | HDAC4 | KDM2B | MRE11A | PDCD1LG2 (PD-L2) | SDHC | TMSB4XP8 (TMSL3) |
| APC | CALR | CTNNB1 | FBXO11 | HDAC7 | KDM4C | MSH2 | PDGFRA | SDHD | TNFAIP3 |
| APH1A | CARD11 | CUX1 | FBXO31 | HGF | KDM5A | MSH3 | PDGFRB | SERP2 | TNFRSF11A |
| AR | CBFB | CXCR4 | FBXW7 | HIST1H1C | KDM5C | MSH6 | PDK1 | SETBP1 | TNFRSF14 |
| ARAF | CBL | DAXX | FGF10 | HIST1H1D | KDM6A | MTOR | PHF6 | SETD2 | TNFRSF17 |
| ARFRP1 | CCND1 | DDR2 | FGF14 | HIST1H1E | KDR | MUTYH | PIK3CA | SF3B1 | TOP1 |
| ARHGAP26 (GRAF) | CCND2 | DDX3X | FGF19 | HIST1H2AC | KEAP1 | MYC | PIK3CG | SGK1 | TP53 |
| ARID1A | CCND3 | DNM2 | FGF23 | HIST1H2AG | KIT | MYCL (MYCL1) | PIK3R1 | SMAD2 | TP63 |
| ARID2 | CCNE1 | DNMT3A | FGF3 | HIST1H2AL | KLHL6 | MYCN | PIK3R2 | SMAD4 | TRAF2 |
| ASMTL | CCT6B | DOT1L | FGF4 | HIST1H2AM | KMT2A (MLL) | MYD88 | PIM1 | SMARCA1 | TRAF3 |
| ASXL1 | CD22 | DTX1 | FGF6 | HIST1H2BC | KMT2C (MLL3) | MYO18A | PLCG2 | SMARCA4 | TRAF5 |
| ATM | CD274 (PD-L1) | DUSP2 | FGFR1 | HIST1H2BJ | KMT2D (MLL2) | NCOR2 | POT1 | SMARCB1 | TSC1 |
| ATR | CD36 | DUSP9 | FGFR2 | HIST1H2BK | KRAS | NCSTN | PPP2R1A | SMC1A | TSC2 |
| ATRX | CD58 | EBF1 | FGFR3 | HIST1H2BO | LEF1 | NF1 | PRDM1 | SMC3 | TSHR |
| AURKA | CD70 | ECT2L | FGFR4 | HIST1H3B | LRP1B | NF2 | PRKAR1A | SMO | TUSC3 |
| AURKB | CD79A | EED | FHIT | HNF1A | LRRK2 | NFE2L2 | PRKDC | SOCS1 | TYK2 |
| AXIN1 | CD79B | EGFR | FLCN | HRAS | MAF | NFKB1A | PRSS8 | SOCS2 | U2AF1 |
| AXL | CDC73 | ELP2 | FLT1 | HSP90AA1 | MAFB | NKX2-1 | PTCH1 | SOCS3 | U2AF2 |
| B2M | CDH1 | EP300 | FLT3 | ICK | MAGED1 | NOD1 | PTEN | SOX10 | VHL |
| BAP1 | CDK12 | EPHA3 | FLT4 | ID3 | MALT1 | NOTCH1 | PTPN11 | SOX2 | WDR90 |
| BARD1 | CDK4 | EPHA5 | FLYWCH1 | IDH1 | MAP2K1 (MEK1) | NOTCH2 | PTPN2 | SPEN | WHSC1 (MMSET or NSD2) |
| BCL10 | CDK6 | EPHA7 | FOXL2 | IDH2 | MAP2K2 (MEK2) | NPM1 | PTPN6 (SHP-1) | SPOP | WISP3 |
| BCL11B | CDK8 | EPHB1 | FOXO1 | IGF1R | MAP2K4 | NRAS | PTPRO | SRC | WT1 |
| BCL2 | CDKN1B | ERBB2 | FOXO3 | IKBKE | MAP3K1 | NT5C2 | RAD21 | SRSF2 | XBP1 |
| BCL2L2 | CDKN2A | ERBB3 | FOXP1 | IKZF1 | MAP3K14 | NTRK1 | RAD50 | STAG2 | XPO1 |
| BCL6 | CDKN2B | ERBB4 | FRS2 | IKZF2 | MAP3K6 | NTRK2 | RAD51 | STAT3 | YY1AP1 |
| BCL7A | CDKN2C | ERG | GADD45B | IKZF3 | MAP3K7 | NTRK3 | RAF1 | STAT4 | ZMYM3 |
| BCOR | CEBPA | ESR1 | GATA1 | IL7R | MAPK1 | NUP93 | RARA | STAT5A | ZNF217 |
| BCORL1 | CHD2 | ETS1 | GATA2 | INHBA | MCL1 | NUP98 | RASGEF1A | STAT5B | ZNF24 (ZSCAN3) |
| BIRC3 | CHEK1 | ETV6 | GATA3 | INPP4B | MDM2 | P2RY8 | RB1 | STAT6 | ZNF703 |
| BLM | CHEK2 | EXOSC6 | GID4 (C17orf39) | INPP5D (SHIP) | MDM4 | PAG1 | RELN | STK11 | ZRSR2 |
| BRAF | CIC | EZH2 | GNA11 | IRF1 | MED12 | PAK3 | RET | SUFU | |
| BRCA1 | CIITA | FAF1 | GNA12 | IRF4 | MEF2B | PALB2 | RHOA | SUZ12 | |
| BRCA2 | CKS1B | FAM46C | GNA13 | IRF8 | MEF2C | PASK | RICTOR | TAF1 | |
| BRD4 | CPS1 | FANCA | GNAQ | IRS2 | MEN1 | PAX5 | RNF43 | TBL1XR1 | |

TABLE 4

List of genes wherein selected introns are assayed in the FOUNDATIONONE ® Heme assay.

| | | | | | | |
|---|---|---|---|---|---|---|
| ALK | BRAF | EPOR | ETV6 | IGK | KMT2A (MLL) | PDGFRB | ROS1 |
| BCL2 | CCND1 | ETV1 | EWSR1 | IGL | MYC | RAF1 | TMPRSS2 |
| BCL6 | CRLF2 | ETV4 | FGFR2 | JAK1 | NTRK1 | RARA | TRG |
| BCR | EGFR | ETV5 | IGH | JAK2 | PDGFRA | RET | |

TABLE 5

List of genes wherein RNA sequences are assayed in the FOUNDATIONONE ® Heme assay.

| | | | | | | | | | |
|---|---|---|---|---|---|---|---|---|---|
| ABI1 | BTG1 | DDIT3 | FGFR2 | HOXD11 | MAFB | NIN | PHF1 | RUNX2 | TFPT |
| ABL1 | CAMTA1 | DDX10 | FGFR3 | HOXD13 | MALT1 | NOTCH1 | PICALM | SEC31A | TFRC |
| ABL2 | CARS | DDX6 | FLI1 | HSP90AA1 | MDS2 | NPM1 | PIM1 | SEPT5 | TLX1 |
| ACSL6 | CBFA2T3 | DEK | FNBP1 | HSP90AB1 | MECOM | NR4A3 | PLAG1 | SEPT6 | TLX3 |
| AFF1 | CBFB | DUSP22 | FOXO1 | IGH | MKL1 | NSD1 | PML | SEPT9 | TMPRSS2 |
| AFF4 | CBL | EGFR | FOXO3 | IGK | MLF1 | NTRK1 | POU2AF1 | SET | TNFRSF11A |
| ALK | CCND1 | EIF4A2 | FOXO4 | IGL | MLLT1 (ENL) | NTRK2 | PPP1CB | SH3GL1 | TOP1 |

TABLE 5-continued

List of genes wherein RNA sequences are assayed in the FOUNDATIONONE ® Heme assay.

| | | | | | | | | | |
|---|---|---|---|---|---|---|---|---|---|
| ARHGAP26 (GRAF) | CCND2 | ELF4 | FOXP1 | IKZF1 | MLLT10 (AF10) | NTRK3 | PRDM1 | SLC1A2 | TP63 |
| ARHGEF12 | CCND3 | ELL | FSTL3 | IL21R | MLLT3 | NUMA1 | PRDM16 | SNX29 (RUNDC2A) | TPM3 |
| ARID1A | CD274 (PD-L1) | ELN | FUS | IL3 | MLLT4 (AF6) | NUP214 | PRRX1 | SRSF3 | TPM4 |
| ARNT | CDK6 | EML4 | GAS7 | IRF4 | MLLT6 | NUP98 | PSIP1 | SS18 | TRIM24 |
| ASXL1 | CDX2 | EP300 | GLI1 | ITK | MN1 | NUTM2A | PTCH1 | SSX1 | TRIP11 |
| ATF1 | CHIC2 | EPOR | GMPS | JAK1 | MNX1 | OMD | PTK7 | SSX2 | TTL |
| ATG5 | CHN1 | EPS15 | GPHN | JAK2 | MSI2 | P2RY8 | RABEP1 | SSX4 | TYK2 |
| ATIC | CIC | ERBB2 | HERPUD1 | JAK3 | MSN | PAFAH1B2 | RAF1 | STAT6 | USP6 |
| BCL10 | CIITA | ERG | HEY1 | JAZF1 | MUC1 | PAX3 | RALGDS | STL | WHSC1 (MMSET or NSD2) |
| BCL11A | CLP1 | ETS1 | HIP1 | KAT6A (MYST3) | MYB | PAX5 | RAP1GDS1 | SYK | WHSC1L1 |
| BCL11B | CLTC | ETV1 | HIST1H4l | KDSR | MYC | PAX7 | RARA | TAF15 | YPEL5 |
| BCL2 | CLTCL1 | ETV4 | HLF | KIF5B | MYH11 | PBX1 | RBM15 | TAL1 | ZBTB16 |
| BCL3 | CNTRL (CEP110) | ETV5 | HMGA1 | KMT2A (MLL) | MYH9 | PCM1 | RET | TAL2 | ZMYM2 |
| BCL6 | COL1A1 | ETV6 | HMGA2 | LASP1 | NACA | PCSK7 | RHOH | TBL1XR1 | ZNF384 |
| BCL7A | CREB3L1 | EWSR1 | HOXA11 | LCP1 | NBEAP1 (BCL8) | PDCD1LG2 (PD-L2) | RNF213 | TCF3 (E2A) | ZNF521 |
| BCL9 | CREB3L2 | FCGR2B | HOXA13 | LMO1 | NCOA2 | PDE4DIP | ROS1 | TCL1A (TCL1) | |
| BCOR | CREBBP | FCRL4 | HOXA3 | LMO2 | NDRG1 | PDGFB | RPL22 | TEC | |
| BCR | CRLF2 | FEV | HOXA9 | LPP | NF1 | PDGFRA | RPN1 | TET1 | |
| BIRC3 | CSF1 | FGFR1 | HOXC11 | LYL1 | NF2 | PDGFRB | RUNX1 | TFE3 | |
| BRAF | CTNNB1 | FGFR1OP | HOXC13 | MAF | NFKB2 | PER1 | RUNX1T1 (ETO) | TFG | |

EXODX® Solid Tumor Assay

In one embodiment, TMB is measured using the EXODX® Solid Tumor assay. The EXODX® Solid Tumor assay is an exoRNA- and cfDNA-based assay, which detects actionable mutations in cancer pathways. The EXODX® Solid Tumor assay is a plasma-based assay that does not require a tissue sample. The EXODX® Solid Tumor assay covers 26 genes and 1000 mutations. The specific genes covered by the EXODX® Solid Tumor assay are shown in Table 6. See Plasma-Based Solid Tumor Mutation Panel Liquid Biopsy, Exosome Diagnostics, Inc., available at exosomedx.com, last accessed on Mar. 16, 2018.

TABLE 6

Genes covered by the EXODX ® Solid Tumor assay.

| | | | | | | | | |
|---|---|---|---|---|---|---|---|---|
| BRAF | MEK1 | KIT | ROS1 | ALK | PTEN | TP53 | FGFR3 | TSC2 |
| NRAS | KRAS | PDGFRA | RET | | AKT1 DH2 | NOTCH1 | NTRK1 | CDKN2A |
| PIK3CA | EGFR | EML4-ALK | HER-2/NEU; ERBB2 | | ARv7 mTOR | Hedgehog | TSC1 | |

Guardant360 Assay

In some embodiments, TMB status is determined using the Guardant360 assay. The Guardant360 assay measures mutations in at least 73 genes (Table 7), 23 indels (Table 8), 18 CNVs (Table 9), and 6 fusion genes (Table 10). See GuardantHealth.com, last accessed on Mar. 16, 2018.

TABLE 7

Guardant360 assay genes.

| | | | | | | |
|---|---|---|---|---|---|---|
| AKT1 | CCND2 | EZH2 | IDH1 | MLH1 | PDGFRA | SMAD4 |
| ALK | CCNE1 | FBXW7 | IDH2 | MPL | PIK3CA | SMO |
| APC | CDH1 | FGFR1 | JAK2 | MTOR | PTEN | STK11 |
| AR | CDK4 | FGFR2 | JAK3 | MYC | PTPN11 | TERT (including promoter) |
| ARAF | CDK6 | FGFR3 | KIT | NF1 | RAF1 | TP53 |
| ARID1A | CDKN2A | GATA3 | KRAS | NFE2L2 | RB1 | TSC1 |
| ATM | CTNNB1 | GNA11 | MAP2K1 | NOTCH1 | RET | VHL |
| BRAF | DDR2 | GNAQ | MAP2K2 | NPM1 | RHEB | |
| BRCA1 | EGFR | GNAS | MAPK1 | NRAS | RHOA | |
| BRCA2 | ERBB2 | HNF1A | MAPK3 | NTRK1 | RIT1 | |
| CCND1 | ESR1 | HRAS | MET | NTRK3 | ROS1 | |

TABLE 8

Guardant360 assay indels.

| | | | | | | | |
|---|---|---|---|---|---|---|---|
| APC | BRCA1 | CDKN2A | GATA3 | MLH1 | PDGFRA | SMAD4 | TSC1 |
| ARID1A | BRCA2 | EGFR | KIT | MTOR | PTEN | STK11 | VHL |
| ATM | CDH1 | ERBB2 | MET | NF1 | RB1 | TP53 | |

TABLE 9

Guardant360 assay amplifications (CNVs).

| | | | | | |
|---|---|---|---|---|---|
| AR | CCND2 | CDK6 | FGFR1 | KRAS | PDGFRA |
| BRAF | CCNE1 | EGFR | FGFR2 | MET | PIK3CA |
| CCND1 | CDK4 | ERBB2 | KIT | MYC | RAF1 |

TABLE 10

Guardant360 assay fusions.

| | | |
|---|---|---|
| ALK | FGFR3 | RET |
| FGFR2 | NTRK1 | ROS1 |

ILLUMINA® TruSight Assay

In some embodiments, TMB is determined using the TruSight Tumor 170 assay (ILLUMINA®). The TruSight Tumor 170 assay is a next-generation sequencing assay that covers 170 genes associated with common solid tumors, which simultaneously analyzes DNA and RNA. The TruSight Tumor 170 assay assesses fusions, splice variants, insertions/deletions, single nucleotide variants (SNVs), and amplifications. The TruSight Tumor 170 assay gene lists are shown in Tables 11-13.

TABLE 11

TruSight Tumor 170 assay genes (amplifications).

| | | | | | |
|---|---|---|---|---|---|
| AKT2 | CDK4 | FGF1 | FGF7 | LAMP1 | PDGFRB |
| ALK | CDK6 | FGF10 | FGF8 | MDM2 | PIK3CA |
| AR | CHEK1 | FGF14 | FGF9 | MDM4 | PIK3CB |
| ATM | CHEK2 | FGF19 | FGFR1 | MET | PTEN |
| BRAF | EGFR | FGF2 | FGFR2 | MYC | RAF1 |
| BRCA1 | ERBB2 | FGF23 | FGFR3 | MYCL1 | RET |
| BRCA2 | ERBB3 | FGF3 | FGFR4 | MYCN | RICTOR |
| CCND1 | ERCC1 | FGF4 | JAK2 | NRAS | RPS6KB1 |
| CCND3 | ERCC2 | FGF5 | KIT | NRG1 | TFRC |
| CCNE1 | ESR1 | FGF6 | KRAS | PDGFRA | |

TABLE 12

TruSight Tumor 170 assay genes (fusions).

| | | | | | | | |
|---|---|---|---|---|---|---|---|
| ABL1 | BRCA1 | ERG | FGFR1 | JAK2 | MSH2 | NTRK2 | PPARG |
| AKT3 | BRCA2 | ESR1 | FGFR2 | KDR | MYC | NTRK3 | RAF1 |
| ALK | CDK4 | ETS1 | FGFR3 | KIF5B | NOTCH1 | PAX3 | RET |
| AR | CSF1R | ETV1 | FGFR4 | KIT | NOTCH2 | PAX7 | ROS1 |
| AXL | EGFR | ETV4 | FLI1 | KMT2A (MLL) | NOTCH3 | PDGFRA | RPS6KB1 |
| BCL2 | EML4 | ETV5 | FLT1 | MET | NRG1 | PDGFRB | TMPRSS2 |
| BRAF | ERBB2 | EWSR1 | FLT3 | MLLT3 | NTRK1 | PIK3CA | |

TABLE 13

TruSight Tumor 170 assay genes (small variants).

| | | | | | | | | | |
|---|---|---|---|---|---|---|---|---|---|
| AKT1 | BRCA2 | CHEK1 | ESR1 | FGF7 | HRAS | MET | NF1 | PMS2 | SLX4 |
| AKT2 | BRIP1 | CHEK2 | EZH2 | FGF8 | IDH1 | MLH1 | NOTCH1 | PPP2R2A | SMAD4 |
| AKT3 | BTK | CREBBP | FAM175A | FGF9 | IDH2 | MLLT3 | NOTCH2 | PTCH1 | SMARCB1 |
| ALK | CARD11 | CSF1R | FANCI | FGFR1 | INPP4B | MPL | NOTCH3 | PTEN | SMO |
| APC | CCND1 | CTNNB1 | FANCL | FGFR2 | JAK2 | MRE11A | NPM1 | PTPN11 | SRC |
| AR | CCND2 | DDR2 | FBXW7 | FGFR3 | JAK3 | MSH2 | NRAS | RAD51 | STK11 |
| ARID1A | CCNE1 | DNMT3A | FGF1 | FGFR4 | KDR | MSH3 | NRG1 | RAD51B | TERT |
| ATM | CD79A | EGFR | FGF10 | FLT1 | KIT | MSH6 | PALB2 | RAD51C | TET2 |
| ATR | CD79B | EP300 | FGF14 | FLT3 | KMT2A (MLL) | MTOR | PDGFRA | RAD51D | TP53 |
| BAP1 | CDH1 | ERBB2 | FGF2 | FOXL2 | KRAS | MUTYH | PDGFRB | RAD54L | TSC1 |
| BARD1 | CDK12 | ERBB3 | FGF23 | GEN1 | MAP2K1 | MYC | PIK3CA | RB1 | TSC2 |
| BCL2 | CDK4 | ERBB4 | FGF3 | GNA11 | MAP2K2 | MYCL1 | PIK3CB | RET | VHL |
| BCL6 | CDK6 | ERCC1 | FGF4 | GNAQ | MCL1 | MYCN | PIK3CD | RICTOR | XRCC2 |
| BRAF | CDKN2A | ERCC2 | FGF5 | GNAS | MDM2 | MYD88 | PIK3CG | ROS1 | |
| BRCA1 | CEBPA | ERG | FGF6 | HNF1A | MDM4 | NBN | PIK3R1 | RPS6KB1 | |

FOUNDATIONONE® F1CDx Assay

FOUNDATIONONE® CDX™ ("F1CDx") is a next generation sequencing based in vitro diagnostic device for detection of substitutions, insertion and deletion alterations (indels), and copy number alterations (CNAs) in 324 genes and select gene rearrangements, as well as genomic signatures including microsatellite instability (MSI) and tumor mutation burden (TMB) using DNA isolated from formalin-fixed paraffin embedded (FFPE) tumor tissue specimens. F1CDx is approved by the United States Food and Drug Administration (FDA) for several tumor indications, including NSCLC, melanoma, breast cancer, colorectal cancer, and ovarian cancer.

The F1CDx assay employs a single DNA extraction method from routine FFPE biopsy or surgical resection specimens, 50-1000 ng of which will undergo whole-genome shotgun library construction and hybridization-based capture of all coding exons from 309 cancer-related genes, one promoter region, one non-coding (ncRNA), and selected intronic regions from 34 commonly rearranged genes, 21 of which also include the coding exons. Tables 14 and 15 provide the complete list of genes included in F1CDx. In total, the assay detects alterations in a total of 324 genes. Using the ILLUMINA® HiSeq 4000 platform, hybrid capture-selected libraries are sequenced to high uniform depth (targeting >500× median coverage with >99% of exons at coverage >100×). Sequence data is then processed using a customized analysis pipeline designed to detect all classes of genomic alterations, including base substitutions, indels, copy number alterations (amplifications and homozygous gene deletions), and selected genomic rearrangements (e.g., gene fusions). Additionally, genomic signatures including microsatellite instability (MSI) and tumor mutation burden (TMB) are reported.

TABLE 14

Genes with full coding exonic regions included in FOUNDATIONONE ® CDX ™ for the detection of substitutions, insertions and deletions (indels), and copy number alterations (CNAs).

| | | | | | | | | | | |
|---|---|---|---|---|---|---|---|---|---|---|
| ABL1 | BRCA2 | CDKN2C | ERCC4 | GATA3 | KDM5C | MRE11A | PARP2 | RAD51 | SOX9 | |
| ACVR1B | BRD4 | CEBPA | ERG | GATA4 | KDM6A | MSH2 | PARP3 | RAD51B | SPEN | |
| AKT1 | BRIP1 | CHEK1 | ERRFI1 | GATA6 | KDR | MSH3 | PAX5 | RAD51C | SPOP | |
| AKT2 | BTG1 | CHEK2 | ESR1 | GID4 (C17orf39) | KEAP1 | MSH6 | PBRM1 | RAD51D | SRC | |
| AKT3 | BTG2 | CIC | EZH2 | GNA11 | KEL | MST1R | PDCD1 | RAD52 | STAG2 | |
| ALK | BTK | CREBBP | FAM46C | GNA13 | KIT | MTAP | PDCD1LG2 | RAD54L | STAT3 | |
| ALOX12B | C11orf30 | CRKL | FANCA | GNAQ | KLHL6 | MTOR | PDGFRA | RAF1 | STK11 | |
| AMER1 | CALR | CSF1R | FANCC | GNAS | KMT2A (MLL) | MUTYH | PDGFRB | RARA | SUFU | |
| APC | CARD11 | CSF3R | FANCG | GRM3 | KMT2D (MLL2) | MYC | PDK1 | RB1 | SYK | |
| AR | CASP8 | CTCF | FANCL | GSK3B | KRAS | MYCL | PIK3C2B | RBM10 | TBX3 | |
| ARAF | CBFB | CTNNA1 | FAS | H3F3A | LTK | MYCN | PIK3C2G | REL | TEK | |
| ARFRP1 | CBL | CTNNB1 | FBXW7 | HDAC1 | LYN | MYD88 | PIK3CA | RET | TET2 | |
| ARID1A | CCND1 | CUL3 | FGF10 | HGF | MAF | NBN | PIK3CB | RICTOR | TGFBR2 | |
| ASXL1 | CCND2 | CUL4A | FGF12 | HNF1A | MAP2K1 | NF1 | PIK3R1 | RNF43 | TIPARP | |
| ATM | CCND3 | CXCR4 | FGF14 | HRAS | MAP2K2 | NF2 | PIM1 | ROS1 | TNFAIP3 | |
| ATR | CCNE1 | CYP17A1 | FGF19 | HSD3B1 | MAP2K4 | NFE2L2 | PMS2 | RPTOR | TNFRSF14 | |
| ATRX | CD22 | DAXX | FGF23 | ID3 | MAP3K1 | NFKBIA | POLD1 | SDHA | TP53 | |
| AURKA | CD274 | DDR1 | FGF3 | IDH1 | MAP3K13 | NKX2-1 | POLE | SDHB | TSC1 | |
| AURKB | CD70 | DDR2 | FGF4 | IDH2 | MAPK1 | NOTCH1 | PPARG | SDHC | TSC2 | |
| AXIN1 | CD79A | DIS3 | FGF6 | IGF1R | MCL1 | NOTCH2 | PPP2R1A | SDHD | TYRO3 | |
| AXL | CD79B | DNMT3A | FGFR1 | IKBKE | MDM2 | NOTCH3 | PPP2R2A | SETD2 | U2AF1 | |
| BAP1 | CDC73 | DOT1L | FGFR2 | IKZF1 | MDM4 | NPM1 | PRDM1 | SF3B1 | VEGFA | |
| BARD1 | CDH1 | EED | FGFR3 | INPP4B | MED12 | NRAS | PRKAR1A | SGK1 | VHL | |
| BCL2 | CDK12 | EGFR | FGFR4 | IRF2 | MEF2B | NT5C2 | PRKCI | SMAD2 | WHSC1 | |
| BCL2L1 | CDK4 | EP300 | FH | IRF4 | MEN1 | NTRK1 | PTCH1 | SMAD4 | WHSC1L1 | |
| BCL2L2 | CDK6 | EPHA3 | FLCN | IRS2 | MERTK | NTRK2 | PTEN | SMARCA4 | WT1 | |
| BCL6 | CDK8 | EPHB1 | FLT1 | JAK1 | MET | NTRK3 | PTPN11 | SMARCB1 | XPO1 | |
| BCOR | CDKN1A | EPHB4 | FLT3 | JAK2 | MITF | P2RY8 | PTPRO | SMO | XRCC2 | |
| BCORL1 | CDKN1B | ERBB2 | FOXL2 | JAK3 | MKNK1 | PALB2 | QK1 | SNCAIP | ZNF217 | |
| BRAF | CDKN2A | ERBB3 | FUBP1 | JUN | MLH1 | PARK2 | RAC1 | SOCS1 | ZNF703 | |
| BRCA1 | CDKN2B | ERBB4 | GABRA6 | KDM5A | MPL | PARP1 | RAD21 | SOX2 | | |

TABLE 15

Genes with selected intronic regions for the detection of gene rearrangements, one with 3'UTR, one gene with a promoter region and one ncRNA gene.

| ALK introns 18, 19 | BRCA1 introns 2, 7, 8, 12, 16, 19, 20 | ETV4 introns 5, 6 | EZR introns 9-11 | KIT intron 16 | MYC intron 1 | NUTM1 intron 1 | RET introns 7-11 | SLC34A2 intron 4 |
|---|---|---|---|---|---|---|---|---|
| BCL2 3'UTR | BRCA2 intron 2 | ETV5 introns 6, 7 | FGFR1 intron 1, 5, 17 | KMT2A (MLL) introns 6-11 | NOTCH2 intron 26 | PDGFRA introns 7, 9, 11 | ROS1 introns 31-35 | TERC ncRNA |
| BCR introns 8, 13, 14 | CD74 introns 6-8 | ETV6 introns 5, 6 | FGFR2 intron 1, 17 | MSH2 intron 5 | NTRK1 introns 8-10 | RAF1 introns 4-8 | RSPO2 intron 1 | TERT Promoter |

TABLE 15-continued

Genes with selected intronic regions for the detection of gene rearrangements, one with 3'UTR, one gene with a promoter region and one ncRNA gene.

| BRAF introns 7-10 | EGFR introns 7, 15, 24-27 | EWSR1 introns 7-13 | FGFR3 intron 17 | MYB intron 14 | NTRK2 Intron 12 | RARA intron 2 | SDC4 intron 2 | TMPRSS2 introns 1-3 |
|---|---|---|---|---|---|---|---|---|

The F1CDx assay identifies various alterations in the gene and/or intron sequences, including substitutions, insertions/deletions, and CNAs. The F1CDx assay was previously identifies as having concordance with an externally validated NGS assay and the FOUNDATIONONE® (F1 LDT) assay. See FOUNDATIONONE® CDX™: Technical Information, Foundation Medicine, Inc., available at Foundation-Medicine.com, last visited Mar. 16, 2018, which is incorporated by reference herein in its entirety.

MSK-IMPACT™

In some embodiments, TMB status is assessed using the MSK-IMPACT™ assay. The MSK-IMPACT™ assay uses next-generation sequencing to analyze the mutation status of 468 genes. Target genes are captured and sequenced on an ILLUMINA® HISEQ™ instrument. The MSK-IMPACT™ assay is approved by the US FDA for detection of somatic mutations and microsatellite instability in solid malignant neoplasms. The full list of 468 genes analyzed by the MSK-IMPACT™ assay is shown in Table 16. See Evaluation of Automatic Class III Designation for MSK-IMPACT (Integrated Mutation Profiling of Actionable Cancer Targets): Decision Summary, United States Food and Drug Administration, Nov. 15, 2017, available at accessdata.fda.gov.

TABLE 16

Genes analyzed by the MSK-IMPACT ™ assay.

| | | | | | | | | | |
|---|---|---|---|---|---|---|---|---|---|
| ABL1 | CALR | DDR2 | FGF19 | HIST3H3 | LYN | NKX2-1 | PPARG | RPTOR | STK19 |
| ACVR1 | CARD11 | DICER1 | FGF3 | HLA-A | MALT1 | NKX3-1 | PPM1D | RRAGC | STK40 |
| AGO2 | CARM1 | DIS3 | FGF4 | HLA-B | MAP2K1 | NOTCH1 | PPP2R1A | RRAS | SUFU |
| AKT1 | CASP8 | DNAJB1 | FGFR1 | HNF1A | MAP2K2 | NOTCH2 | PPP4R2 | RRAS2 | SUZ12 |
| AKT2 | CBFB | DNMT1 | FGFR2 | HOXB13 | MAP2K4 | NOTCH3 | PPP6C | RTEL1 | SYK |
| AKT3 | CBL | DNMT3A | FGFR3 | HRAS | MAP3K1 | NOTCH4 | PRDM1 | RUNX1 | TAP1 |
| ALK | CCND1 | DNMT3B | FGFR4 | ICOSLG | MAP3K13 | NPM1 | PRDM14 | RXRA | TAP2 |
| ALOX12B | CCND2 | DOT1L | FH | ID3 | MAP3K14 | NRAS | PREX2 | RYBP | TBX3 |
| AMER1 | CCND3 | DROSHA | FLCN | IDH1 | MAPK1 | NSD1 | PRKAR1A | SDHA | TCEB1 |
| ANKRD11 | CCNE1 | DUSP4 | FLT1 | IDH2 | MAPK3 | NTHL1 | PRKCI | SDHAF2 | TCF3 |
| APC | CD274 | E2F3 | FLT3 | IFNGR1 | MAPKAP1 | NTRK1 | PRKD1 | SDHB | TCF7L2 |
| AR | CD276 | EED | FLT4 | IGF1 | MAX | NTRK2 | PTCH1 | SDHC | TEK |
| ARAF | CD79A | EGFL7 | FOXA1 | IGF1R | MCL1 | NTRK3 | PTEN | SDHD | TERT |
| ARID1A | CD79B | EGFR | FOXL2 | IGF2 | MDC1 | NUF2 | PTP4A1 | SESN1 | TET1 |
| ARID1B | CDC42 | EIF1AX | FOXO1 | IKBKE | MDM2 | NUP93 | PTPN11 | SESN2 | TET2 |
| ARID2 | CDC73 | EIF4A2 | FOXP1 | IKZF1 | MDM4 | PAK1 | PTPRD | SESN3 | TGFBR1 |
| ARID5B | CDH1 | EIF4E | FUBP1 | IL10 | MED12 | PAK7 | PTPRS | SETD2 | TGFBR2 |
| ASXL1 | CDK12 | ELF3 | FYN | IL7R | MEF2B | PALB2 | PTPRT | SETD8 | TMEM127 |
| ASXL2 | CDK4 | EP300 | GATA1 | INHA | MEN1 | PARK2 | RAB35 | SF3B1 | TMPRSS2 |
| ATM | CDK6 | EPAS1 | GATA2 | INHBA | MET | PARP1 | RAC1 | SH2B3 | TNFAIP3 |
| ATR | CDK8 | EPCAM | GATA3 | INPP4A | MGA | PAX5 | RAC2 | SH2D1A | TNFRSF14 |
| ATRX | CDKN1A | EPHA3 | GLI1 | INPP4B | MITF | PBRM1 | RAD21 | SHOC2 | TOP1 |
| AURKA | CDKN1B | EPHA5 | GNA11 | INPPL1 | MLH1 | PDCD1 | RAD50 | SHQ1 | TP53 |
| AURKB | CDKN2Ap-14ARF | EPHA7 | GNAQ | INSR | MPL | PDCD1LG2 | RAD51 | SLX4 | TP53BP1 |
| AXIN1 | CDKN2Ap-16INK4A | EPHB1 | GNAS | IRF4 | MRE11A | PDGFRA | RAD51B | SMAD2 | TP63 |
| AXIN2 | CDKN2B | ERBB2 | GPS2 | IRS1 | MSH2 | PDGFRB | RAD51C | SMAD3 | TRAF2 |
| AXL | CDKN2C | ERBB3 | GREM1 | IRS2 | MSH3 | PDPK1 | RAD51D | SMAD4 | TRAF7 |
| B2M | CEBPA | ERBB4 | GRIN2A | JAK1 | MSH6 | PGR | RAD52 | SMARCA4 | TSC1 |
| BABAM1 | CENPA | ERCC2 | GSK3B | JAK2 | MSI1 | PHOX2B | RAD54L | SMARCB1 | TSC2 |
| BAP1 | CHEK1 | ERCC3 | H3F3A | JAK3 | MSI2 | PIK3C2G | RAF1 | SMARCD1 | TSHR |
| BARD1 | CHEK2 | ERCC4 | H3F3B | JUN | MST1 | PIK3C3 | RARA | SMO | U2AF1 |
| BBC3 | CIC | ERCC5 | H3F3C | KDM5A | MST1R | PIK3CA | RASA1 | SMYD3 | UPF1 |
| BCL10 | CREBBP | ERF | HGF | KDM5C | MTOR | PIK3CB | RB1 | SOCS1 | VEGFA |
| BCL2 | CRKL | ERG | HIST1H1C | KDM6A | MUTYH | PIK3CD | RBM10 | SOS1 | VHL |
| BCL2L1 | CRLF2 | ERRFI1 | HIST1H2BD | KDR | MYC | PIK3CG | RECQL | SOX17 | VTCN1 |
| BCL2L11 | CSDE1 | ESR1 | HIST1H3A | KEAP1 | MYCL1 | PIK3R1 | RECQL4 | SOX2 | WHSC1 |
| BCL6 | CSF1R | ETV1 | HIST1H3B | KIT | MYCN | PIK3R2 | REL | SOX9 | WHSC1L1 |
| BCOR | CSF3R | ETV6 | HIST1H3C | KLF4 | MYD88 | PIK3R3 | RET | SPEN | WT1 |
| BIRC3 | CTCF | EZH1 | HIST1H3D | KMT2A | MYOD1 | PIM1 | RFWD2 | SPOP | WWTR1 |
| BLM | CTLA-4 | EZH2 | HIST1H3E | KMT2B | NBN | PLCG2 | RHEB | SPRED1 | XIAP |
| BMPR1A | CTNNB1 | FAM175A | HIST1H3F | KMT2C | NCOA3 | PLK2 | RHOA | SRC | XPO1 |
| BRAF | CUL3 | FAM46C | HIST1H3G | KMT2D | NCOR1 | PMAIP1 | RICTOR | SRSF2 | XRCC2 |
| BRCA1 | CXCR4 | FAM58A | HIST1H3H | KNSTRN | NEGR1 | PMS1 | RIT1 | STAG2 | YAP1 |
| BRCA2 | CYLD | FANCA | HIST1H3I | KRAS | NF1 | PMS2 | RNF43 | STAT3 | YES1 |
| BRD4 | CYSLTR2 | FANCC | HIST1H3J | LATS1 | NF2 | PNRC1 | ROS1 | STAT5A | ZFHX3 |
| BRIP1 | DAXX | FAT1 | HIST2H3C | LATS2 | NFE2L2 | POLD1 | RPS6KA4 | STAT5B | |
| BTK | DCUN1D1 | FBXW7 | HIST2H3D | LMO1 | NFKBIA | POLE | RPS6KB2 | STK11 | |
| ABL1 | CALR | DDR2 | FGF19 | HIST3H3 | LYN | NKX2-1 | PPARG | RPTOR | STK19 |

NEOGENOMICS® NEOTYPE™ Assays

In some embodiments, TMB is determined using a NEOGENOMICS® NEOTYOPE™ assay. In some embodiments, the TMB is determined using a NEOTYPE™ Discovery Profile. In some embodiments, the TMB is determined using a NEOTYPE™ Solid Tumor Profile. The NEOGENOMICS® assays measure the number of non-synonymous DNA coding sequence changes per megabase of sequenced DNA.

ONCOMINE™ Tumor Mutation Load Assay

In some embodiments, TMB is determined using a THERMOFISHER SCIENTIFIC® ONCOMINE™ Tumor Mutation assay. In some embodiments, TMB is determined using a THERMOFISHER SCIENTIFIC® ION TORRENT™ ONCOMINE™ Tumor Mutation assay. The ION TORRENT™ ONCOMINE™ Tumor Mutation assay is a targeted NGS assay that quantitates somatic mutations to determine tumor mutation load. The assay covers 1.7 Mb of DNA.

NOVOGENE™ NOVOPM™ Assay

In some embodiments, TMB is determined using a NOVOGENE™ NOVOPM™ assay. In some embodiments, TMB is determined using a NOVOGENE™ NOVOPM™ Cancer Panel assay. The NOVOGENE™ NOVOPM™ Cancer Panel assay is a comprehensive NGS cancer panel that analyzes the complete coding regions of 548 genes and the introns of 21 genes, representing about 1.5 Mb of DNA, and that are relevant for the diagnosis and/or treatment of solid tumors according to the National Comprehensive Cancer Network (NCCN) guidelines and medical literature. The assay detects SNV, InDel, fusion, and copy number variation (CNV) genomic abnormalities.

Other TMB Assays

In some embodiments, TMB is determined using a TMB assay provided by CARIS® Life Sciences. In some embodiments, TMB is determined using the PESONALIS® ACE ImmunoID assay. In some embodiments, TMB is determined using the PGDX® CANCERXOME™-R assay.

In yet another particular embodiment, the genomic profiling detects all mutation types, i.e., single nucleotide variants, insertions/deletions (indels), copy number variations, and rearrangements, e.g., translocations, expression, and epigenetic markers.

Comprehensive gene panels often contain predetermined genes selected based on the type of tumor to be analyzed. Accordingly, the genomic profile used to measure TMB status can be selected based on the type of tumor the subject has. In one embodiment, the genomic profile can include a set of genes particular to a solid tumor. In another embodiment, the genomic profile can include a set of genes particular to hematologic malignancies and sarcomas.

In one embodiment, the genomic profile comprises one or more genes selected from the group consisting of ABL1, BRAF, CHEK1, FANCC, GATA3, JAK2, MITE, PDCDILG2, RBM10, STAT4, ABL2, BRCA1, CHEK2, FANCD2, GATA4, JAK3, MLH1, PDGFRA, RET, STK11, ACVR1B, BRCA2, CIC, FANCE, GATA6, JUN, MPL, PDGFRB, RICTOR, SUFU, AKT1, BRD4, CREBBP, FANCE, GID4 ((17orf39), KAT6A (MYST3), MRE11A, PDK1, RNF43, SYK, AKT2, BRIP1, CRKL, FANCG, GLI1, KDM5A, MSH2, PIK3C2B, ROS1, TAF1, AKT3, BTG1, CRLF2, FANCL, GNA11, KDM5C, MSH6, PIK3CA, RPTOR, TBX3, ALK, BTK, CSF1R, FAS, GNA13, KDM6A, MTOR, PIK3CB, RUNX1, TERC, AMER1 (FAM123B), C11orf30 (EMSY), CTCF, FAT1, GNAQ, KDR, MUTYH, PIK3CG, RUNX1T1, TERT (promoter only), APC, CARD11, CTNNA1, FBXW7, GNAS, KEAP1, MYC, PIK3R1, SDHA, TET2, AR, CBFB, CTNNB1, FGF10, GPR124, KEL, MYCL (MYCL1), PIK3R2, SDHB, TGFBR2, ARAF, CBL, CUL3, FGF14, GRIN2A, KIT, MYCN, PLCG2, SDHC, TNFAIP3, ARFRP1, CCND1, CYLD, FGF19, GRM3, KLHL6, MYD88, PMS2, SDHD, TNFRSF14, ARID1A, COND2, DAXX, FGF23, GSK3B, KMT2A (MLL), NF1, POLD1, SETD2, TOP1, ARID1B, COND3, DDR2, FGF3, H3F3A, KMT20 (MLL3), NF2, POLE, SF3B1, TOP2A, ARID2, CCNE1, DICER1, FGF4, HGF, KMT2D) (MLL2), NFE212, PPP2RIA, SLIT2, TP53, ASXL1, CD274, DNMT3A, FGF6, HNF1A, KRAS, NFKBIA, PRDM1, SMAD2, TSC1, ATM, CD79A, DOT1L, FGFR1, HRAS, LMO1, NKX2-1, PREX2, SMAD3, TSC2, ATR, CD79B, EGFR, FGFR2, HSD3B1, LRP1B, NOTCH1, PRKAR1A, SMAD4, TSHR, ATRX, CDC73, EP300, FGFR3, HSP90AAI, LYN, NOTCH2, PRKC1, SMARCA4, U2AF1, AURKA, CDH1, EPHA3, FGFR4, IDH1, LZTR1, NOTCH3, PRKDC, SMARCB1, VEGFA, AURKB, CDK12, EPHA5, FH, IDH2, MAGI2, NPM1, PRSS8, SMO, VHL, AXIN1, CDK4, EPHA7, FLCN, IGF1R, MAP2K1, NRAS, PTCH1, SNCA1P, WISP3, AXL, CDK6, EPHB1, FLT1, IGF2, MAP2K2, NSD1, PTEN, SOCS1, WT1, BAP1, CDK8, ERBB2, FLT3, IKBKE, MAP2K4, NTRK1, PTPN11, SOX10, XPO1, BARD1, CDKN1A, ERBB3, FLT4, IKZF1, MAP3K1, NTRK2, QK1, SOX2, ZBTB2, BCL2, CDKN1B, ERBB4, FOXL2, IL7R, MCLI, NTRK3, RAC1, SOX9, ZNF217, BCL2L1, CDKN2A, ERG, FOXP1, INHBA, MDM2, NUP93, RAD50, SPEN, ZNF703, BCL2L2, CDKN2B, ERRF11, FRS2, INPP4B, MDM4, PAK3, RAD51, SPOP, BCL6, CDKN2C, ESR1, FUBP1, IRF2, MED12, PALB2, RAF1, SPTA1, BCOR, CEBPA, EZH2, GABRA6, IRF4, MEF2B, PARK2, RANBP2, SRC, BCORL1, CHD2, FAM46C, GATA1, IRS2, MEN1, PAX5, RARA, STAG2, BLM, CHD4, FANCA, GATA2, JAKI, MET, PBRM1, RB1, STAT3, and any combination thereof. In other embodiments, the TMB analysis further comprises identifying a genomic alteration in one or more of ETV4, TMPRSS2, ETV5, BCR, ETV1, ETV6, and MYB.

In another embodiment, the genomic profile comprises one or more genes selected from the group consisting of ABL1, 12B, ABL2, ACTB, ACVR1, ACVR1B, AGO2, AKT1, AKT2, AKT3, ALK, ALOX, ALOX12B, AMER1, AMER1 (FAM123B or WTX), AMER1 (FAM123B), ANKRD11, APC, APH1A, AR, ARAF, ARFRP1, ARHGAP26 (GRAF), ARID1A, ARID1B, ARID2, ARID5B, ARv7, ASMTL, ASXL1, ASXL2, ATM, ATR, ATRX, AURKA, AURKB, AXIN1, AXIN2, AXL, B2M, BABAM1, BAP1, BARD1, BBC3, BCL10, BCL11B, BCL2, BCL2L1, BCL2LII, BCL2L2, BCL6, BCL7A, BCOR, BCORL1, BIRC3, BLM, BMPR1A, BRAF, BRCA1, BRCA2, BRD4, BRIP1, BRIP1 (BACH1), BRSK1, BTG1, BTG2, BTK, BTLA, C11orf30 (EMSY), C11orf30, C11orf30 (EMSY), CAD, CALR, CARD11, CARMI, CASP8, CBFB, CBL, CCND1, COND2, COND3, CCNE1, CCT6B, CD22, CD274, CD274 (PD-L1), CD276, CD36, CD58, CD70, CD79A, CD79B, CDC42, CDC73, CDH1, CDK12, CDK4, CDK6, CDK8, CDKN1A, CDKN1B, CDKN2A, CDKN2Ap14ARF, CDKN2Ap16INK4A, CDKN2B, CDKN2C, CEBPA, CENPA, CHD2, CHD4, CHEK1, CHEK2, CIC, CIITA, CKS1B, CPSI, CREBBP, CRKL, CRLF2, CSDE1, CSF1R, CSF3R, CTCF, CTLA-4, CTNN B1, CTNNA1, CTNNB1, CUL3, CUL4A, CUX1, CXCR4, CYLD, CYP17AI, CYSLTR2, DAXX, DCUN1D1, DDR1, DDR2, DDX3x, DH2, DICER1, DIS3, DNAJB1, DNM2, DNMT1, DNMT3A, DNMT3B, DOT1L, DROSHA, DTX1, DUSP2, DUSP4, DUSP9, E2F3, EBF1, ECT2L, EED, EGFL7, EGFR, EIF1AX, EIF4A2, EIF4E, ELF3, ELP2, EML4, EML4-ALK, EP300, EPAS1, EPCAM, EPHA3, EPHA5, EPHA7, EPHB1, EPHB4, ERBB2, ERBB3, ERBB4, ERCC1, ERCC2, ERCC3, ERCC4, ERCC5, ERF, ERG, ERRFI1, ERRFI1, ESR1, ETS1, ETV1, ETV4, ETV5, ETV6, EWSR1, EXOSC6, EZH1, EZH2, FAF1, FAM175A, FAM46C, FAM58A, FANCA, FANCC, FANCD2, FANCE, FANCE, FANCG, FANCI, FANCL, FAS, FAS (TNFRSF6), FAT1, FBXO11, FBXO31, FBXW7, FGF1, FGF10, FGF12, FGF14, FGF19, FGF2, FGF23, FGF3, FGF4, FGF5, FGF6, FGF7, FGF8, FGF9, FGFR1, FGFR2, FGFR3, FGFR4, FH, FHIT, FLCN, FLI1, FLT1, FLT3, FLT4, FLYWCH1, FOXA1, FOXL2, FOXO1, FOXO3, FOXP1, FRS2, FUBP1, FYN, GABRA6, GADD45B, GATA1, GATA2, GATA3, GATA4, GATA6, GEN1, GID4 ((17orf 39), GID4 ((17orf39), GLI1, GLI1, GNAI1, GNA12, GNA13, GNAQ, GNAS, GPR124, GPS2, GREM1, GRIN2A, GRM3, GSK3B, GTSE1, H3F3A, H3F3B, H3F3C, HDAC1, HDAC4, HDAC7, Hedgehog, HER-2 NEU; ERBB2, HGF, HIST1H1C, HIST1H1D, HIST1H1E, HIST1H2AC, HIST1H2AG, HIST1H2AL, HIST1H2AM, HIST1H2BC, HIST1H2BD, HIST1H2BJ, HIST1H2BK, HIST1H2BO, HIST1H3A, HIST1H3B, HIST1H3C, HIST1H3D, HIST1H3E, HIST1H3F, HIST1H3G, HIST1H3H, HIST1H3I, HIST1H3J, HIST2H3C, HIST2H3D, HIST3H3, HLA-A, HLA-B, HNF1A, HOXB13, HRAS, HSD3B1, HSP90AA1, ICK, ICOSLG, ID3, IDH1, IDH2, IFNGR1, IGF1, IGF1R, IGF2, IKBKE, IKZF1, IKZF2, IKZF3, IL10, IL7R, INHA, INHBA, INPP4A, INPP4B, INPP5D) (SHIP), INPPL1, INSR, IRF1, IRF2, IRF4, IRF8, IRS1, IRS2, JAK1, JAK2, JAK3, JARID2, JUN, K14, KAT6A (MYST 3), KAT6A (MYST3), KDM2B, KDM4C, KDM5A, KDM5C, KDM6A, KDR, KEAP1, KEL, KIF5B, KIT, KLF4, KLHL6, KMT2A, KMT2A (MLL), KMT2B, KMT2C, KMT2 ((MLL3), KMT2D, KMT2D (MLL2), KNSTRN, KRAS, LAMP1, LATS1, LATS2, LEF1, LMO1, LRP1B, LRRK2, LTK, LYN, LZTR1, MAF, MAFB, MAGED1, MAGI2, MALT1, MAP2K1, MAP2K1 (MEK1), MAP2K2, MAP2K2 (MEK2), MAP2K4, MAP3, MAP3K1, MAP3K13, MAP3K14, MAP3K6, MAP3K7, MAPK1, MAPK3, MAPKAP1, MAX, MCL1, MDC1, MDM2, MDM4, MED12, MEF2B, MEF2C, MEK1, MEN1, MERTK, MET, MGA, MIB1, MITF, MKI67, MKNK1, MLH1, MLLT3, MPL, MRE 1IA, MRE11A, MSH2, MSH3, MSH6, MSI1, MSI2, MST1, MST1R, MTAP, MTOR, MUTYH, MYC, MYCL, MYCL (MYC L1), MYCL (MYCL1), MYCL1, MYCN, MYD88, MYO18A, MYOD1, NBN, NCOA3, NCOR1, NCOR2, NCSTN, NEGR1, NF1, NF2, NFE2L2, NEKBIA, NKX2-1, NKX3-1, NOD1, NOTCH1, NOTCH2, NOTCH3, NOTCH4, NPM1, NRAS, NRG1, NSD1, NT502, NTHL1, NTRK1, NTRK2, NTRK3, NUF2, NUP93, NUP98, P2RY8, PAG1, PAKI, PAK3, PAK7, PALB2, PARK2, PARP1, PARP2, PARP3, PASK, PAX3, PAX5, PAX7, PBRM1, PC, PCBP1, PCLO, PDCD1, PDCD1 (PD-1), PDCD11, PDCDILG2, PDCDILG2 (PD-L2), PDGFRA, PDGFRB, PDK1, PDPK1, PGR, PHF6, PHOX2B, PIK3C2B, PIK3C2G, PIK3C3, PIK3CA, PIK3CB, PIK3CD, PIK3CG, PIK3R1, PIK3R2, PIK3R3, PIM1, PLCG2, PLK2, PMAIP1, PMS1, PMS2, PNRC1, POLD1, POLE, POT1, PPARG, PPMID, PPP2, PPP2R1A, PPP2R2A, PPP4R2, PPP6C, PRDM1, PRDM14, PREX2, PRKAR1A, PRKC1, PRKD1, PRKDC, PRSS8, PTCH1, PTEN, PTP4A1, PTPN11, PTPN2, PTPN6 (SHP-1), PTPRD, PTPRO, PTPRS, PTPRT, QK1, RIA, RAB35, RAC1, RAC2, RAD21, RAD50, RAD51, RAD51B, RAD51C, RAD51D, RAD52, RAD54L, RAF1, RANBP2, RARA, RASA1, RASGEF1A, RB1, RBM10, RECOL, RECQL4, REL, RELN, RET, RFWD2, RHEB, RHOA, RICTOR, RIT1, RNF43, ROS1, RPS6KA4, RPS6KB1, RPS6KB2, RPTOR, RRAGC, RRAS, RRAS2, RTEL1, RUNX1, RUNX1T1, RXRA, RYBP, SIPR2, SDHA, SDHAF2, SDHB, SDHC, SDHD, SERP2, SESN1, SESN2, SESN3, SETBP1, SETD2, SETD8, SF3BI, SGK1, SH2B3, SH2DIA, SHOC2, SHQ1, SLIT2, SLX4, SMAD2, SMAD3, SMAD4, SMARCA1, SMARCA4, SMARCB1, SMARCD1, SMC1A, SMC3, SMO, SMYD3, SNCA1P, SOCS1, SOCS2, SOCS3, SOS1, SOX10, SOX17, SOX2, SOX9, SPEN, SPOP, SPRED1, SPTA1, SRC, SRSF2, STAG2, STAT3, STAT4, STATSA, STATSB, STAT6, STK11, STK19, STK40, SUFU, SUZI2, SYK, TAF1, TAP1, TAP2, TBL1XR1, TBX3, TCEB1, TCF3, TCF3 (E2A), TCF7L2, TCL1A (TCL1), TEK, TERC, TERT, TERT Promoter, TETI, TET2, TFRC, TGFBR1, TGFBR2, TIPARP, TLL2, TMEM127, TMEM30A, TMPRSS2, TMSB4XP8 (TMSL3), TNFAIP3, TNFRSF1IA, TNFRSF14, TNFRSF17, TOP1, TOP2A, TP53, TP53BP1, TP63, TRAF2, TRAF3, TRAF5, TRAF7, TSC1, TSC2, TSHR, TUSC3, TYK2, TYRO3, U2AF1, U2AF2, UPF1, VEGFA, VHL, VTCN1, WDR90, WHSC1, WHSC1 (MMSET or NSD2), WHSCIL1, WISP3, WT1, WWTR1, XBP1, XIAP, XPO1, XRCC2, YAP1, YES1, YY1AP1, ZBTB2, ZFHX3, ZMYM3, ZNF217, ZNF24 (ZSCAN3), ZNF703, ZRSR2, and any combination thereof.

In another embodiment, the genomic profiling assay comprises at least about 20, at least about 30, at least about 40, at least about 50, at least about 60, at least about 70, at least about 80, at least about 90, at least about 100, at least about 110, at least about 120, at least about 130, at least about 140, at least about 150, at least about 160, at least about 170, at least about 180, at least about 190, at least about 200, at least about 210, at least about 220, at least about 230, at least about 240, at least about 250, at least about 260, at least about 270, at least about 280, at least about 290, or at least about 300 genes selected from the group consisting of ABL1, 12B, ABL2, ACTB, ACVR1, ACVR1B, AGO2, AKT1, AKT2, AKT3, ALK, ALOX, ALOX12B, AMER1, AMER1 (FAM123B or WTX), AMER1 (FAM123B), ANKRD11, APC, APH1A, AR, ARAF, ARFRP1, ARHGAP26 (GRAF), ARID1A, ARID1B, ARID2, ARID5B, ARv7, ASMTL, ASXL1, ASXL2, ATM, ATR, ATRX, AURKA, AURKB, AXIN1, AXIN2, AXL, B2M, BABAM1, BAP1, BARD1, BBC3, BCL10, BCL11B, BCL2, BCL2L1, BCL2L11, BCL2L2, BCL6, BOLTA, BCOR, BCORL1, BIRC3, BLM, BMPR1A, BRAF, BRCA1, BRCA2, BRD4, BRIP1, BRIP1 (BACH1), BRSK1, BTG1, BTG2, BTK, BTLA, C11orf 30 (EMSY), C11orf30, C11orf30 (EMSY), CAD, CALR, CARD11, CARMI, CASP8, CBFB, CBL, CCND1, CCND2, COND3, CCNE1, CCT6B, CD22, CD274, CD274 (PD-L1), CD276, CD36, CD58, CD70, CD79A, CD79B, CDC42, CDC73, CDH1, CDK12, CDK4, CDK6, CDK8, CDKN1A, CDKN1B, CDKN2A, CDKN2Ap14ARF, CDKN2Ap16INK4A, CDKN2B, CDKN2C, CEBPA, CENPA, CHD2, CHD4, CHEK1, CHEK2, CIC, CHITA, CKS1B, CPSI, CREBBP, CRKL, CRLF2, CSDE1, CSF1R, CSF3R, CTCF, CTLA-4, CTNN BI, CTNNA1, CTNNB1, CUL3, CUL4A, CUX1, CXCR4, CYLD, CYP17A1, CYSLTR2, DAXX, DCUN1D1, DDR1, DDR2, DDX3x, DH2, DICER1, DIS3, DNAJB1, DNM2, DNMT1, DNMT3A, DNMT3B, DOT1L, DROSHA, DTX1, DUSP2, DUSP4, DUSP9, E2F3, EBF1, ECT2L, EED, EGFL7, EGFR, EIF1AX, EIF4A2, EIF4E, ELF3, ELP2, EML4, EML4-

ALK, EP300, EPAS1, EPCAM, EPHA3, EPHA5, EPHA7, EPHB1, EPHB4, ERBB2, ERBB3, ERBB4, ERCC1, ERCC2, ERCC3, ERCC4, ERCC5, ERF, ERG, ERRF11, ERRFI1, ESR1, ETS1, ETV1, ETV4, ETV5, ETV6, EWSR1, EXOSC6, EZH1, EZH2, FAF1, FAM175A, FAM46C, FAM58A, FANCA, FANCC, FANCD2, FANCE, FANCE, FANCG, FANCI, FANCL, FAS, FAS (TNFRSF6), FAT1, FBXO11, FBXO31, FBXW7, FGF1, FGF10, FGF12, FGF14, FGF19, FGF2, FGF23, FGF3, FGF4, FGF5, FGF6, FGF7, FGF8, FGF9, FGFR1, FGFR2, FGFR3, FGFR4, FH, FHIT, FLCN, FLII, FLT1, FLT3, FLT4, FLYWCH1, FOXA1, FOXL2, FOXO1, FOXO3, FOXP1, FRS2, FUBP1, FYN, GABRA6, GADD45B, GATA1, GATA2, GATA3, GATA4, GATA6, GEN1, GID4 ((17orf 39), GID4 ((17orf39), GLI1, GLI1, GNA11, GNA12, GNA13, GNAQ, GNAS, GPR124, GPS2, GREM1, GRIN2A, GRM3, GSK3B, GTSE1, H3F3A, H3F3B, H3F3C, HDAC1, HDAC4, HDAC7, Hedgehog, HER-2 NEU; ERBB2, HGF, HIST1H1C, HIST1H1D, HIST1H1E, HIST1H2AC, HIST1H2AG, HIST1H2AL, HIST1H2AM, HIST1H2BC, HIST1H2BD, HIST1H2BJ, HIST1H2BK, HIST1H2BO, HIST1H3A, HIST1H3B, HIST1H3C, HIST1H3D, HIST1H3E, HIST1H3F, HIST1H3G, HIST1H3H, HIST1H3I, HIST1H3J, HIST2H3C, HIST2H3D, HIST3H3, HLA-A, HLA-B, HNF1A, HOXB13, HRAS, HSD3B1, HSP90AAI, ICK, ICOSLG, ID3, IDH1, IDH2, IFNGR1, IGF1, IGF1R, IGF2, IKBKE, IKZF1, IKZF2, IKZF3, IL10, IL7R, INHA, INHBA, INPP4A, INPP4B, INPP5D (SHIP), INPPL1, INSR, IRF1, IRF2, IRF4, IRF8, IRS1, IRS2, JAKI, JAK2, JAK3, JARID2, JUN, K14, KAT6A (MYST 3), KAT6A (MYST3), KDM2B, KDM4C, KDM5A, KDM5C, KDM6A, KDR, KEAP1, KEL, KIF5B, KIT, KLF4, KLHL6, KMT2A, KMT2A (MLL), KMT2B, KMT2C, KMT2C (MLL3), KMT2D, KMT2D (MLL2), KNSTRN, KRAS, LAMP1, LATS1, LATS2, LEF1, LMO1, LRP1B, LRRK2, LTK, LYN, LZTR1, MAF, MAFB, MAGED1, MAGI2, MALT1, MAP2K1, MAP2K1 (MEK1), MAP2K2, MAP2K2 (MEK2), MAP2K4, MAP3, MAP3K1, MAP3K13, MAP3K14, MAP3K6, MAP3K7, MAPK1, MAPK3, MAPKAP1, MAX, MCL1, MDC1, MDM2, MDM4, MED12, MEF2B, MEF2C, MEK1, MEN1, MERTK, MET, MGA, MIB1, MITF, MKI67, MKNK1, MLH1, MLLT3, MPL, MRE 11A, MRE11A, MSH2, MSH3, MSH6, MSI1, MSI2, MST1, MST1R, MTAP, MTOR, MUTYH, MYC, MYCL, MYCL (MYC L1), MYCL (MYCL1), MYCL1, MYCN, MYD88, MYO18A, MYOD1, NBN, NCOA3, NCOR1, NCOR2, NCSTN, NEGR1, NF1, NF2, NFE2L2, NFKBIA, NKX2-1, NKX3-1, NOD1, NOTCH1, NOTCH2, NOTCH3, NOTCH4, NPM1, NRAS, NRG1, NSD1, NT502, NTHL1, NTRK1, NTRK2, NTRK3, NUF2, NUP93, NUP98, P2RY8, PAG1, PAKI, PAK3, PAK7, PALB2, PARK2, PARP1, PARP2, PARP3, PASK, PAX3, PAX5, PAX7, PBRM1, PC, PCBP1, PCLO, PDCD1, PDCD1 (PD-1), PDCD11, PDCDILG2, PDCDILG2 (PD-L2), PDGFRA, PDGFRB, PDK1, PDPK1, PGR, PHF6, PHOX2B, PIK3C2B, PIK302G, PIK3C3, PIK3CA, PIK3CB, PIK3CD, PIK3CG, PIK3R1, PIK3R2, PIK3R3, PIM1, PLCG2, PLK2, PMAIP1, PMS1, PMS2, PNRC1, POLD1, POLE, POT1, PPARG, PPMID, PPP2, PPP2RIA, PPP2R2A, PPP4R2, PPP6C, PRDM1, PRDM14, PREX2, PRKAR1A, PRKC1, PRKD1, PRKDC, PRSS8, PTCH1, PTEN, PTP4A1, PTPN11, PTPN2, PTPN6 (SHP-1), PTPRD, PTPRO, PTPRS, PTPRT, QK1, RIA, RAB35, RAC1, RAC2, RAD21, RAD50, RAD51, RAD51B, RAD51C, RAD51D, RAD52, RAD54L, RAF1, RANBP2, RARA, RASA1, RASGEF1A, RB1, RBM10, RECOL, RECOL4, REL, RELN, RET, RFWD2, RHEB, RHOA, RICTOR, RIT1, RNF43, ROS1, RPS6KA4, RPS6KB1, RPS6KB2, RPTOR, RRAGC, RRAS, RRAS2, RTEL1, RUNX1, RUNX1T1, RXRA, RYBP, SIPR2, SDHA, SDHAF2, SDHB, SDHC, SDHD, SERP2, SESN1, SESN2, SESN3, SETBP1, SETD2, SETD8, SF3BI, SGK1, SH2B3, SH2DIA, SHOC2, SHQ1, SLIT2, SLX4, SMAD2, SMAD3, SMAD4, SMARCA1, SMARCA4, SMARCB1, SMARCD1, SMC1A, SMC3, SMO, SMYD3, SNCA1P, SOCS1, SOCS2, SOCS3, SOS1, SOX10, SOX17, SOX2, SOX9, SPEN, SPOP, SPRED1, SPTA1, SRC, SRSF2, STAG2, STAT3, STAT4, STATSA, STATSB, STAT6, STK11, STK19, STK40, SUFU, SUZI2, SYK, TAF1, TAP1, TAP2, TBL1XR1, TBX3, TCEB1, TCF3, TCF3 (E2A), TCF7L2, TCL1A (TCL1), TEK, TERC, TERT, TERT Promoter, TETI, TET2, TFRC, TGFBR1, TGFBR2, TIPARP, TLL2, TMEM127, TMEM30A, TMPRSS2, TMSB4XP8 (TMSL3), TNFAIP3, TNFRSF1IA, TNFRSF14, TNFRSF17, TOP1, TOP2A, TP53, TP53BPI, TP63, TRAF2, TRAF3, TRAF5, TRAF7, TSC1, TSC2, TSHR, TUSC3, TYK2, TYRO3, U2AF1, U2AF2, UPF1, VEGFA, VHL, VTCN1, WDR90, WHSC1, WHSC1 (MMSET or NSD2), WHSCIL1, WISP3, WT1, WWTR1, XBP1, XIAP, XPO1, XRCC2, YAP1, YES1, YY1AP1, ZBTB2, ZFHX3, ZMYM3, ZNF217, ZNF24 (ZSCAN3), ZNF703, ZRSR2, and any combination thereof.

In another embodiment, the genomic profile comprises one or more genes selected from the genes listed in Tables 1-16.

In one embodiment, TMB status based on genomic profiling is highly correlated with TMB status based on whole-exome or whole-genome sequencing. Evidence provided herein shows that the use of genomic profiling assays, such as the F1CDx assay, have concordance with whole-exome and/or whole genome sequencing assays. These data support the use of genomic profiling assays as a more efficient means of measuring TMB status, without forfeiting the prognostic qualities of TMB status.

TMB can be measured using a tissue biopsy sample or, alternatively, circulating tumor DNA (ctDNA), cfDNA (cell-free DNA), and/or a liquid biopsy sample. ctDNA can be used to measure TMB status according to whole-exome or whole-genome sequencing or genomic profiling using available methodologies, e.g., GRAIL, Inc.

A subject is identified as suitable for an immunotherapy, e.g., with an anti-PD-1 antibody or antigen-binding portion thereof or an anti-PD-L1 antibody or antigen-binding portion thereof, based on the measurement of TMB status and identification of a high TMB. In some embodiments, a TMB score is calculated as the total number of nonsynonymous missense mutations in a tumor, as measured by whole exome sequencing or whole genome sequencing. In one embodiment, the high TMB has a score of at least 210, at least 215, at least 220, at least 225, at least 230, at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, at least 400, at least 405, at least 410, at least 415, at least 420, at least 425, at least 430, at least 435, at least 440, at least 445, at least 450, at least 455, at least 460, at least 465, at least 470, at least 475, at least 480, at least 485, at least 490, at least 495, or at least 500. In another embodiment, the high TMB has a score of at least 215, at least 220, at least 221, at least 222, at least 223, at least 224, at least 225, at least 226, at least 227, at least 228, at least 229, at least 230, at least 231, at least 232, at least 233, at least 234, at least 235, at least 236, at least 237, at least 238, at least 239, at least 240, at least 241, at least 242, at least 243, at least 244, at least 245, at least 246, at least 247, at least 248, at least 249, or at least 250. In a particular embodiment, the high TMB has a score of at least 243. In other embodiments, the high TMB has a score of at least 244. In some embodiments, the high TMB has a score of at least 245. In other embodiments, the high TMB has a score of at least 246. In other embodiments, the high TMB has a score of at least 247. In other embodiments, the high TMB has a score of at least 248. In other embodiments, the high TMB has a score of at least 249. In other embodiments, the high TMB has a score of at least 250. In other embodiments, the high TMB has a score of any integer between 200 and 300 or higher. In other embodiments, the high TMB has a score of any integer between 210 and 290 or higher. In other embodiments, the high TMB has a score of any integer between 220 and 280 or higher. In other embodiments, the high TMB has a score of any integer between 230 and 270 or higher. In other embodiments, the high TMB has a score of any integer between 235 and 265 or higher.

Alternatively, the high TMB can be a relative value rather than an absolute value. In some embodiments, the subject's TMB status is compared to a reference TMB value. In one embodiment, the subject's TMB status is within the highest fractile of the reference TMB value. In another embodiment, the subject's TMB status is within the top tertile of the reference TMB value.

In some embodiments, TMB status is expressed as the number of mutations per sample, per cell, per exome, or per length of DNA (e.g., Mb). In some embodiments, a tumor has a high TMB status if the tumor has at least about 50 mutations/tumor, at least about 55 mutations/tumor, at least about 60 mutations/tumor, at least about 65 mutations/tumor, at least about 70 mutations/tumor, at least about 75 mutations/tumor, at least about 80 mutations/tumor, at least about 85 mutations/tumor, at least about 90 mutations/tumor, at least about 95 mutations/tumor, at least about 100 mutations/tumor, at least about 105 mutations/tumor, at least about 110 mutations/tumor, at least about 115 mutations/tumor, or at least about 120 mutations/tumor. In some embodiments, a tumor has a high TMB status if the tumor has at least about 125 mutations/tumor, at least about 150 mutations/tumor, at least about 175 mutations/tumor, at least about 200 mutations/tumor, at least about 225 mutations/tumor, at least about 250 mutations/tumor, at least about 275 mutations/tumor, at least about 300 mutations/tumor, at least about 350 mutations/tumor, at least about 400 mutations/tumor, or at least about 500 mutations/tumor. In one particular embodiment, a tumor has a high TMB status if the tumor has at least about 100 mutations/tumor.

In some embodiments, a tumor has a high TMB status if the tumor has at least about 5 mutations per megabase of genes, e.g., genome sequenced according to a TMB assay, e.g., genome sequenced according to a FOUNDATION-ONE® CDX™ assay, (mutations/Mb), at least about 6 mutations/Mb, at least about 7 mutations/Mb, at least about 8 mutations/Mb, at least about 9 mutations/Mb, at least about 10 mutations/Mb, at least about 11 mutations/Mb, at least about 12 mutations/Mb, at least about 13 mutations/Mb, at least about 14 mutations/Mb, at least about 15 mutations/Mb, at least about 20 mutations/Mb, at least about 25 mutations/Mb, at least about 30 mutations/Mb, at least about 35 mutations/Mb, at least about 40 mutations/Mb, at least about 45 mutations/Mb, at least about 50 mutations/Mb, at least about 75 mutations/Mb, or at least about 100 mutations/Mb. In certain embodiments, a tumor has a high TMB status if the tumor has at least about 5 mutations/Mb. In certain embodiments, a tumor has a high TMB status if the tumor has at least about 10 mutations/Mb. In some embodiments, a tumor has a high TMB status if the tumor has at least about 11 mutations/Mb. In some embodiments, a tumor has a high TMB status if the tumor has at least about 12 mutations/Mb. In some embodiments, a tumor has a high TMB status if the tumor has at least about 13 mutations/Mb. In some embodiments, a tumor has a high TMB status if the tumor has at least about 14 mutations/Mb. In certain embodiments, a tumor has a high TMB status if the tumor has at least about 15 mutations/Mb.

Because the number of mutations varies by tumor type and other ways (see Q4 and Q5), the values associated with "TMB high" and "TMB low" can differ across tumor types.

Non-Small Cell Lung Cancer

The present methods can treat a tumor at any stage. In certain embodiments, the tumor is derived from an NSCLC of any stage. There are at least seven stages used for NSCLC: occult (hidden) stage, Stage 0 (carcinoma in situ), Stage I, Stage II, Stage IIIA, Stage IIIB, and Stage IV. In the occult stage, the cancer cannot be seen by imaging or bronchoscopy. In Stage 0, cancer cells are found in the lining of the airways.

In one embodiment, the present methods treat a Stage I non-squamous NSCLC. Stage I NSCLC is divided in Stage IA and IB. In Stage IA, the tumor is in the lung only and is 3 centimeters or smaller. In Stage IB, the cancer has not spread to the lymph nodes and one or more of the following is true: 1) the tumor is larger than 3 centimeters but not larger than 5 centimeters; 2) the cancer has spread to the main bronchus and is at least 2 centimeters below where the trachea joins the bronchus; 3) cancer has spread to the innermost layer of the membrane that covers the lung; or 4) part of the lung has collapsed or developed pneumonitis (inflammation of the lung) in the area where the trachea joins the bronchus.

In another embodiment, the methods of the present disclosure treat a Stage II non-squamous NSCLC. Stage II NSCLC is divided into Stage IIA and IIB. In Stage IIA, the cancer has either spread to the lymph nodes or not. If the cancer has spread to the lymph nodes, then the cancer can only have spread to the lymph nodes on the same side of the chest as the tumor, the lymph nodes with cancer or within the lung or near the bronchus. and one or more of the following is true: 1) the tumor is not larger than 5 centimeters; 2) the cancer has spread to the main bronchus and is at least 2 centimeters below where the trachea joins the bronchus; 3) cancer has spread to the innermost layer of the membrane that covers the lung; or 4) part of the lung has collapsed or developed pneumonitis (inflammation of the lung) in the area where the trachea joins the bronchus. The tumor is also considered Stage IIA if the cancer has not spread to the lymph nodes and one or more of the following is true: 1) the tumor is larger than 5 centimeters but not larger than 7 centimeters; 2) the cancer has spread to the main bronchus and is at least 2 centimeters below where the trachea joins the bronchus; 3) cancer has spread to the innermost layer of the membrane that covers the lung; or 4) part of the lung has collapsed or developed pneumonitis (inflammation of the lung) in the area where the trachea joins the bronchus. In stage IIB, the cancer has either spread to the lymph nodes or not. If the cancer has spread to the lymph nodes, then the cancer can only have spread to the lymph nodes on the same side of the chest as the tumor, the lymph nodes with cancer are within the lung or near the bronchus and one or more of the following is true: 1) the tumor is larger than 5 centimeters but not larger than 7 centimeters; 2) the cancer has spread to the main bronchus and is at least 2 centimeters below where the trachea joins the bronchus; 3) cancer has spread to the innermost layer of the membrane that covers the lung; or 4) part of the lung has collapsed or developed pneumonitis (inflammation of the lung) in the area where the trachea joins the bronchus. The tumor is also considered Stage IIB if the cancer has not spread to the lymph nodes and one or more of the following is true: 1) the tumor is larger than 7 centimeters; 2) the cancer has spread to the main bronchus (and is at least 2 centimeters below where the trachea joins the bronchus), the chest wall, the diaphragm, or the nerve that controls the diaphragm; 3) cancer has spread to the membrane around the heart or lining the chest wall; 4) the whole lung has collapsed or developed pneumonitis (inflammation of the lung); or 5) there are one or more separate tumors in the same lobe of the lung.

In other embodiments, any methods of the present disclosure treats Stage III non-squamous NSCLC. Stage IIIA is divided into 3 sections. These 3 sections are based on 1) the size of the tumor; 2) where the tumor is found and 3) which (if any) lymph nodes have cancer. In the first type of Stage IIIA NSCLC, the cancer has spread to the lymph nodes on the same side of the chest as the tumor, and the lymph nodes with the cancer are near the sternum or where the bronchus enters the lung. Additionally: 1) the tumor may be any size; 2) part of the lung (where the trachea joins the bronchus) or the whole lung may have collapsed or developed pneumonitis (inflammation of the lung); 3) there may be one or more separate tumors in the same lobe of the lung; and 4) cancer can have spread to any of the following: a) main bronchus, but not the area where the trachea joins the bronchus, b) chest well, c) diaphragm and the nerve that controls it, d) membrane around the lung or lining the chest wall, e) membrane around the heart. In the second type of Stage IIIA NSCLC, the cancer has spread to the lymph nodes on the same side of the chest as the tumor, and the lymph nodes with the cancer are within the lung or near the bronchus. Additionally: 1) the tumor may be any size; 2) the whole lung may have collapsed or developed pneumonitis (inflammation of the lung); 3) there may be one or more separate tumors in the any of the lobes of the lung with cancer; and 4) cancer can have spread to any of the following: a) main bronchus, but not the area where the trachea joins the bronchus, b) chest well, c) diaphragm and the nerve that controls it, d) membrane around the lung or lining the chest wall, e) heart or the membrane around it, f) major blood vessels that lead to or from the heart, g) trachea, h) esophagus, i) nerve that controls the larynx (voice box), j) sternum (chest bone) or backbone, or k) carina (where the trachea joins the bronchi). In the third type of Stage IIIA NSCLC, the cancer has not spread to the lymph nodes, the tumor may be any size, and cancer has spread to any one of the following: a) heart, b) major blood vessels that lead to or from the heart, c) trachea, d) esophagus, e) nerve that controls the larynx (voice box), f) sternum (chest bone) or backbone, or g) carina (where the trachea joins the bronchi). Stage IIIB is divided into 2 sections depending on 1) the size of the tumor, 2) where the tumor is found, and 3) which lymph nodes have cancer. In the first type of Stage IIIB NSCLC, the cancer has spread to the lymph nodes on the opposite side of the chest as the tumor. Additionally, 1) the tumor may be any size; 2) part of the lung (where the trachea joins the bronchus) or the whole lung may have collapsed or developed pneumonitis (inflammation of the lung); 3) there may be one or more separate tumors in any of the lobs of the lung with cancer; and 4) cancer may have spread to any of the following: a) main bronchus, b) chest well, c) diaphragm and the nerve that controls it, d) membrane around the lung or lining the chest wall, e) heart or the membrane around it, f) major blood vessels that lead to or from the heart, g) trachea, h) esophagus, i) nerve that controls the larynx (voice box), j) sternum (chest bone) or backbone, or k) carina (where the trachea joins the bronchi). In the second type of Stage IIIB NSCLC, the cancer has spread to lymph nodes on the same side of the chest as the tumor. The lymph nodes with cancer are near the sternum (chest bone) or where the bronchus enters the lung. Additionally, 1) the tumor may be any size; 2) there may be separate tumors in different lobes of the same lung; and 3) cancer has spread to any of the following: a) heart, b) major blood vessels that lead to or from the heart, c) trachea, d) esophagus, e) nerve that controls the larynx (voice box), f) sternum (chest bone) or backbone, or g) carina (where the trachea joins the bronchi).

In some embodiments, the methods of the disclosure treat a Stage IV non-squamous NSCLC. In Stage IV NSCLC, the tumor may be any size and the cancer may have spread to the lymph nodes. One or more of the following is true in Stage IV NSCLC: 1) there are one or more tumors in both lungs; 2) cancer is found in the fluid around the lungs or heart; and 3) cancer has spread to other parts of the body, such as the brain, liver, adrenal glands, kidneys or bone.

In other embodiments, a NSCLC treatable by the present methods is squamous cell (epidermoid) carcinoma (squamous NSCLC). About 25% to 30% of all lung cancers are known to be squamous cell carcinomas. These cancers start in early versions of squamous cells, which are flat cells that line the inside of the airways in the lungs. They are often linked to a history of smoking and tend to be found in the central part of the lungs, near a main airway (bronchus).

In certain embodiments of the present methods, the anti-PD-1 antibody is nivolumab. In other embodiments, it is pembrolizumab. Typically, the anti-PD-1 antibodies are formulated for intravenous administration. In certain embodiments, the anti-PD-1 antibody is administered by intravenous infusion over a period of 60 minutes. In certain embodiments, the anti-PD-1 antibody is administered as a pharmaceutically acceptable formulation. In certain embodiments, the anti-PD-1 antibody or antigen-binding portion thereof is administered at a subtherapeutic dose.

Anti-PD-1 Antibodies or Anti-PD-L1 Antibodies Useful for the Disclosure

Anti-PD-1 antibodies that are known in the art can be used in the presently described compositions and methods. Various human monoclonal antibodies that bind specifically to PD-1 with high affinity have been disclosed in U.S. Pat. No. 8,008,449. Anti-PD-1 human antibodies disclosed in U.S. Pat. No. 8,008,449 have been demonstrated to exhibit one or more of the following characteristics: (a) bind to human PD-1 with a $K_D$ of $1 \times 10^{-7}$ M or less, as determined by surface plasmon resonance using a Biacore biosensor system; (b) do not substantially bind to human CD28, CTLA-4 or ICOS; (c) increase T-cell proliferation in a Mixed Lymphocyte Reaction (MLR) assay; (d) increase interferon-γ production in an MLR assay; (e) increase IL-2 secretion in an MLR assay; (f) bind to human PD-1 and cynomolgus monkey PD-1; (g) inhibit the binding of PD-L1 and/or PD-L2 to PD-1; (h) stimulate antigen-specific memory responses; (i) stimulate antibody responses; and (j) inhibit tumor cell growth in vivo. Anti-PD-1 antibodies usable in the present disclosure include monoclonal antibodies that bind specifically to human PD-1 and exhibit at least one, in some embodiments, at least five, of the preceding characteristics.

Other anti-PD-1 monoclonal antibodies have been described in, for example, U.S. Pat. Nos. 6,808,710, 7,488, 802, 8,168,757 and 8,354,509, US Publication No. 2016/0272708, and PCT Publication Nos. WO 2012/145493, WO 2008/156712, WO 2015/112900, WO 2012/145493, WO 2015/112800, WO 2014/206107, WO 2015/35606, WO 2015/085847, WO 2014/179664, WO 2017/020291, WO 2017/020858, WO 2016/197367, WO 2017/024515, WO 2017/025051, WO 2017/123557, WO 2016/106159, WO 2014/194302, WO 2017/040790, WO 2017/133540, WO 2017/132827, WO 2017/024465, WO 2017/025016, WO 2017/106061, WO 2017/19846, WO 2017/024465, WO 2017/025016, WO 2017/132825, and WO 2017/133540 each of which is incorporated by reference in its entirety.

In some embodiments, the anti-PD-1 antibody is selected from the group consisting of nivolumab (also known as OPDIVO®, 5C4, BMS-936558, MDX-1106, and ONO-4538), pembrolizumab (Merck; also known as KEYTRUDA®, lambrolizumab, and MK-3475; see WO2008/156712), PDR001 (Novartis; see WO 2015/112900), MEDI-0680 (AstraZeneca; also known as AMP-514; see WO 2012/145493), cemiplimab (Regeneron; also known as REGN-2810; see WO 2015/112800), JS001 (TAIZHOU JUNSHI PHARMA; see Si-Yang Liu et al., *J. Hematol. Oncol.* 10:136 (2017)), BGB-A317 (Beigene; see WO 2015/35606 and US 2015/0079109), INCSHR1210 (Jiangsu Hengrui Medicine; also known as SHR-1210; see WO 2015/085847; Si-Yang Liu et al., *J. Hematol. Oncol.* 10:136 (2017)), TSR-042 (Tesaro Biopharmaceutical; also known as ANB011; see WO2014/179664), GLS-010 (Wuxi/Harbin Gloria Pharmaceuticals; also known as WBP3055; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/040790), MGA012 (Macrogenics, see WO 2017/19846), and IBI308 (Innovent; see WO 2017/024465, WO 2017/025016, WO 2017/132825, and WO 2017/133540).

In one embodiment, the anti-PD-1 antibody is nivolumab. Nivolumab is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2 (9): 846-56).

In another embodiment, the anti-PD-1 antibody is pembrolizumab. Pembrolizumab is a humanized monoclonal IgG4 (S228P) antibody directed against human cell surface receptor PD-1 (programmed death-1 or programmed cell death-1). Pembrolizumab is described, for example, in U.S. Pat. Nos. 8,354,509 and 8,900,587.

Anti-PD-1 antibodies usable in the disclosed compositions and methods also include isolated antibodies that bind specifically to human PD-1 and cross-compete for binding to human PD-1 with any anti-PD-1 antibody disclosed herein, e.g., nivolumab (see, e.g., U.S. Pat. Nos. 8,008,449 and 8,779,105; WO 2013/173223). In some embodiments, the anti-PD-1 antibody binds the same epitope as any of the anti-PD-1 antibodies described herein, e.g., nivolumab. The ability of antibodies to cross-compete for binding to an antigen indicates that these monoclonal antibodies bind to the same epitope region of the antigen and sterically hinder the binding of other cross-competing antibodies to that particular epitope region. These cross-competing antibodies are expected to have functional properties very similar those of the reference antibody, e.g., nivolumab, by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 antibody, nivolumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-1 antibodies usable in the compositions and methods of the disclosed disclosure also include antigen-binding portions of the above antibodies. It has been amply demonstrated that the antigen-binding function of an antibody can be performed by fragments of a full-length antibody.

Anti-PD-1 antibodies suitable for use in the disclosed compositions and methods are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and up-regulating the immune system. In certain embodiments, the anti-PD-1 antibody or antigen-binding portion thereof cross-competes with nivolumab for binding to human PD-1.

Anti-PD-1 Antibodies or Anti-PD-L1 Antibodies Useful for the Disclosure

In certain embodiments, an anti-PD-1 antibody used in the methods can be replaced with another PD-1 or anti-PD-L1 antagonist. For example, because an anti-PD-L1 antibody prevents interaction between PD-1 and PD-L1, thereby exerting similar effects to the signaling pathway of PD-1, an anti-PD-L1 antibody can replace the use of an anti-PD-1 antibody in the methods disclosed herein. Anti-PD-L1 antibodies that are known in the art can be used in the compositions and methods of the present disclosure. Examples of anti-PD-L1 antibodies useful in the compositions and methods of the present disclosure include the antibodies disclosed in U.S. Pat. No. 9,580,507. Anti-PD-L1 human monoclonal antibodies disclosed in U.S. Pat. No. 9,580,507 have been demonstrated to exhibit one or more of the following characteristics: (a) bind to human PD-L1 with a $K_D$ of $1 \times 10^{-7}$ M or less, as determined by surface plasmon resonance using a Biacore biosensor system; (b) increase T-cell proliferation in a Mixed Lymphocyte Reaction (MLR) assay; (c) increase interferon-γ production in an MLR assay; (d) increase IL-2 secretion in an MLR assay; (e) stimulate antibody responses; and (f) reverse the effect of T regulatory cells on T cell effector cells and/or dendritic cells. Anti-PD-L1 antibodies usable in the present disclosure include monoclonal antibodies that bind specifically to human PD-L1 and exhibit at least one, in some embodiments, at least five, of the preceding characteristics.

In certain embodiments, the anti-PD-L1 antibody is selected from the group consisting of BMS-936559 (also known as 12A4, MDX-1105; see, e.g., U.S. Pat. No. 7,943, 743 and WO 2013/173223), atezolizumab (Roche; also known as TECENTRIQ®; MPDL3280A, RG7446; see U.S. Pat. No. 8,217,149; see, also, Herbst et al. (2013) J Clin Oncol 31 (suppl): 3000), durvalumab (AstraZeneca; also known as IMFINZI™, MEDI-4736; see WO 2011/066389), avelumab (Pfizer; also known as BAVENCIO®, MSB-0010718C; see WO 2013/079174), STI-1014 (Sorrento; see WO2013/181634), CX-072 (Cytomx; see WO2016/149201), KN035 (3D Med/Alphamab; see Zhang et al., *Cell Discov.* 7:3 (March 2017), LY3300054 (Eli Lilly Co.; see, e.g., WO 2017/034916), and CK-301 (Checkpoint Therapeutics; see Gorelik et al., AACR: Abstract 4606 (April 2016)).

In certain embodiments, the PD-L1 antibody is atezolizumab (TECENTRIQ®). Atezolizumab is a fully humanized IgG1 monoclonal anti-PD-L1 antibody.

In certain embodiments, the PD-L1 antibody is durvalumab (IMFINZI™). Durvalumab is a human IgG1 kappa monoclonal anti-PD-L1 antibody.

In certain embodiments, the PD-L1 antibody is avelumab (BAVENCIO®). Avelumab is a human IgG1 lambda monoclonal anti-PD-L1 antibody.

In other embodiments, the anti-PD-L1 monoclonal antibody is selected from the group consisting of 28-8, 28-1, 28-12, 29-8, 5H1, and any combination thereof.

Anti-PD-L1 antibodies usable in the disclosed compositions and methods also include isolated antibodies that bind specifically to human PD-L1 and cross-compete for binding to human PD-L1 with any anti-PD-L1 antibody disclosed herein, e.g., atezolizumab, durvalumab, and/or avelumab. In some embodiments, the anti-PD-L1 antibody binds the same epitope as any of the anti-PD-L1 antibodies described herein, e.g., atezolizumab, durvalumab, and/or avelumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., atezolizumab and/or avelumab, by virtue of their binding to the same epitope region of PD-L1. Cross-competing antibodies can be readily identified based on their ability to cross-compete with atezolizumab and/or avelumab in standard PD-L1 binding assays such as Biacore analysis, ELISA assays or flow cytometry (see, e.g., WO 2013/173223).

In certain embodiments, the antibodies that cross-compete for binding to human PD-L1 with, or bind to the same epitope region of human PD-L1 antibody as, atezolizumab, durvalumab, and/or avelumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-L1 antibodies usable in the compositions and methods of the disclosed disclosure also include antigen-binding portions of the above antibodies. It has been amply demonstrated that the antigen-binding function of an antibody can be performed by fragments of a full-length antibody.

Anti-PD-L1 antibodies suitable for use in the disclosed compositions and methods are antibodies that bind to PD-L1 with high specificity and affinity, block the binding of PD-1, and inhibit the immunosuppressive effect of the PD-1 signaling pathway. In any of the compositions or methods disclosed herein, an anti-PD-L1 "antibody" includes an antigen-binding portion or fragment that binds to PD-L1 and exhibits the functional properties similar to those of whole antibodies in inhibiting receptor binding and up-regulating the immune system. In certain embodiments, the anti-PD-L1 antibody or antigen-binding portion thereof cross-competes with atezolizumab, durvalumab, and/or avelumab for binding to human PD-L1.

Standard-of-Care Therapies for Lung Cancer

Standard-of-care therapies for different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard-of-care treatments for a wide variety of cancers (see NCCN GUIDELINES® (2014), available at: nccn.org/professionals/physician_gls/f_guidelines.asp, last accessed May 14, 2014).

NSCLC is the leading cause of cancer death in the U.S. and worldwide, exceeding breast, colon and prostate cancer combined. In the U.S., an estimated 228, 190 new cases of lung and bronchial will be diagnosed in the U.S., and some 159,480 deaths will occur because of the disease (Siegel et al. (2014) (A Cancer J Clin 64 (1): 9-29). The majority of patients (approximately 78%) are diagnosed with advanced/recurrent or metastatic disease. Metastases to the adrenal gland from lung cancer are a common occurrence, with about 33% of patients having such metastases. NSCLC therapies have incrementally improved OS, but benefit has reached a plateau (median OS for late stage patients is just 1 year). Progression after IL therapy occurred in nearly all of these subjects and the 5-year survival rate is only 3.6% in the refractory setting. From 2005 to 2009, the overall 5-year relative survival rate for lung cancer in the U.S. was 15.9% (NCCN GUIDELINES®, Version 3.2014—Non-Small Cell Lung Cancer, available at: nccn.org/professionals/physician_gls/pdf/nscl.pdf, last accessed May 14, 2014).

Surgery, radiation therapy (RT) and chemotherapy are the three modalities commonly used to treat NSCLC patients. As a class, NSCLCs are relatively insensitive to chemotherapy and RT, compared to small cell carcinoma. In general, for patients with Stage I or II disease, surgical resection provides the best chance for cure, with chemotherapy increasingly being used both pre-operatively and post-operatively. RT can also be used as adjuvant therapy for patients with resectable NSCLC, the primary local treatment, or as palliative therapy for patients with incurable NSCLC.

Patients with Stage IV disease who have a good performance status (PS) benefit from chemotherapy. Many drugs, including platinum agents (e.g., cisplatin, carboplatin), taxanes agents (e.g., paclitaxel, albumin-bound paclitaxel, docetaxel), vinorelbine, vinblastine, etoposide, pemetrexed and gemcitabine are useful for Stage IV NSCLC. Combinations using many of these drugs produce 1-year survival rates of 30% to 40% and are superior to single agents. Specific targeted therapies have also been developed for the treatment of advanced lung cancer. For example, bevacizumab (AVASTIN®) is a monoclonal antibody that blocks vascular endothelial growth factor A (VEGF-A). Erlotinib (TARCEVA®) is a small-molecule TKI of epidermal growth factor receptor (EGFR). Crizotinib (XALKORI®) is a small-molecule TKI that targets ALK and MET, and is used to treat NSCLC in patients carrying the mutated ALK fusion gene. Cetuximab (ERBITUX®) is a monoclonal antibody that targets EGFR.

There is a particular unmet need among patients who have squamous cell NSCLC (representing up to 25% of all NSCLC) as there are few treatment options after first line (IL) therapy. Single-agent chemotherapy is standard of care following progression with platinum-based doublet chemotherapy (Pt-doublet), resulting in median OS of approximately 7 months. Docetaxel remains the benchmark treatment in this line of therapy although erlotinib can also be used with less frequency. Pemetrexed has also been shown to produce clinically equivalent efficacy outcomes but with significantly fewer side effects compared with docetaxel in the second line (2L) treatment of patients with advanced NSCLC (Hanna et al. (2004) J Clin Oncol 22:1589-97). No therapy is currently approved for use in lung cancer beyond the third line (3L) setting. Pemetrexed and bevacizumab are not approved in squamous NSCLC, and molecularly targeted therapies have limited application. The unmet need in advanced lung cancer has been compounded by the recent failure of Oncothyreon and Merck KgaA's STIMUVAX® to improve OS in a phase 3 trial, inability of ArQule's and Daiichi Sankyo's c-Met kinase inhibitor, tivantinib, to meet survival endpoints, failure of Eli Lilly's ALIMTA® in combination with Roche's AVASTIN® to improve OS in a late-stage study, and Amgen's and Takeda Pharmaceutical's failure to meet clinical endpoints with the small-molecule VEGF-R antagonist, motesanib, in late-stage trials.

Immunotherapy of Lung Cancer

A clear need exists for effective agents for patients who have progressed on multiple lines of targeted therapy, as well as for therapies that extend survival for longer periods beyond the current standard treatments. Newer approaches involving immunotherapy, especially blockade of immune checkpoints including the CTLA-4, PD-1, and PD-L1 inhibitory pathways, have recently shown promise (Creelan et al. (2014) Cancer Control 21 (1): 80-89). However, a need remains to identify patients that may be more responsive to immunotherapy, in particular to identify patients that are more likely to respond to an anti-PD-1 or anti-PD-L1 antibody therapy.

Pharmaceutical Compositions and Dosages

Therapeutic agents of the present disclosure can be constituted in a composition, e.g., a pharmaceutical composition containing one or more antibodies and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. In one embodiment, the carrier for a composition containing an antibody is suitable for intravenous, intramuscular, subcutaneous, parenteral, spinal or epidermal administration (e.g., by injection or infusion). A pharmaceutical composition of the disclosure can include one or more pharmaceutically acceptable salts, anti-oxidant, aqueous and non-aqueous carriers, and/or adjuvants such as preservatives, wetting agents, emulsifying agents and dispersing agents.

The present disclosure provides dosage regimens that can provide a desired response, e.g., a maximal therapeutic response and/or minimal adverse effects. For administration of an anti-PD-1 antibody, the dosage can range from about 0.01 to about 10 mg/kg, about 1 to about 9 mg/kg, about 2 to about 8 mg/kg, about 3 to about 7 mg/kg, about 3 to about 6 mg/kg, 0.01 to about 5 mg/kg, or about 1 to about 3 mg/kg of the subject's body weight. For example, dosages can be about 0.1, about 0.3, about 1, about 2, about 3, about 4, about 5, about 6, about 7, about 8, about 9, or about 10 mg/kg body weight. The dosing schedule is typically designed to achieve exposures that result in sustained receptor occupancy (RO) based on typical pharmacokinetic properties of an antibody. An exemplary treatment regime entails administration once about per week, once about every 2 weeks, once about every 3 weeks, once about every 4 weeks, once about every month, once about every 3-6 months or longer. In certain embodiments, an anti-PD-1 antibody such as nivolumab is administered to the subject once about every 2 weeks. The anti-PD-1 antibody can be administered in at least two doses, each of the doses is at an amount of about 0.01 mg/kg to about 5 mg/kg, e.g., 3 mg/kg, at a dosing interval of every two weeks between the two doses. In some embodiments, the anti-PD-1 antibody is administered in at least three, four, five, six, or seven doses (i.e., multiple doses), each of the doses is at an amount of about 0.01 mg/kg to about 10 mg/kg, e.g., 1 mg/kg, 3 mg/kg, or 6 mg/kg, at a dosing interval of every two weeks between two adjacently given doses. The dosage and scheduling can change during a course of treatment. In one embodiment, a dosage regimen for an anti-PD-1 antibody of the disclosure comprises about 0.1 to about 5 mg/kg body weight, about 1 to about 5 mg/kg body weight, or about 1 to about 3 mg/kg body weight via intravenous administration, with the antibody being given every about 14-21 days in up to about 6-week or about 12-week cycles until complete response or confirmed progressive disease. In some embodiments, the antibody treatment, or any combination treatment disclosed herein, is continued for at least about 1 month, at least about 3 months, at least about 6 months, at least about 9 months, at least about 1 year, at least about 18 months, at least about 24 months, at least about 3 years, at least about 5 years, or at least about 10 years.

For administration of an anti-PD-L1 antibody, the dosage can range from about 1 to about 20 mg/kg, about 1 to about 19 mg/kg, about 2 to about 18 mg/kg, about 3 to about 17 mg/kg, about 3 to about 16 mg/kg, about 4 to about 15 mg/kg, about 5 to about 14 mg/kg, about 6 to about 13 mg/kg, about 7 to about 12 mg/kg, or about 8 to about 12 mg/kg of the subject's body weight. For example, dosages can be about 1, about 2, about 3, about 4, about 5, about 6, about 7, about 8, about 9, about 10, about 11, about 12, about 13, about 14, about 15, about 16, about 17, or about 18 mg/kg body weight. The dosing schedule is typically designed to achieve exposures that result in sustained receptor occupancy (RO) based on typical pharmacokinetic properties of an antibody. An exemplary treatment regime entails administration once about per week, once about every 2 weeks, once about every 3 weeks, once about every 4 weeks, once about every month, once about every 3-6 months or longer. In certain embodiments, an anti-PD-L1 antibody is administered to the subject once about every 2 weeks. The anti-PD-L1 antibody can be administered in at least two doses, each of the doses is at an amount of about 6 mg/kg to about 18 mg/kg, e.g., 10 mg/kg, at a dosing interval of every two weeks between the two doses. In some embodiments, the anti-PD-1 antibody is administered in at least three, four, five, six, or seven doses (i.e., multiple doses), each of the doses is at an amount of about 6 mg/kg to about 18 mg/kg, e.g., 10 mg/kg or 15 mg/kg, at a dosing interval of every two weeks between two adjacently given doses. The dosage and scheduling can change during a course of treatment. In one embodiment, a dosage regimen for an anti-PD-L1 antibody of the disclosure comprises about 1 to about 18 mg/kg body weight, about 6 to about 15 mg/kg body weight, or about 10 to about 15 mg/kg body weight via intravenous administration, with the antibody being given every about 14-21 days in up to about 6-week or about 12-week cycles until complete response or confirmed progressive disease. In some embodiments, the antibody treatment, or any combination treatment disclosed herein, is continued for at least about 1 month, at least about 3 months, at least about 6 months, at least about 9 months, at least about 1 year, at least about 18 months, at least about 24 months, at least about 3 years, at least about 5 years, or at least about 10 years.

When used in combinations with other therapies (e.g., other immunotherapies), the dosage of an anti-PD-1 antibody can be lowered compared to the monotherapy dose. Dosages of nivolumab that are lower than the typical 3 mg/kg, but not less than 0.001 mg/kg, are subtherapeutic dosages. The subtherapeutic doses of an anti-PD-1 antibody used in the methods herein are higher than 0.001 mg/kg and lower than 3 mg/kg. In some embodiments, a subtherapeutic dose is about 0.001 mg/kg-about 1 mg/kg, about 0.01 mg/kg-about 1 mg/kg, about 0.1 mg/kg-about 1 mg/kg, or about 0.001 mg/kg-about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%) (Brahmer et al. (2010) J Clin Oncol 28:3167-75). Thus, 0.3 mg/kg dosing can allow for sufficient exposure to lead to maximal biologic activity.

In some embodiments of the disclosure, the anti-PD-1 antibody is administered at a dose of 3 mg/kg. In other embodiments of the disclosure, the anti-PD-1 antibody is administered at a dose of 1 mg/kg.

In certain embodiments, the dose of an anti-PD-1 antibody (or an anti-PD-L1 antibody) is a flat dose in a pharmaceutical composition. In other embodiments, the method of the present disclosure can be used with a flat dose (a dose given to a patient irrespective of the body weight of the patient). In some embodiments, the flat dose of the anti-PD-1 antibody or antigen binding portion thereof is at least about 100 mg, 120 mg, 140 mg, 160 mg, 180 mg, 200 mg, 220 mg, 240 mg, 260 mg, 280 mg, 300 mg, 400 mg, 420 mg, 440 mg, 460 mg, 480 mg, 500 mg, 520 mg, 540 mg, 560 mg, 600 mg, 640 mg, 680 mg, 720 mg, 760 mg, 800 mg, 840 mg, 880 mg, 920 mg, 960 mg, 1000 mg, 1040 mg, 1080 mg, 1120 mg, 1160 mg, or 1200 mg. For example, a flat dose of a nivolumab can be about 240 mg. For example, a flat dose of pembrolizumab can be about 200 mg. In embodiments, the anti-PD-1 antibody or antigen-binding portion thereof is administered at a dose of about 240 mg. In embodiments, the anti-PD-1 antibody or antigen-binding portion thereof is administered at a dose of about 360 mg. In embodiments, the anti-PD-1 antibody or antigen-binding portion thereof is administered at a dose of about 480 mg. In embodiments, the flat dose of the anti-PD-1 antibody or antigen binding portion thereof is administered once about every week, every two weeks, every three weeks, every four weeks, every five weeks, or every six weeks. In one embodiment, 240 mg of the anti-PD-1 antibody or antigen binding fragment is administered once every 2 weeks. In another embodiment, 360 mg of the anti-PD-1 antibody or antigen binding fragment is administered once every 3 weeks. In another embodiment, 480 mg of the anti-PD-1 antibody or antigen binding fragment is administered once every 4 weeks.

In some embodiments, the flat dose of the anti-PD-L1 antibody or antigen binding portion thereof is at least about 600 mg, 620 mg, 640 mg, 660 mg, 680 mg, 700 mg, 720 mg, 740 mg, 760 mg, 780 mg, 800 mg, 820 mg, 840 mg, 860 mg, 880 mg, 900 mg, 920 mg, 940 mg, 960 mg, 1000 mg, 1040 mg, 1080 mg, 1120 mg, 1160 mg, 1200 mg, 1240 mg, 1280 mg, 1320 mg, 1360 mg, 1400 mg, 1440 mg, 1480 mg, 1520 mg, 1560 mg, 1600 mg, 1640 mg, 1680 mg, 1720 mg, 1760 mg, or 1800 mg. For example, a flat dose of a atezolizumab (TECENTRIQ®) can be about 1200 mg. For example, a flat dose of durvalumab (IMFINZI®) can be about 800 mg. For example, a flat dose of avelumab (BAVENCIO®) can be about 800 mg. In embodiments, the anti-PD-L1 antibody or antigen-binding portion thereof is administered at a dose of about 800 mg. In embodiments, the anti-PD-L1 antibody or antigen-binding portion thereof is administered at a dose of about 1200 mg. In embodiments, the anti-PD-L1 antibody or antigen-binding portion thereof is administered at a dose of about 1600 mg. In some embodiments, the flat dose of the anti-PD-L1 antibody or antigen binding portion thereof is administered once about every week, every two weeks, every three weeks, every four weeks, every five weeks, or every six weeks. In one embodiment, about 800 mg of the anti-PD-L1 antibody or antigen binding fragment is administered once every 2 weeks. In another embodiment, about 1200 mg of the anti-PD-L1 antibody or antigen binding fragment is administered once every 4 weeks.

Dosage and frequency vary depending on the half-life of the antibody in the subject. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is typically administered at relatively infrequent intervals over a long period of time. Some patients continue to receive treatment for the rest of their lives. In therapeutic applications, a relatively high dosage at relatively short intervals is sometimes required until progression of the disease is reduced or terminated, or until the patient shows partial or complete amelioration of symptoms of disease. Thereafter, the patient can be administered a prophylactic regime.

Actual dosage levels of the active ingredients in the pharmaceutical compositions of the present disclosure can be varied so as to obtain an amount of the active ingredient that is effective to achieve the desired therapeutic response for a particular patient, composition, and mode of administration, without being unduly toxic to the patient. The selected dosage level will depend upon a variety of pharmacokinetic factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present disclosure can be administered via one or more routes of administration using one or more of a variety of methods well known in the art. As will be appreciated by the skilled artisan, the route and/or mode of administration will vary depending upon the desired results.

Kits

Also within the scope of the present disclosure are kits comprising an anti-PD-1 antibody or an anti-PD-L1 antibody. Kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a tumor, the kit comprising: (a) a dosage ranging from about 4 mg to about 500 mg of an anti-PD-1 antibody; and (b) instructions for using the anti-PD-1 antibody in any method described herein. In certain embodiments for treating human patients, the kit comprises an anti-human PD-1 antibody disclosed herein, e.g., nivolumab or pembrolizumab. In some embodiments, the kit further comprises an anti-PD-L1 antibody. In some embodiments, the kit further comprises instructions for detecting the mutation status of STK11 in a tumor sample. In other embodiments, the kit further comprises instructions for detecting the expression of PD-L1 in a tumor sample.

The present disclosure is further illustrated by the following example that should not be construed as further limiting. The contents of all references cited throughout this application are expressly incorporated herein by reference.

Example 1

STK11 Mutation as a Biomarker for Nivolumab Response

PD-L1 is expressed in NSCLC tumors, e.g., commercial NSCLC tumors, according to different patterns of expressing (FIG. 1). These patterns were designated as diffuse, heterogenous, tumor-stroma interface, and negative. PD-L1 expression patterns can be linked to mechanistic hypotheses. For example, in tumors with diffuse patterns, the expression of PD-L1 is driven by 9p24 amplification in oncogenic signaling pathway instead of being driven by mutation. In tumors with tumor-stroma interface patterns, there are adaptive resistances instead of epithelial to mesenchymal transition (EMT).

Figure 2B:
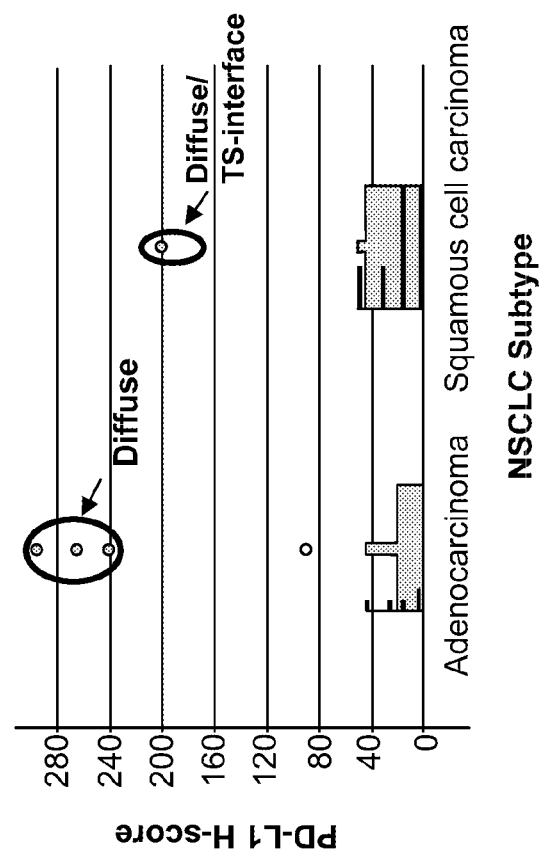
FIGS. 2A-2B shows the distribution of PD-L1 H-scores in each PD-L1 pattern as shown in FIGS. 1A-1D, i.e., diffuse (D), heterogeneous (H), negative (N), and tumor-stroma interface (T) (FIG. 2A), and the distribution of PD-L1 H-scores in two NSCLC subtypes, namely adenocarcinoma and squamous cell carcinoma (FIG. 2D).
Figure 2A:
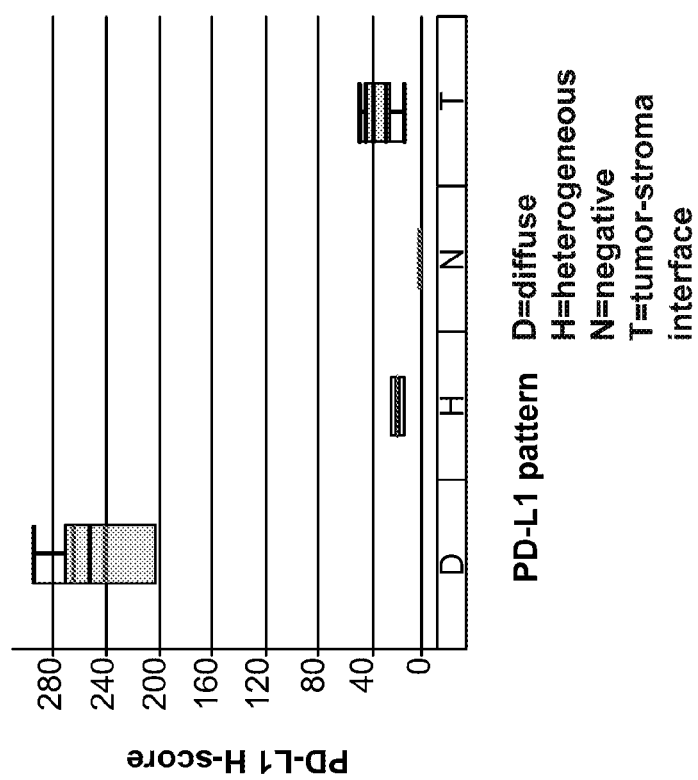

Patterns of PD-L1 expression in NSCLC commercial tumors correlate with PD-L1 H-score, as shown in FIG. 2. There is a substantial difference in the level of PD-L1 expression according to each pattern. For example, very high H-scores were observed in diffuse pattern samples, which suggested a potential dependence of these tumors on PD-L1 inhibition.

The PD-L1 expression patterns observed in NSCLC commercial tumors were also observed in biopsies. FIG. 3 shows PD-L1 expression patterns in trial biopsies corresponding to patients treated with nivolumab monotherapy, which corresponding to the same patterns observed in NSCLC commercial tumors.

The potential for false negative PD-L1 is impacted by pattern category, preanalytic variables, and by the size of the biopsy. For example, tumor-stroma interface patterns are heterogeneous and particularly susceptible to false negative results. Accordingly, there is a need for biomarkers that can facilitate the classification of NSCLC tumors, which in turn could be used to predict the tumor response to a certain therapeutic agent.

Figure 4:
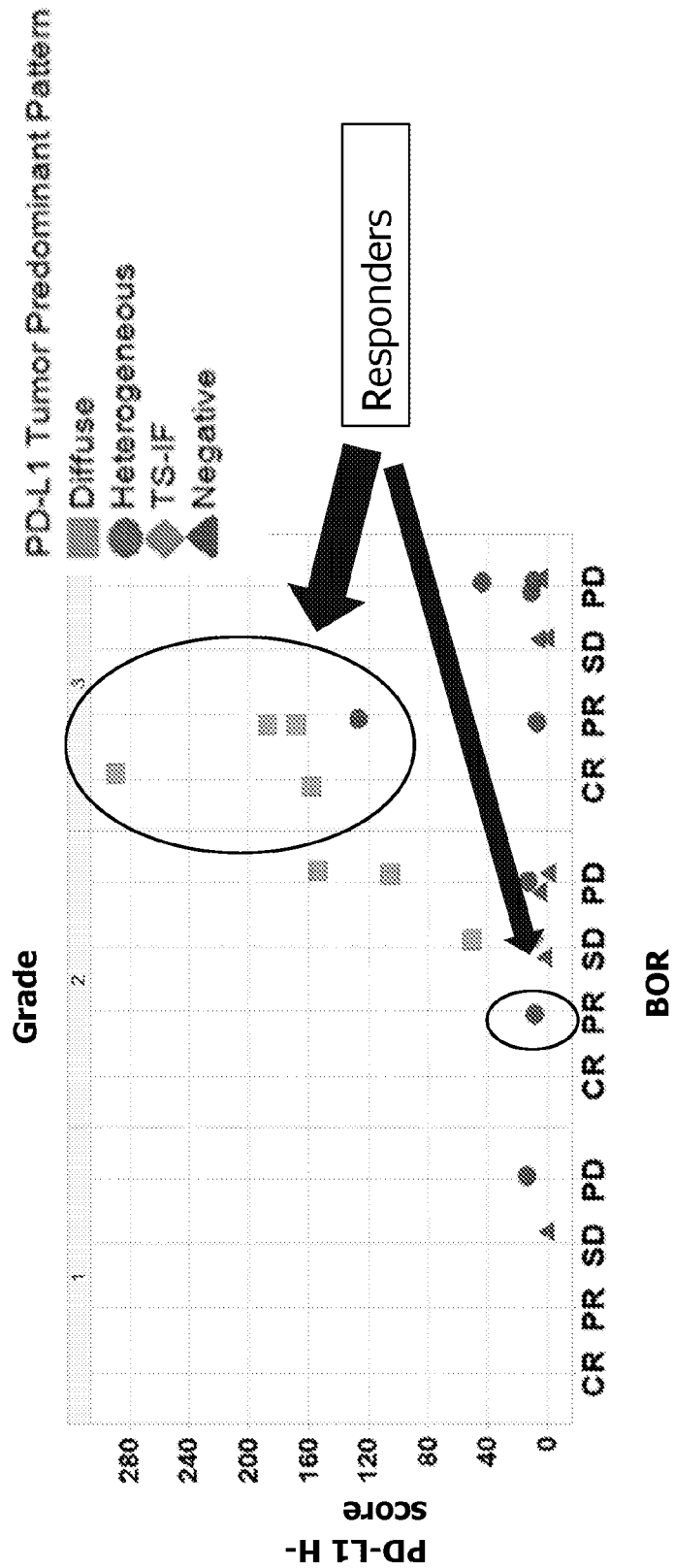
FIG. 4 shows the PD-L1 H-score of patients undergoing nivolumab monotherapy. The predominant PD-L1 pattern in the majority of complete responders (CR) and partial responders (PR) is the diffuse pattern.

A correlation between patterns of PD-L1 expression and nivolumab efficacy was observed (FIG. 4). Most of complete responders in Grade 3 tumors had a diffuse pattern of PD-L1 expression, and high PD-L1 H-score. Accordingly, the identification of biomarkers specific for the diffuse PD-L1 expression pattern could be used to identify patients suitable for treatment for nivolumab based on the presence/absence of that biomarker.

The immune infiltrate can be potentially used as biomarker specific for NSCLC tumors with diffuse expression patterns (FIG. 5), since in the commercial NSCLC tumors used to generate the data presented in FIG. 5, those with diffuse or heterogeneous PD-L1 patterns were associated with more abundant immune infiltrate (higher PD-L1 H-score).

Figure 6:
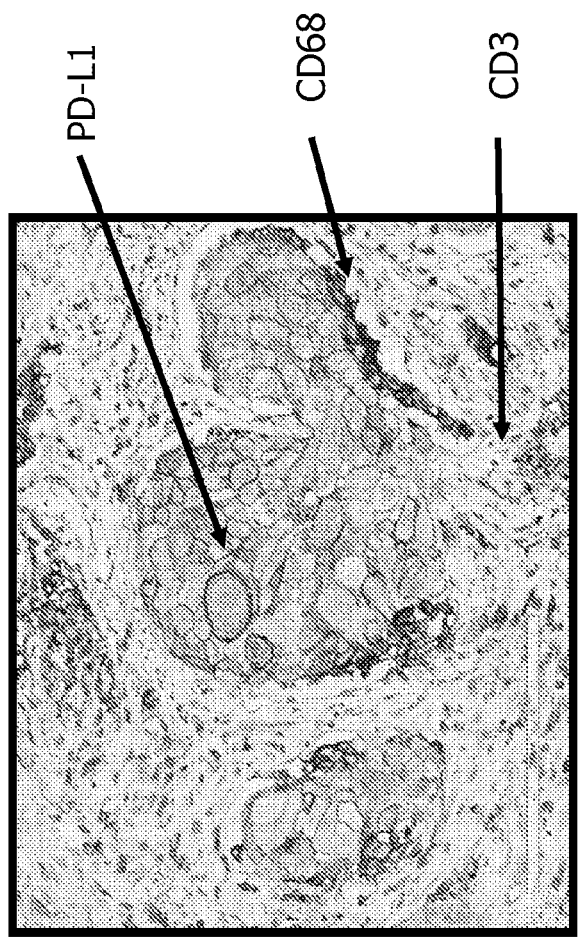
FIG. 6 presents a multiplexed IHC image stained for PD-L1, CD68, and CD3.

Multiplex IHC experiments showed defined special relationships between the tumor cells and immune cell subsets. PD-L1 labeling showed diffuse PD-L1 expression in the tumor. CD68 detection indicated that a layer of macrophages at the tumor-stroma interface contribute to the formation of a "barrier" activated T-cells, whereas CD3 detection indicated that T-cells are moderately abundant but largely confined to the stroma (FIG. 6).

PD-L1 expression patterns correlate with genomic data (FIG. 7). FIG. 7, panel A, shows that the level of PD-L1 expression correlates with RNA sequencing data, but RNA sequencing data alone does not provide geographical context for the PD-L1 expression patterns observed via IHC. FIG. 7, panel B, which presents exome sequencing data shows that a PD-L1 diffuse expression pattern correlates with a higher mutation load.

Figure 8B:
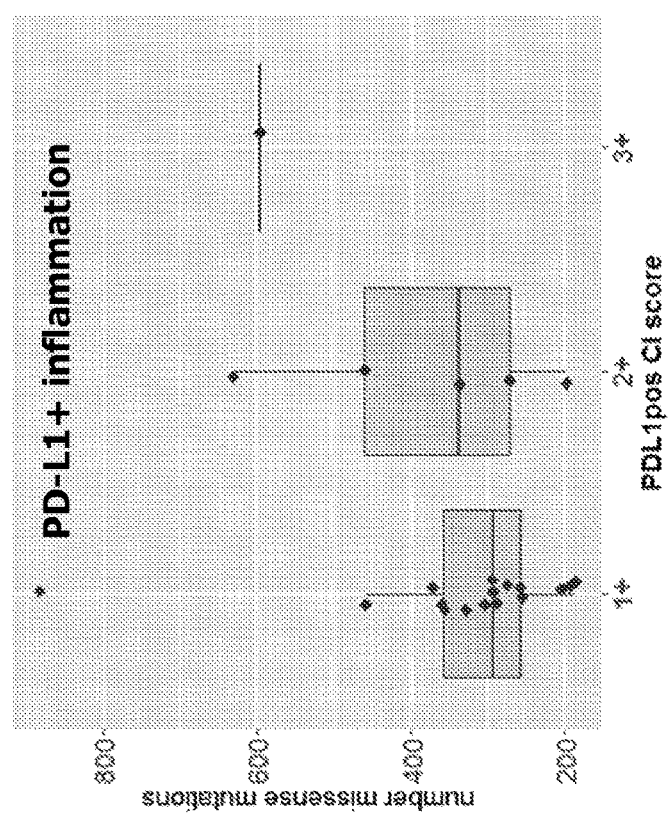
FIGS. 8A-8B show the relationship between the number of missense mutations in NSCLC tumors versus overall inflammation as measured by the CI Score (FIG. 8A), and the relationship between the number of missense mutation in NSCLC tumors versus PD-L1+inflammation as measured by the PDLP1pos CI Score (FIG. 8B).
Figure 8A:
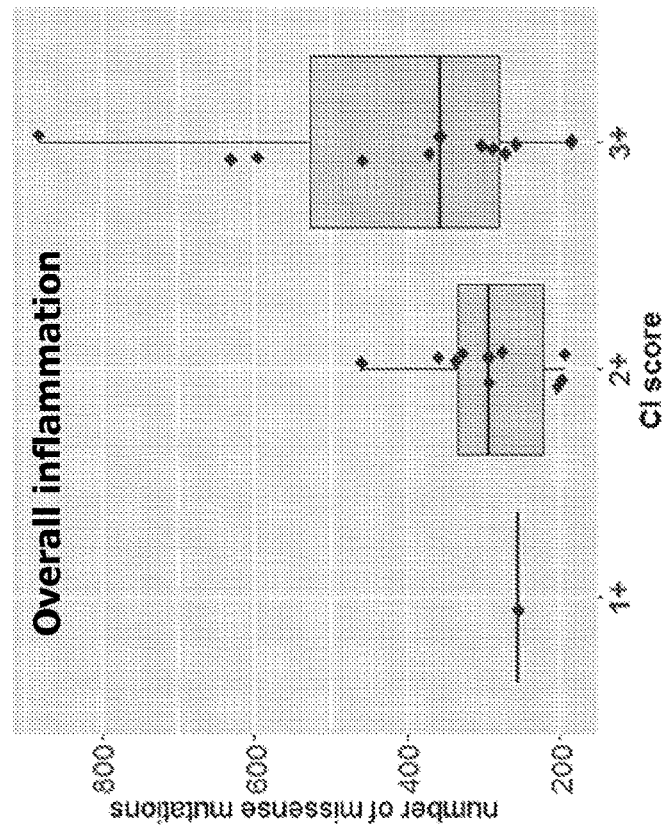

A higher mutational load has also been linked to inflamed tumors (FIG. 8). Panel A shows overall inflammation measured using a "CI Score" which is the intensity score of chronic inflammation infiltrate. Panel B shows PD-L1+ inflammation measured using a "PD-L1+CI Score" which is the intensity score of relative proportion of PD-L1+immune infiltrate. There is a relationship between the number of missense mutations in NSCLC tumors and overall inflammation.

Figures 9A, 9B:
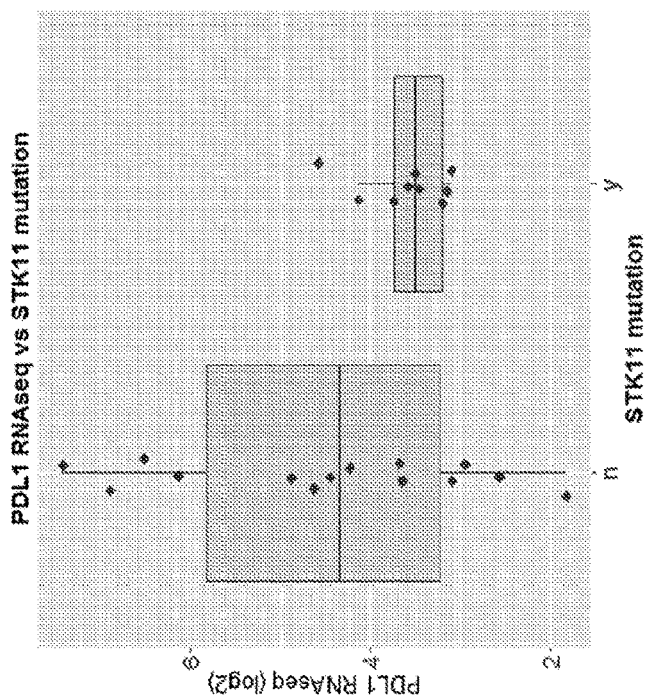
FIGS. 9A-9B show the frequency of mutations in different biomarkers (TP53, STK11, KEAP1, KRAS, EGFR, and MET) versus the observed PD-L1 expression pattern in FIG. 9A. D=diffuse, H=heterogeneous, I=tumor-stroma interface, N=negative.
Figure 11:
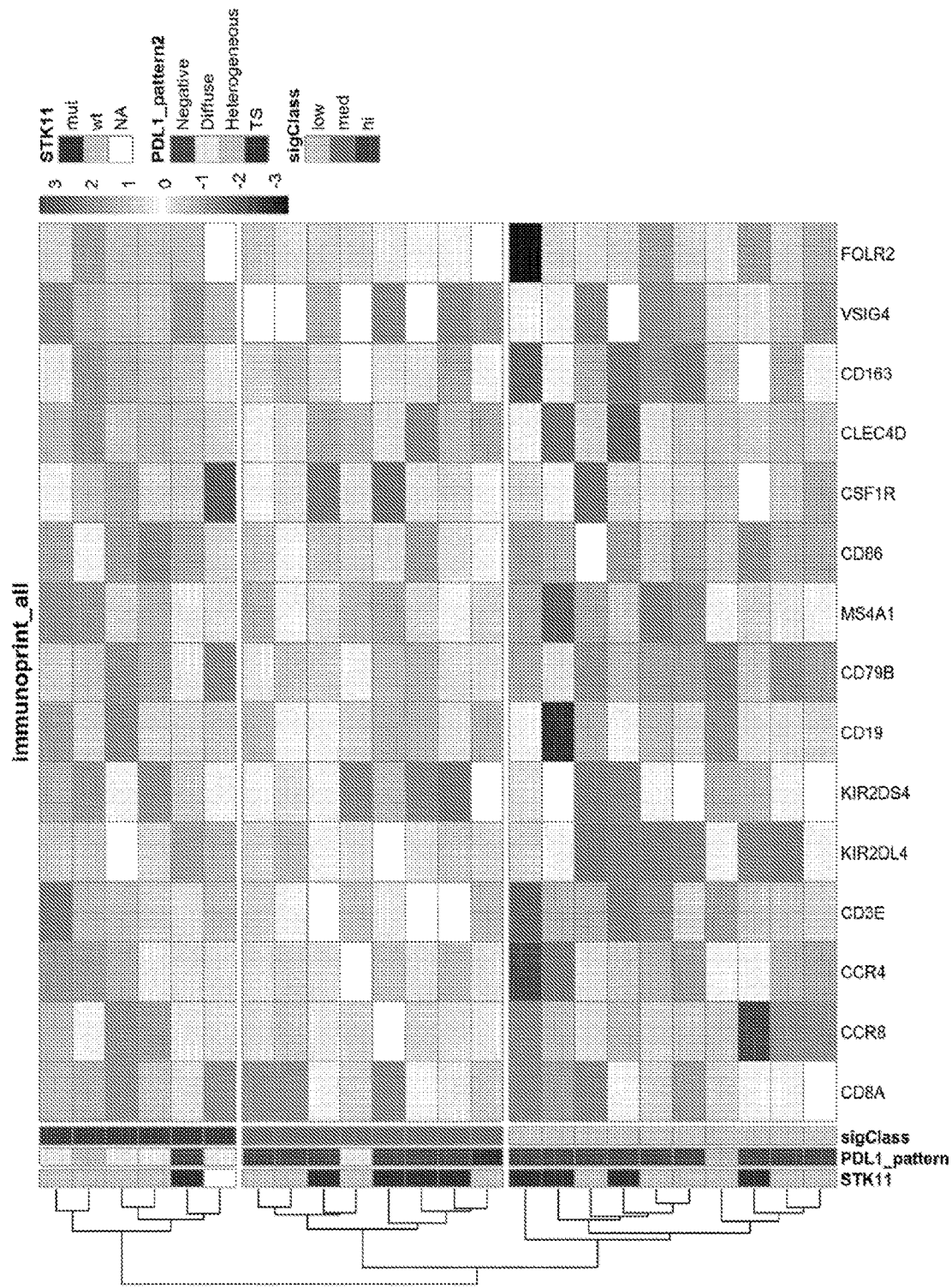
FIG. 11 shows an immunoprint analysis of 24 NSCLC tumor samples in which levels of FOLR2, VSIG4, CD163, CLEC4D, CSF1R, CD86, MS4A1, CD79B, CD19, KIR2DS4, CD3E, CCR4, CCR8, and CD8A were analyzed to classify the samples according to inflammation patterns (sigClass). Samples were classified as low ("sigClass low"), medium ("sigClass med") and high ("sigClass hi") inflammation. Samples were classified also according to presence ("STK11 mut") or absence ("STK11 wt") of STK11 mutations. In addition, samples were classified according to PD-L1 expression pattern as negative ("PDL1_pattern 2 Negative"), diffuse, ("PDL1_pattern 2 Diffuse"), heterogeneous ("PDL1_pattern 2 Heterogeneous"), and tumor-stroma interface ("PDL1_pattern 2 TS").

Frequency of mutations in different biomarkers (TP53, STK11, KEAP1, KRAS, EGFR, and MET) versus the observed PD-L1 expression pattern was evaluated (FIG. 9), the results indicating that negative PD-L1 tumor cell expression and lower PD-L1 mRNA expression are been associated with the presence of SKT11 mutation. The presence of mutant STK11 correlated with the presence of the "N" (PD-L1 negative) expression pattern. The presence of mutant STK11 did not correlate with the presence of the "D" (diffuse) pattern, which is the pattern observed in most responders to nivolumab therapy. Accordingly, the presence of mutant forms of STK11 could be used as negative biomarker for treatment of NSCLC tumors with nivolumab (i.e., its presence would predict lack of response or poor response to nivolumab). Conversely, the presence of wild type forms of STK11 (or absence of mutant forms) could be used as a positive selection biomarker for treatment with nivolumab.

STK11 loss due to mutation is predicted to increase mTOR signaling. Lung adenocarcinoma (both mouse model and human tumors) with KRAS and STK11 mutations show decreased expression of PD-L1 and diminished T-cell infiltrates. The proposed mechanism of immune suppression mediated by mutations in SKT11 would include a switch to glycolytic metabolism with increased lactate production, and a frequent co-mutation of KEP1 leading to an anti-inflammatory transcriptional program.

An immunoprint analysis of 24 NSCLC tumor samples in which levels of FOLR2, VSIG4, CD163, CLEC4D, CSF1R, CD86, MS4A1, CD79B, CD19, KIR2DS4, CD3E, CCR4, CCR8, and CD8A were analyzed was used to classify the samples according to inflammation patterns (sigClass). Samples were classified as low ("sigClass low"), medium ("sigClass med") and high ("sigClass hi") inflammation. Samples were classified also according to presence ("STK11 mut") or absence ("STK11 wt") of STK11 mutations (FIG. 10). In addition, samples were classified according to PD-L1 expression pattern as negative ("PDL1_pattern 2 Negative"), diffuse, ("PDL1_pattern 2 Diffuse"), heterogenous ("PDL1_pattern 2 Heterogeneous"), and tumor-stroma interface ("PDL1_pattern 2 TS"). Tumor with diffuse PD-L1 expression patterns were shown highly inflamed and presented the wild type form of STK11. PD-L1 negative tumors cluster in two groups: moderate inflammation and low inflammation. There was no clear distinction in level of inflammation of PD-L1 negative tumors by STK11 mutation status. All the tumors with mutant STK11 were also negative for PD-L1.

This data indicate that PD-L1 patterns of expression associate with unique phenotypic and genetic backgrounds. Diffuse PD-L1 expression correlates with an inflamed TME and higher mutational load. Furthermore, the presence of STK11 mutations identifies a subset of PD-L1 negative tumors. These findings establish the suitability of STK11 as a biomarker to identify a subset of PD-L1 negative tumors, and the possibility of integrating histopathologic and genomic data to identify features that define NSCLC subsets with varying likelihood of response to immunotherapy.

Example 2

An open-label, randomized phase 3 clinical trial was conducted to study the effects of first-line anti-PD-1 monoclonal antibody (Nivolumab) therapy in patients having PD-L1-positive NSCLC. Patients with untreated stage IV or recurrent NSCLC and a PD-L1 tumor-expression level of 1% or more to receive nivolumab (administered intravenously at a dose of 3 mg/kg of body weight once every 2 weeks) or platinum-based chemotherapy (administered once every 3 weeks) for up to six cycles.

In a post-hoc analysis, patient tumors cells analyzed for expression of PD-L1 and wild-type or mutated STK11, KRAS, CDKN2A, PTPND, CUBN, and/or HERC1. Patient survival was then tracked for twenty-five months.

Figure 12A:
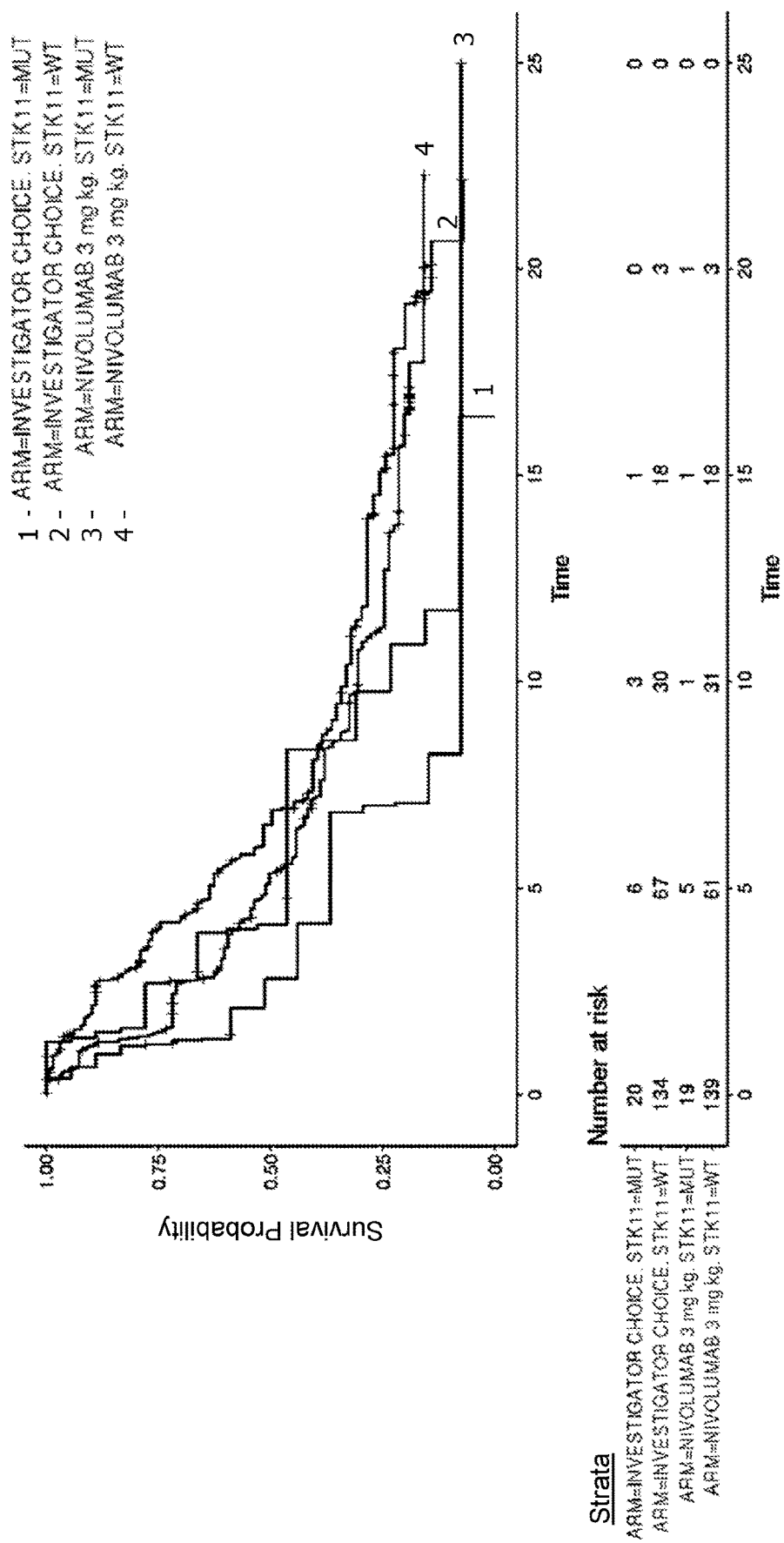
FIGS. 12A-12B are graphical representations of survival probability for advanced NSCLC subjects having wild type STK11 (data labels 2 and 4) or mutated STK11 (data labels 1 and 3) treated with investigator choice chemotherapy (data labels 1 and 2) or first-line 3 mg/kg anti-PD-1 antibody therapy (Nivolumab; data labels 3 and 4).
Figure 12B:
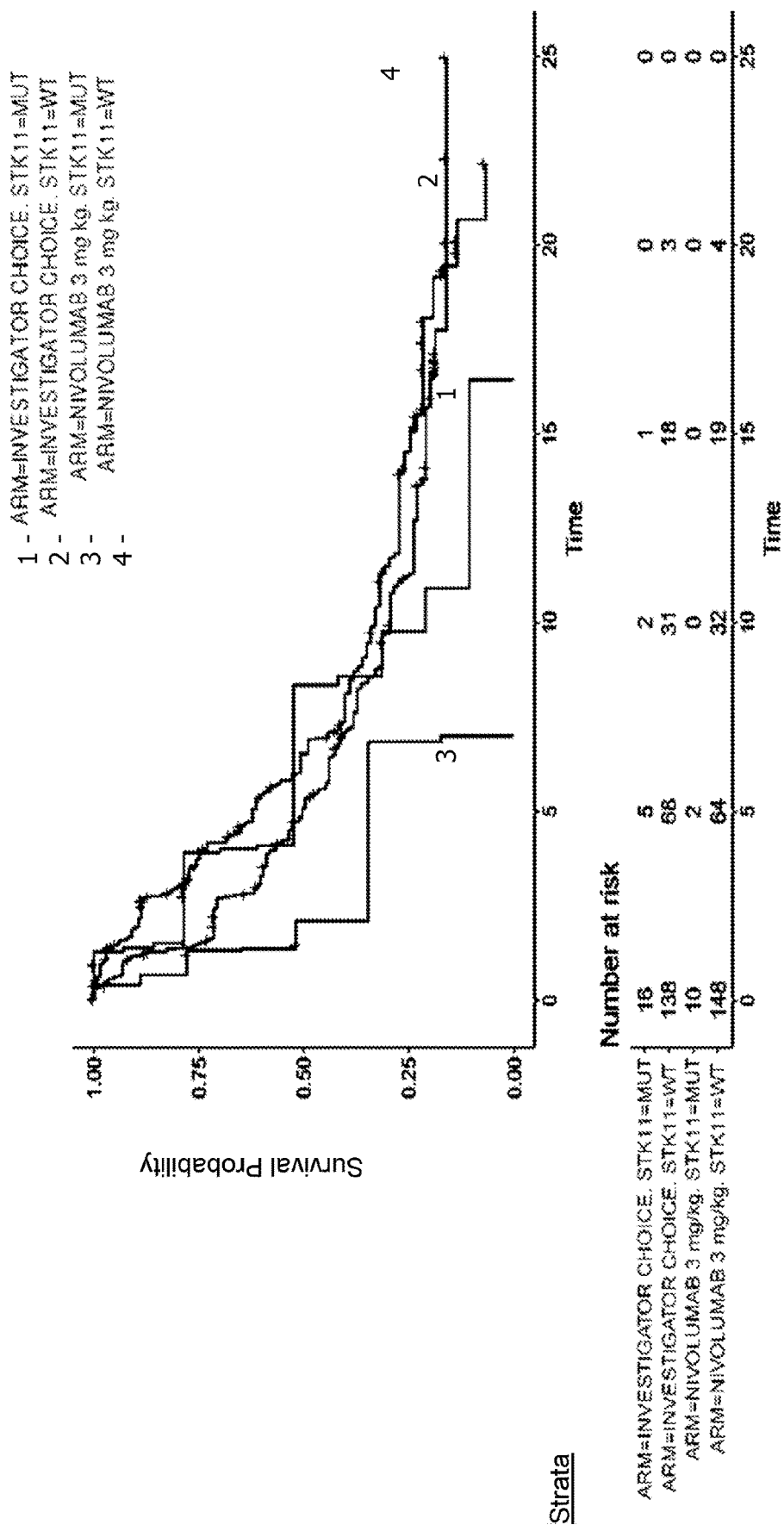
Figure 13:
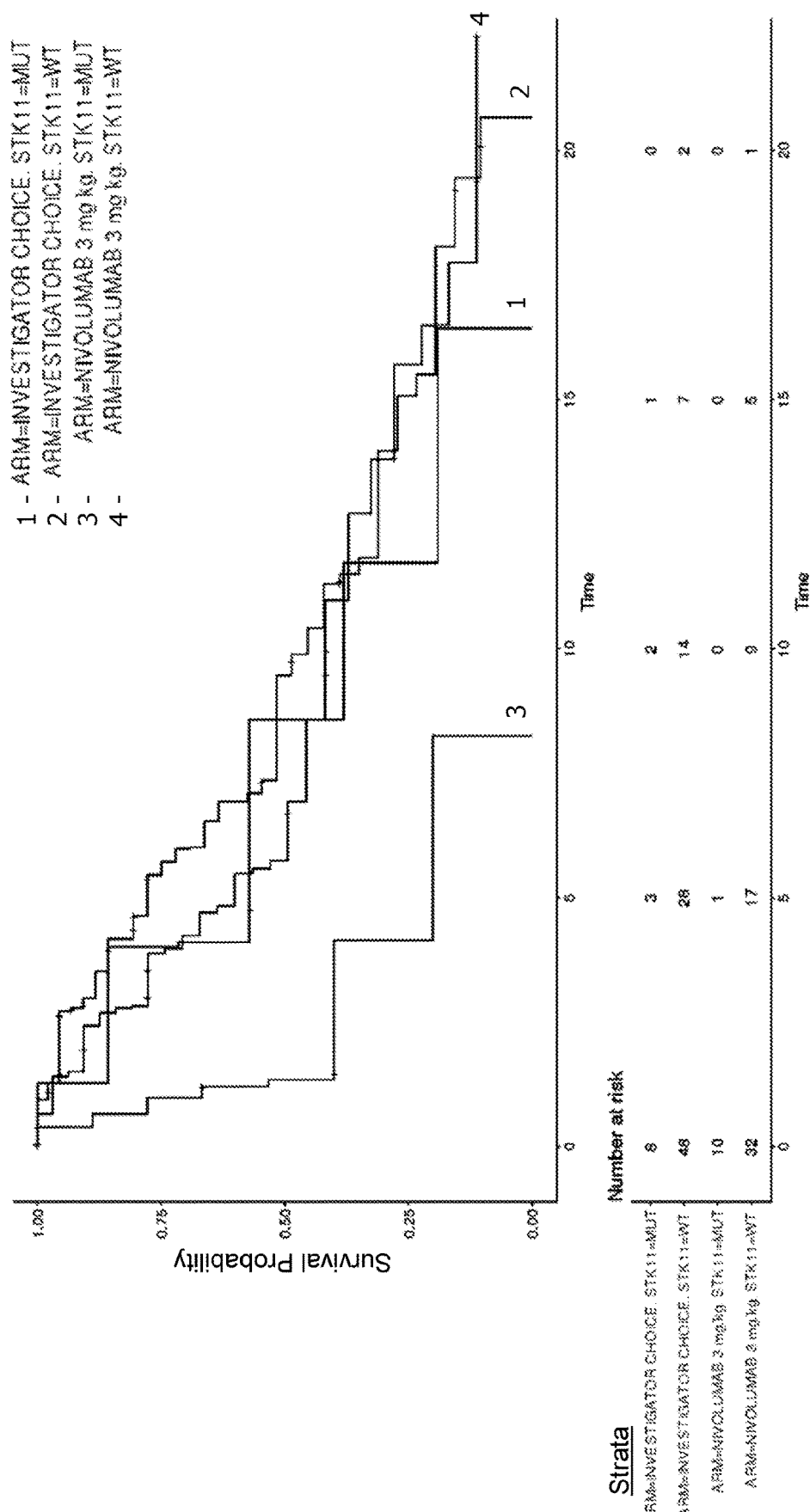
FIG. 13 is a graphical representation of survival probability for advanced NSCLC subjects having a KRAS mutation and either wild type STK11 (data labels 2 and 4) or mutated STK11 (data labels 1 and 3), wherein the subjects were treated with investigator choice chemotherapy (data labels 1 and 2) or first-line 3 mg/kg anti-PD-1 antibody therapy (Nivolumab; data labels 3 and 4). The numbers of subjects at risk at each time point for each group is shown below the X axis.
Figure 14A:
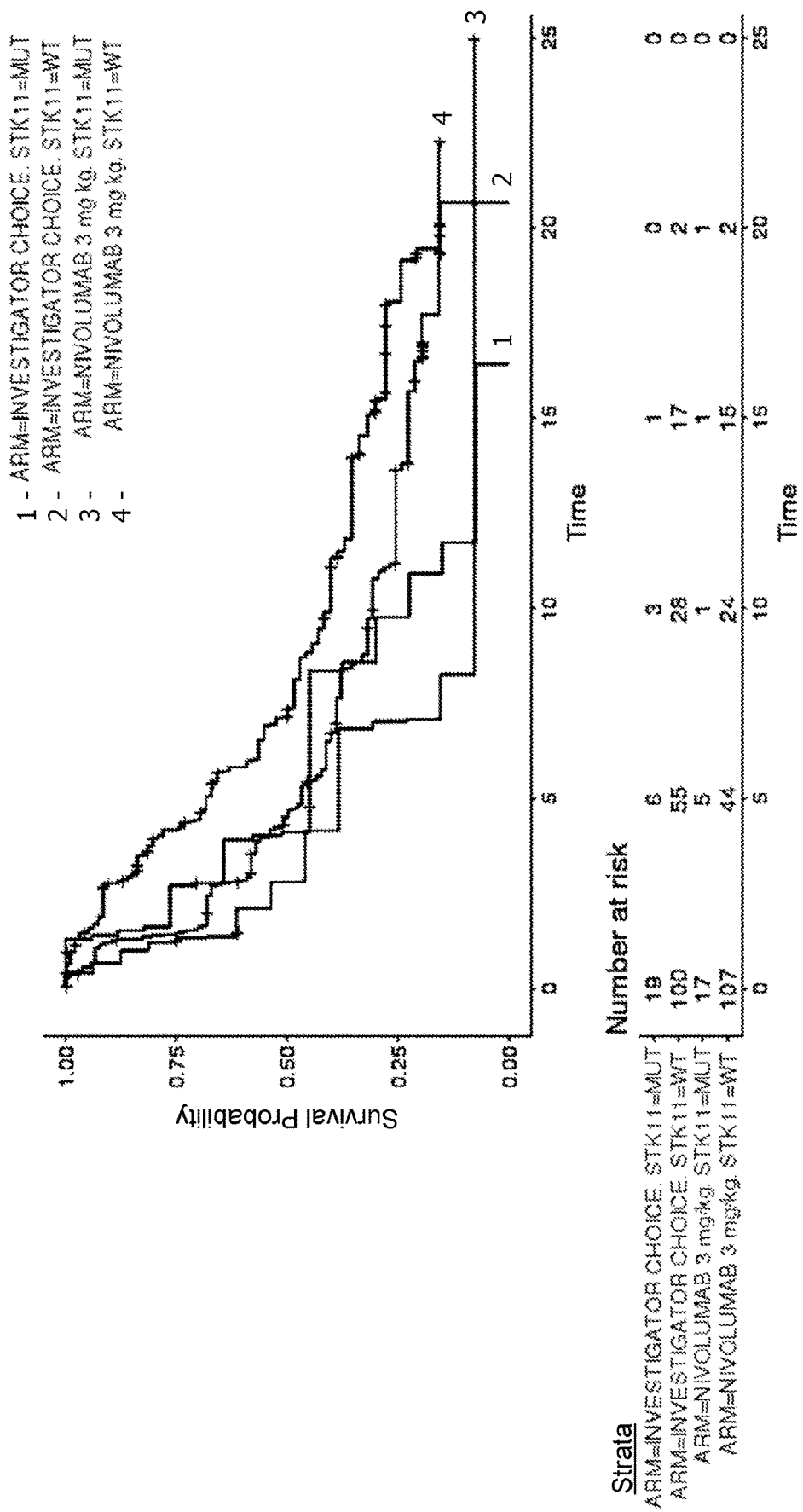
FIGS. 14A-14B are graphical representations of survival probability for non-squamous cell NSCLC subjects having wild type STK11 (data labels 2 and 4) or any non-synonymous mutation in STK11 (data labels 1 and 3) treated with investigator choice chemotherapy (data labels 1 and 2) or first-line 3 mg/kg anti-PD-1 antibody therapy (Nivolumab; data labels 3 and 4).
Figure 14B:
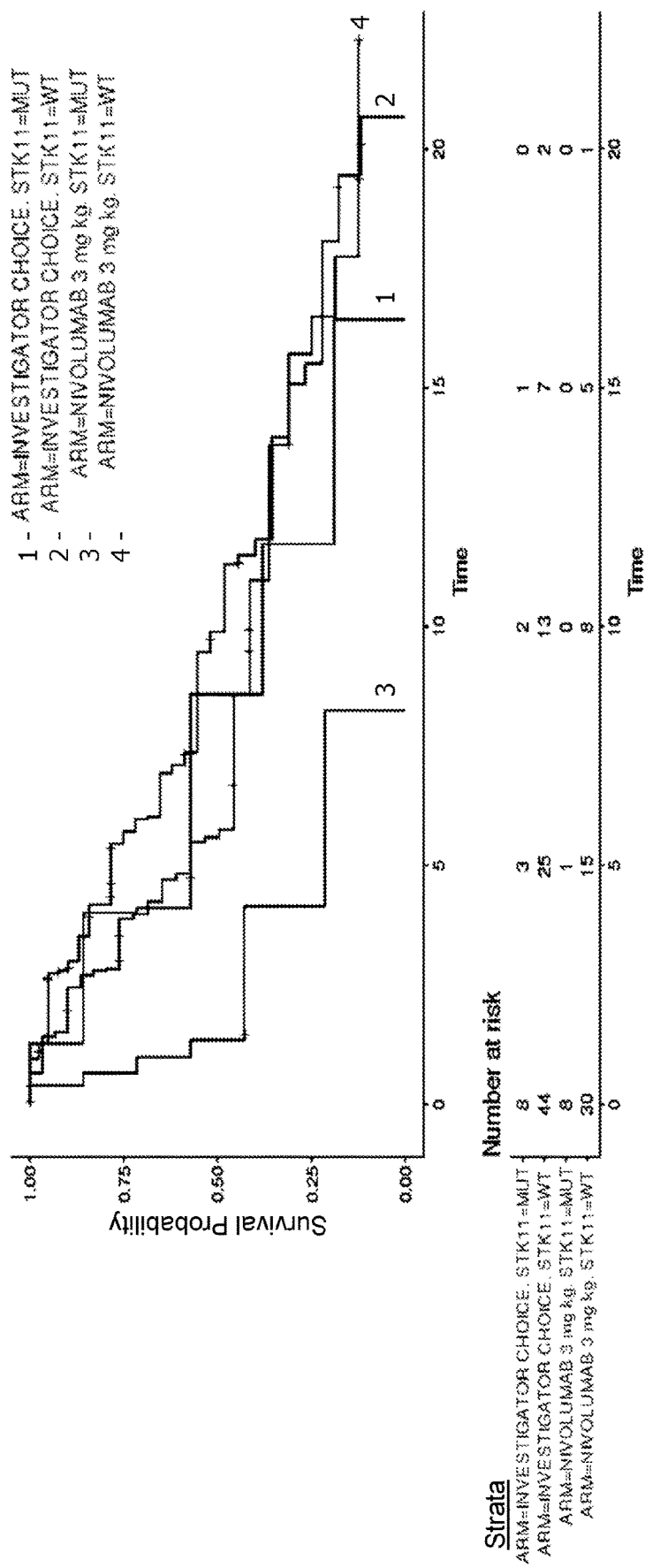

Following treatment, patients that carried a mutated variant of STK11 were found to have lower progressive free survival (PFS) than patients having wild-type STK11. This was observed in patients having any non-synonymous STK11 mutation (FIG. 12A) and in patients with a nonsense, frameshift, or splicing STK11 mutation (FIG. 12B). STK11 mutation carrying patients further having a KRAS mutation also showed less responsiveness to anti-PD-1 antibody therapy (FIG. 13). When patients were stratified based on type of NSCLC, patients having non-squamous cell NSCLC and any mutation in STK11 had a lower PFS than patients having wild-type STK11, regardless of KRAS status (FIG. 14A-14B).

Figure 15C:
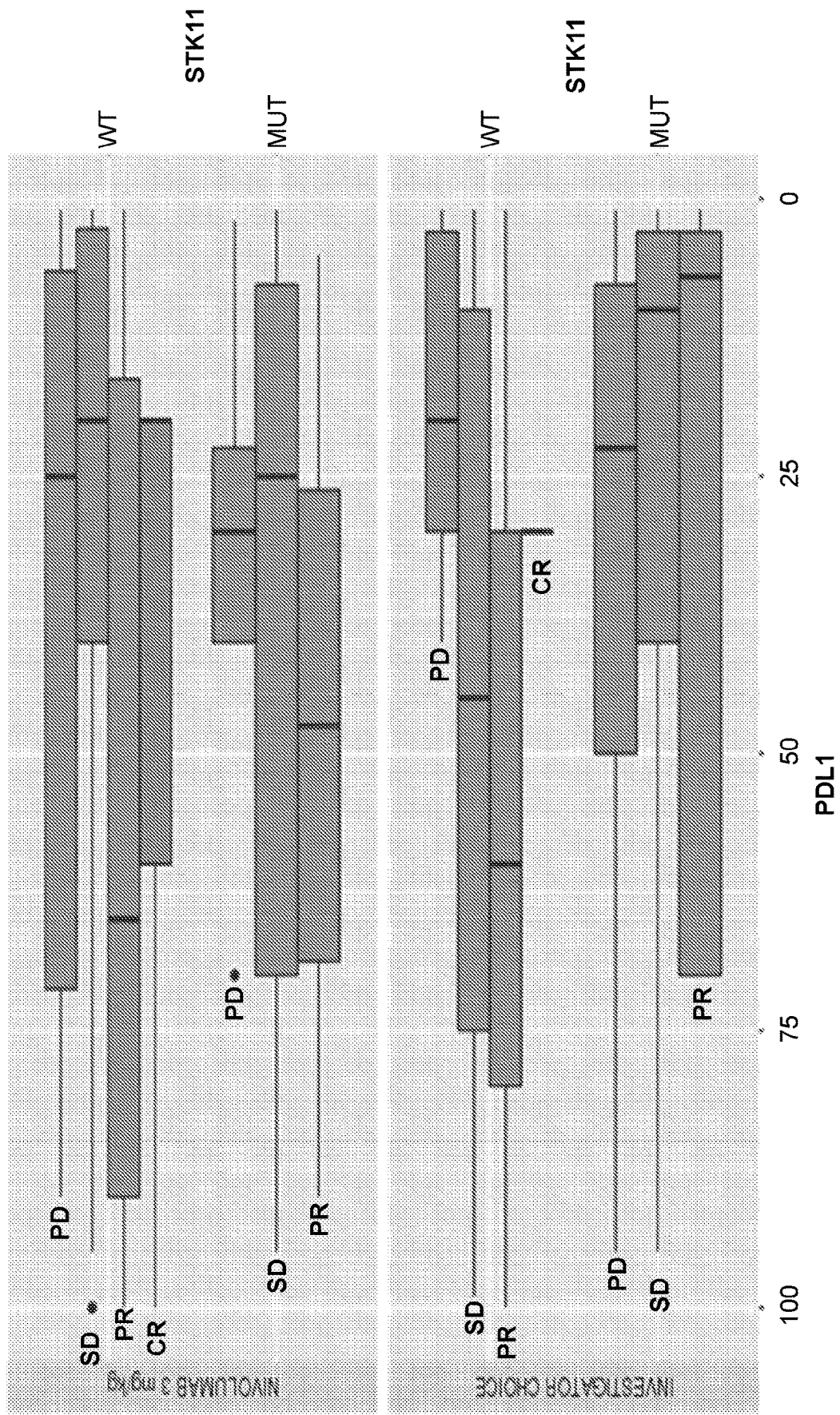

STK11 mutation status and responsiveness were compared to tumor PD-L1 expression levels (FIGS. 15A-15F). Two patients exhibiting partial responses following anti-PD-1 antibody therapy were found have STK11 mutations and high PD-L1 levels (FIG. 15B). However, in the anti-PD-1 antibody arm, PD-L1 expression levels were similar in the wild-type and STK11 mutant subgroups (FIG. 15E).

Figure 16A:
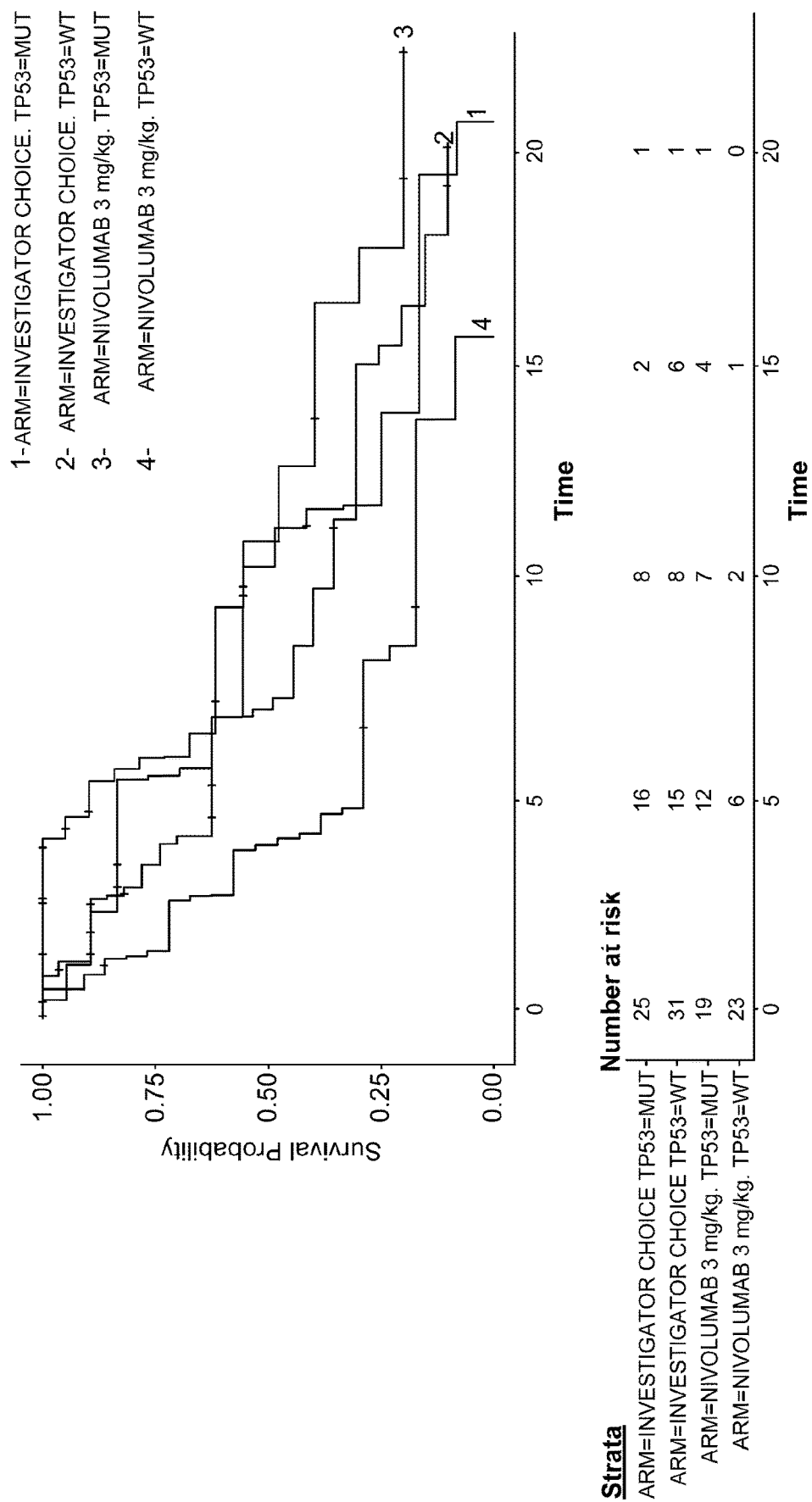
FIG. 16A is a graphical representation of survival probability for advanced NSCLC subjects having a KRAS mutation and either wild type TP53 (data labels 2 and 4) or mutated TP53 (data labels 1 and 3), wherein the subjects were treated with investigator choice chemotherapy (data labels 1 and 2) or first-line 3 mg/kg anti-PD-1 antibody therapy (Nivolumab; data labels 3 and 4).
Figure 16B:
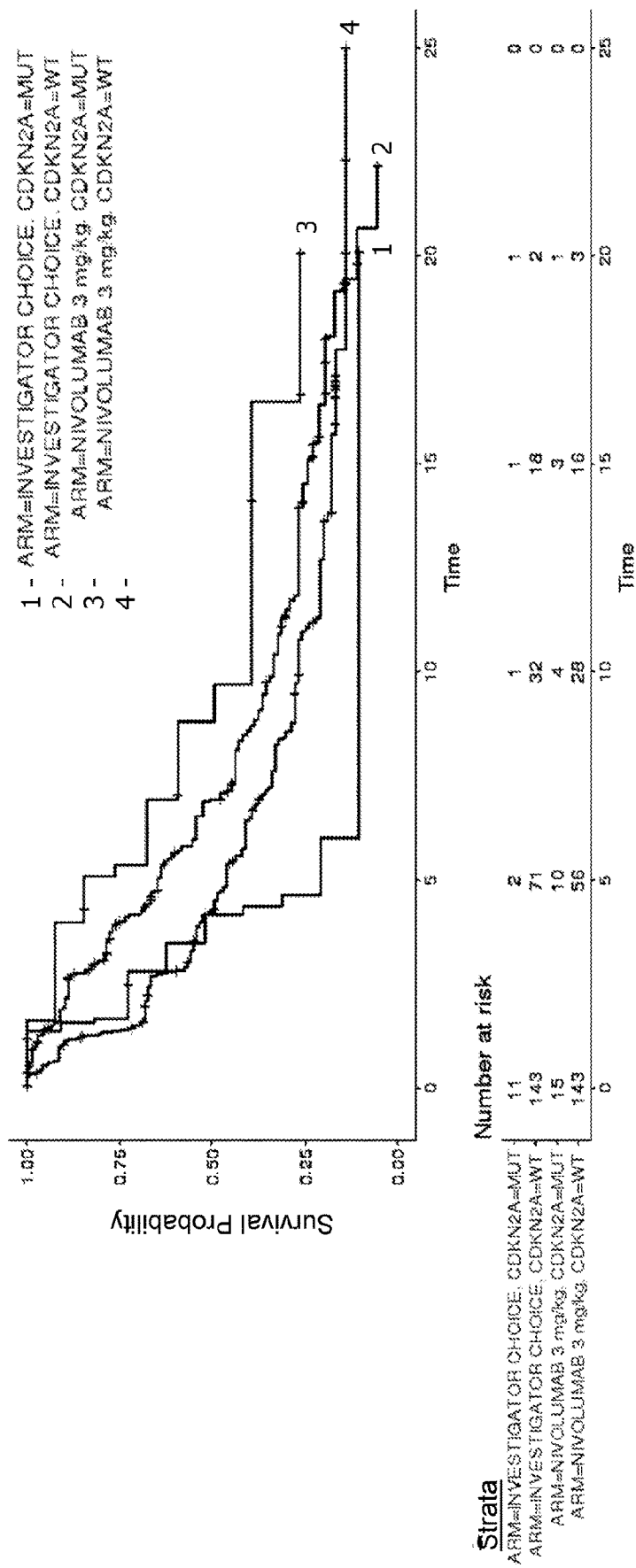
FIGS. 16B-16C are graphical representations of survival probability for advanced NSCLC subjects having wild type (data labels 2 and 4) or mutated (data labels 1 and 3) CDKN2A (FIG. 16B) or PTPND/CUBN/HERC1 (FIG. 16C) treated with investigator choice chemotherapy (data labels 1 and 2) or first-line 3 mg/kg anti-PD-1 antibody therapy (Nivolumab; data labels 3 and 4). The numbers of subjects at risk at each time point for each group is shown below the X axes (FIGS. 16A-16C).
Figure 16C:
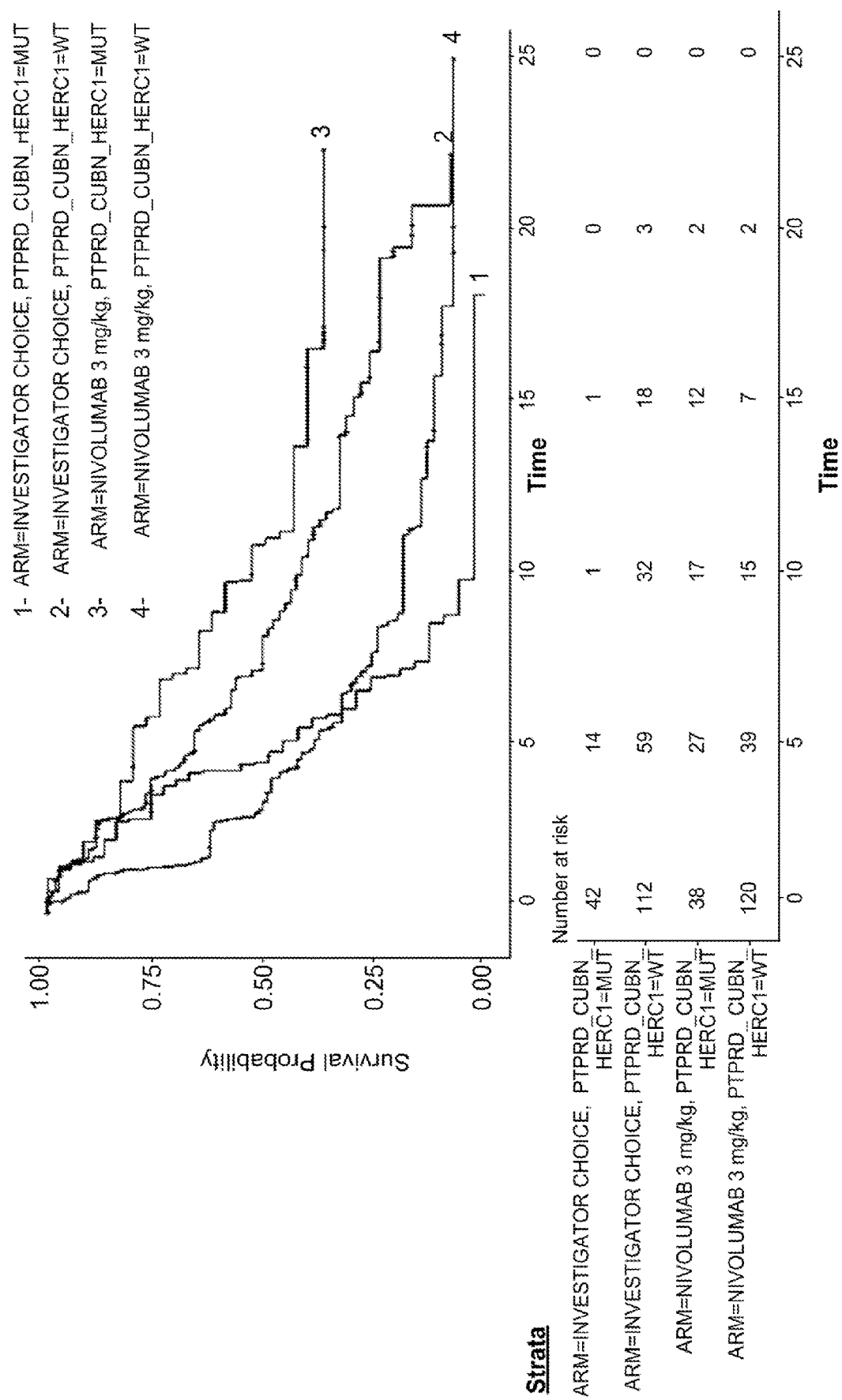
Figure 16D:
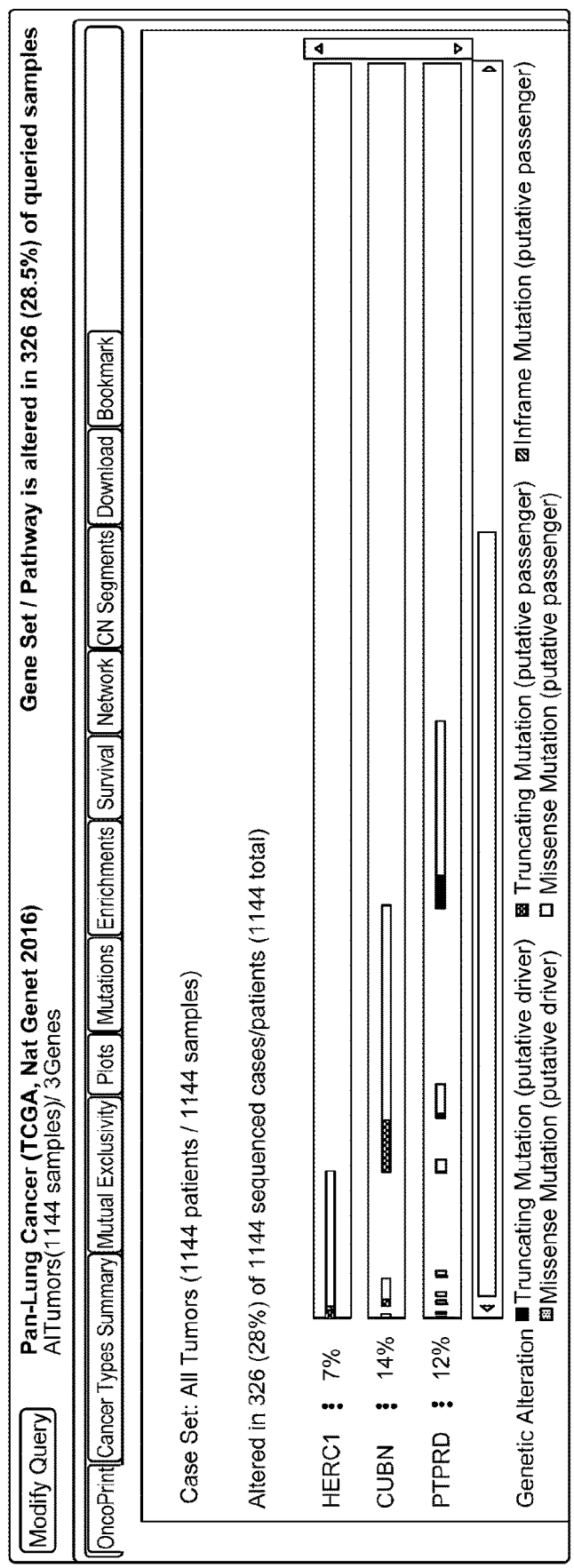
FIG. 16D is a screenshot showing the distribution of HERC1, CUBNM, and PTPRD mutations in the 1144 subjects analyzed.

In addition to STK11, patient tumors were monitored for TP53, CDKN2A, PTPND, CUBN, and HERC1 status (FIGS. 16A-16D). Patients having mutations in both TP53 and KRAS showed greater PFS than patients having wild-type TP53 following treatment with first-line anti-PD-1 monoclonal antibody therapy (FIG. 16A). Patients having a mutation in CDKN2A also showed a higher PFS than those having wild-type CDKN2A (FIG. 16B), and the same was true for patients having mutated variants of PTPND, CUBN, and HERC1 (FIG. 16C-16D).

Figure 17C:
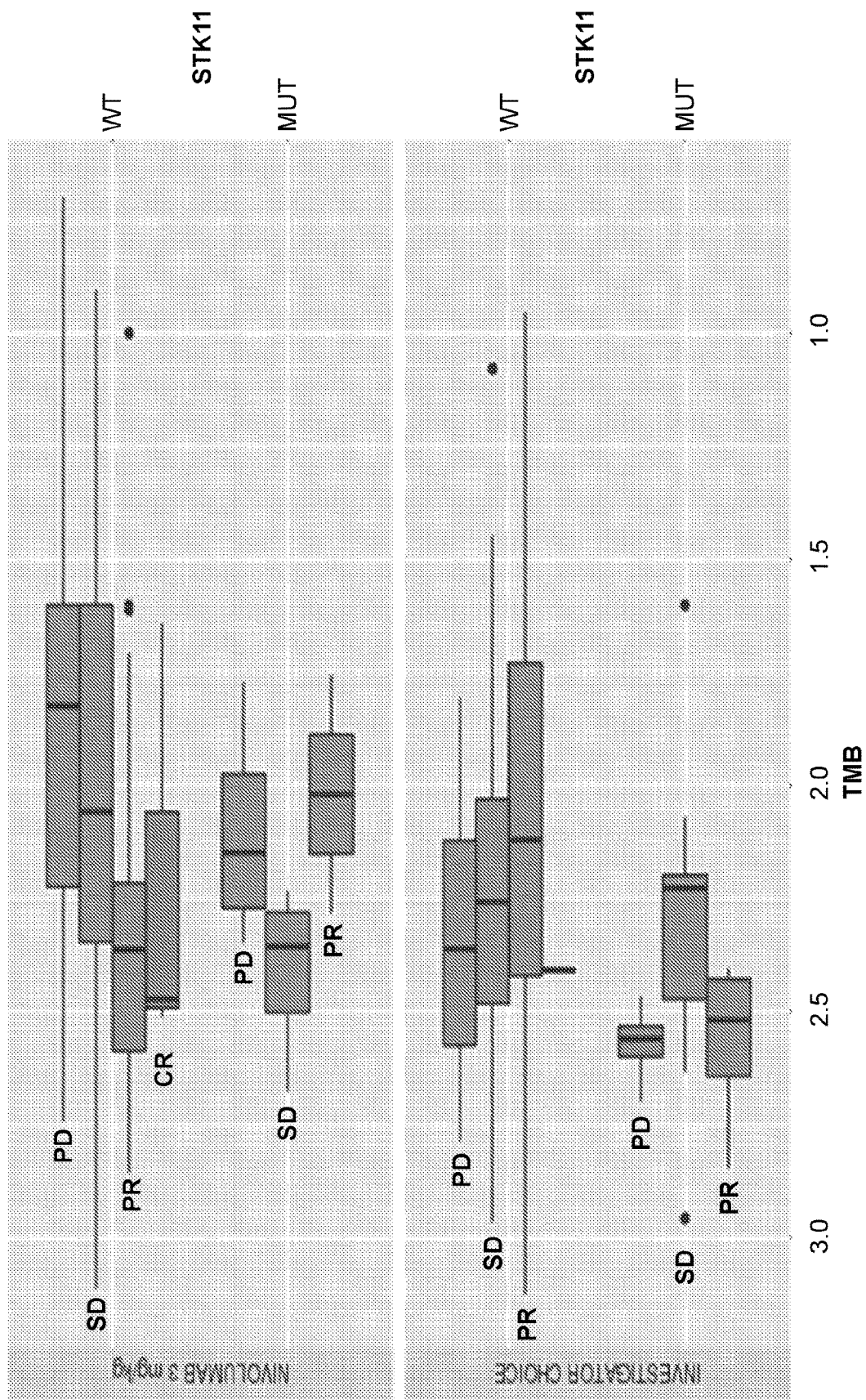
FIG. 17C is a graphical representation showing the distribution of WT or mutated STK11 subjects experiencing a complete response (CR), partial response (PR), stable disease (SD), or progressive disease (PD) following treatment with either an investigator choice chemotherapy or first-line 3 mg/kg anti-PD-1 antibody therapy (Nivolumab) as related to tumor mutational burden (TMB.

Overall, there was no apparent difference in TMB based on STK11 status for all patients or when focused only on those patients also having a KRAS mutation (FIGS. 17A-17B). However, there may have been a slight increase in overall response for patients having a higher TMB as compared to patients having a lower TMB in wild-type STK11 patients (FIG. 17C).

Example 3

An open-label, randomized phase 3 clinical trial was conducted to study the effects of second-line anti-PD-1 monoclonal antibody (Nivolumab) therapy in patients having non-squamous cell NSCLC who have progressed during or after platinum-based doublet chemotherapy. Patients were administered nivolumab (administered intravenously at a dose of 3 mg/kg of body weight once every 2 weeks) or docetaxel (administered at a dose of 75 mg/m$^2$ once every 3 weeks).

Figure 18A:
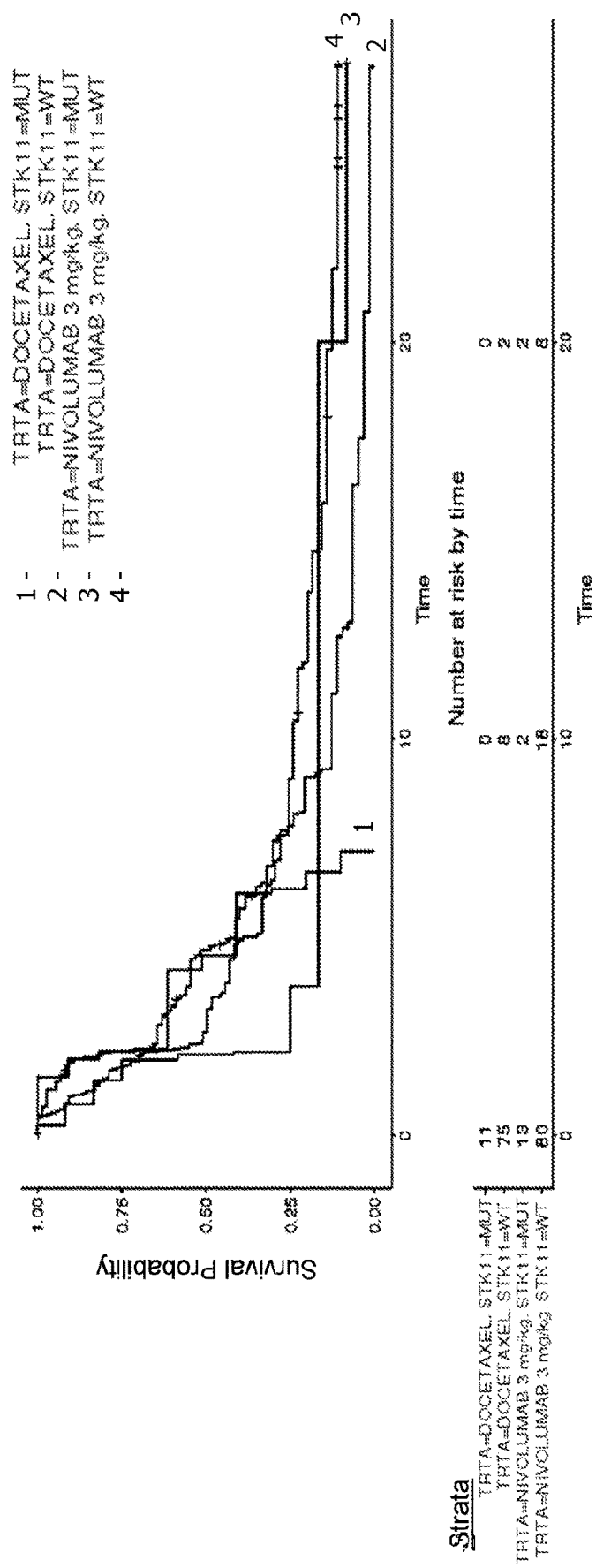
FIGS. 18A-18D are graphical representations of survival probability for non-squamous cell NSCLC subjects having wild type STK11 (data labels 2 and 4) or a mutation in STK11 (data labels 1 and 3) treated with docetaxel (data labels 1 and 2) or second-line 3 mg/kg anti-PD-1 antibody therapy (Nivolumab; data labels 3 and 4).
Figure 18B:
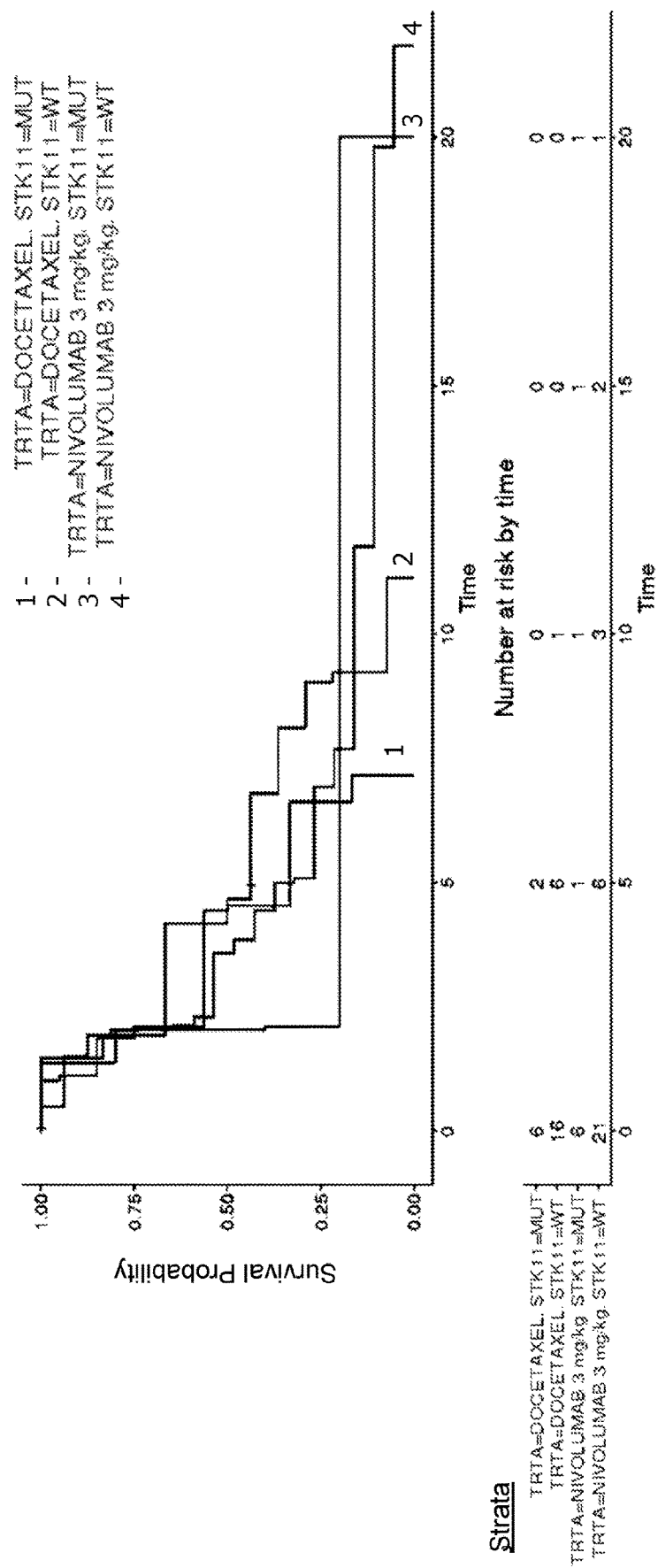
Figure 18C:
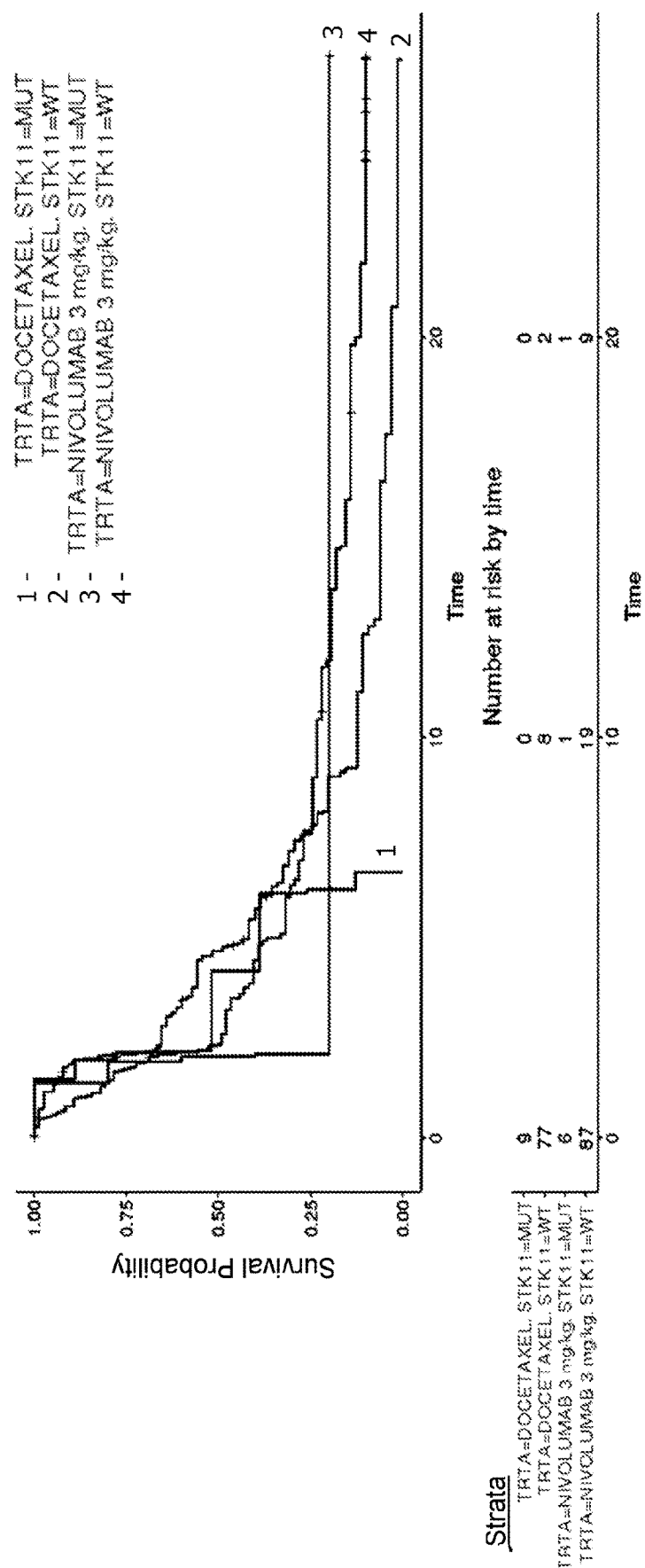
Figure 18D:
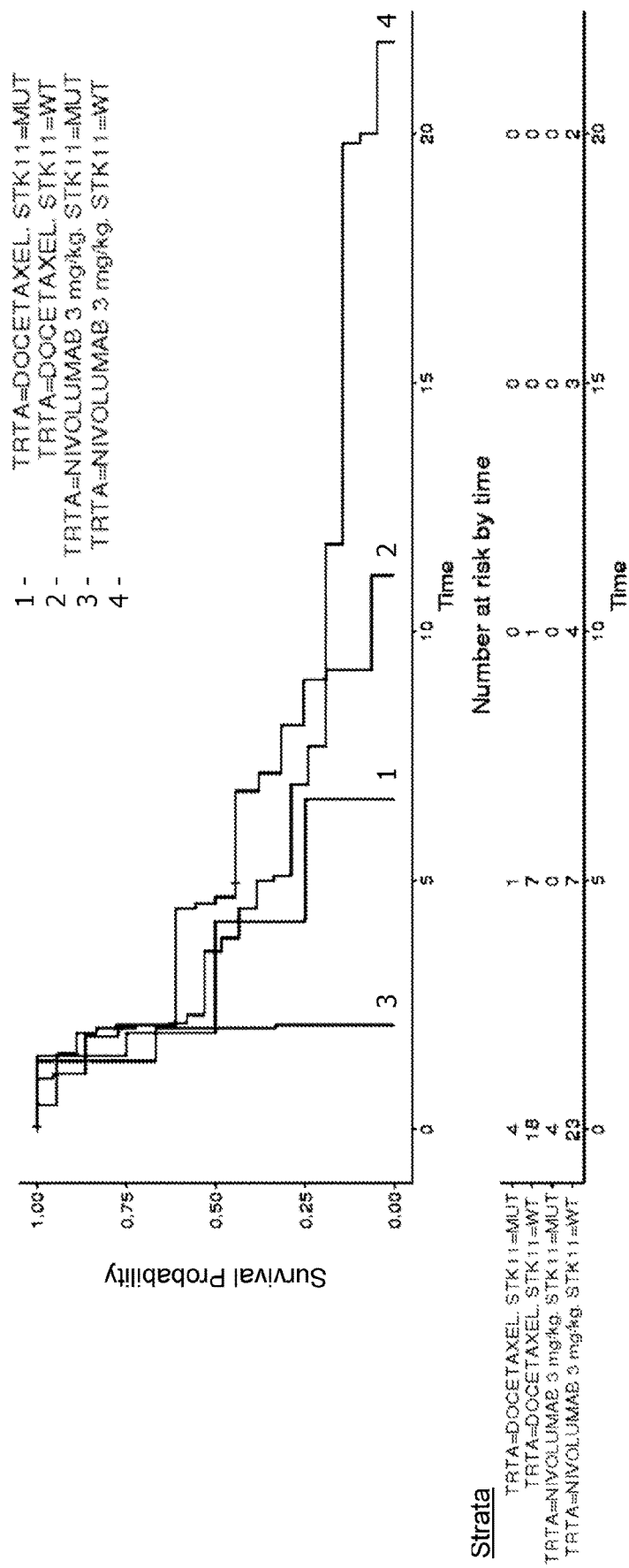

In a post-hoc analysis, patient tumors cells were analyzed for STK11 and KRAS mutation status. As observed in Example 2, above, patients having a mutant form of STK11 had generally lower overall PFS than patients having wild-type STK11 (FIGS. 18A-18D). This was the case whether the subject had any non-synonymous STK11 mutation (FIGS. 18A-18B) or a nonsense, frameshift, or splicing STK11 mutation (FIGS. 18C-18D), and whether the subject was wild-type for KRAS (FIGS. 18A and 18C) or had a mutant KRAS variant (FIG. 18B or 18D).

Example 4

An open-label, randomized phase 3 clinical trial was conducted to study the effects of second-line anti-PD-1 monoclonal antibody (Nivolumab) therapy in patients having squamous cell NSCLC who have progressed during or after platinum-based doublet chemotherapy. Patients were administered nivolumab (administered intravenously at a dose of 3 mg/kg of body weight once every 2 weeks) or docetaxel (administered at a dose of 75 mg/m$^2$ once every 3 weeks).

Figure 19:
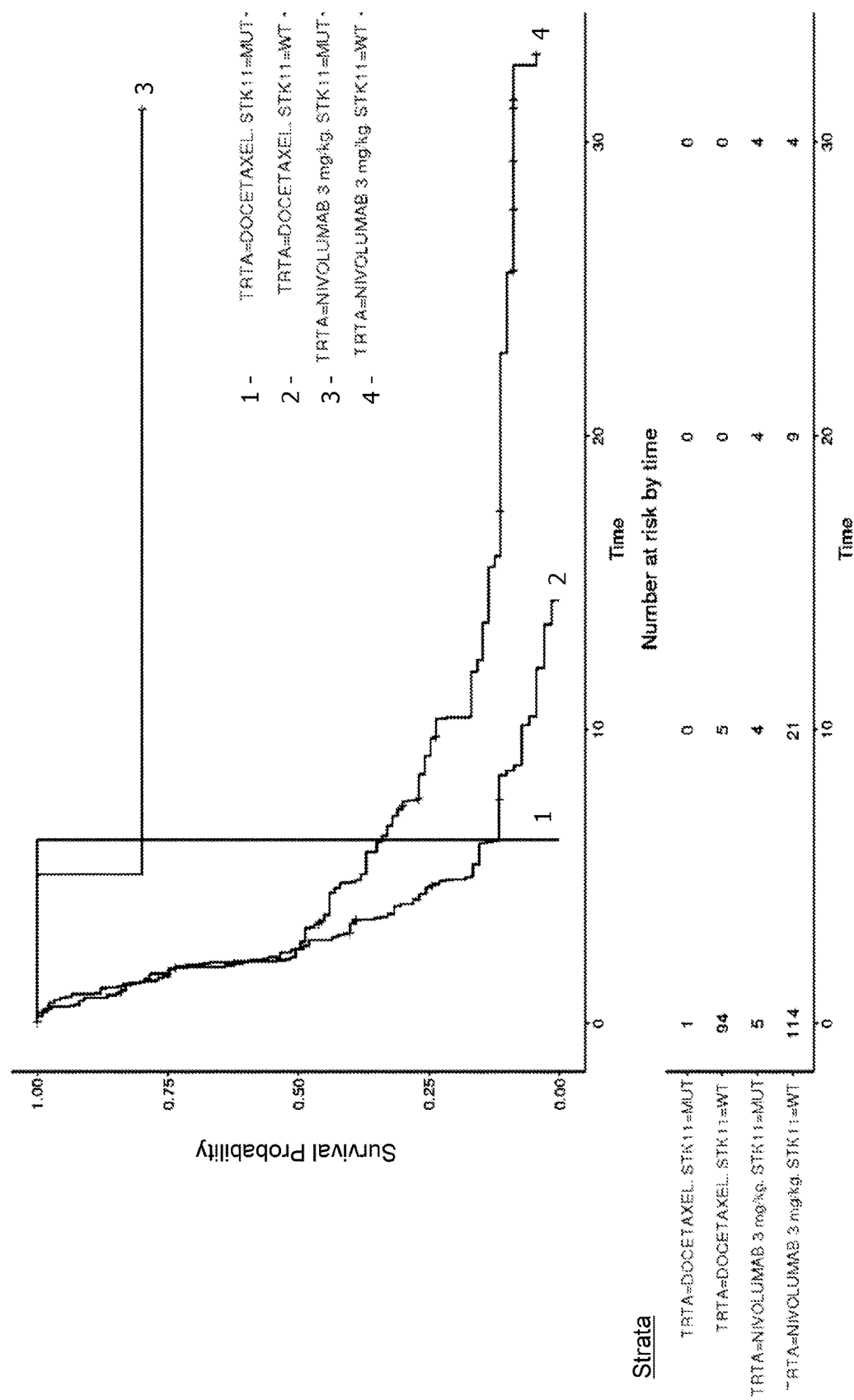
FIG. 19 is a graphical representation of survival probability for squamous cell NSCLC subjects having wild type STK11 (data labels 2 and 4) or a mutation in STK11 (data labels 1 and 3) treated with docetaxel (data labels 1 and 2) or second-line 3 mg/kg anti-PD-1 antibody therapy (Nivolumab; data labels 3 and 4). The numbers of subjects at risk at each time point for each group is shown below the X axis (FIG. 19).

In a post-hoc analysis, patient tumors cells were analyzed for STK11 mutation status. The occurrence of STK11 mutations in the patient population was low (n=5), patients having a mutant form of STK11 had higher overall PFS than patients having wild-type STK11 following treatment with an anti-PD-1 antibody (FIG. 19). Additional patients will be analyzed to confirm the value of these initial observations.

This application claims the benefit of U.S. Provisional Application No. 62/513,831 filed Jun. 1, 2017, which is incorporated by reference herein in its entirety.

What is claimed is:

1. A method of treating a subject afflicted with a tumor derived from a lung cancer comprising, (i) determining a mutation status of an STK11 gene in the subject; and (ii) administering to the subject an antibody or an antigen-binding portion thereof that binds specifically to a Programmed Death-1 (PD-1) receptor and inhibits PD-1 activity ("anti-PD-1 antibody"), wherein the subject is identified as having (i)_a wild-type STK11 gene and (ii) a mutated marker gene comprising PTPRD, CUBN, or a combination thereof; and wherein the tumor exhibits a diffuse membranous PD-L1 expression.

2. The method of claim 1, wherein the marker gene comprises a non-synonymous mutation, a nonsense, a frameshift, or a splicing mutation.

3. The method of claim 1, further comprising detecting PD-L1 expression in the tumor prior to the administration of the anti-PD-1 antibody.

4. The method of claim 1, wherein the tumor has a tumor mutational burden (TMB) status that is a high TMB.

5. The method of claim 4, wherein the tumor TMB status is determined by sequencing nucleic acids in the tumor and identifying a genomic alteration in the sequenced nucleic acids, wherein the genomic alteration comprises one or more alterations comprising a somatic mutation, a non-synonymous mutation, a missense mutation, a base pair substitution, a base pair insertion, a base pair deletion, a copy number alteration (CNAs), a gene rearrangement, or any combination thereof.

6. The method of claim 1, wherein the tumor exhibits high inflammation.

7. The method of claim 1, wherein the anti-PD-1 antibody comprises nivolumab, pembrolizumab, PDR001, MEDI-0680, cemiplimab, JS001, BGB-A317, INCSHR1210, TSR-042, GLS-010, AM-0001, STI-1110, AGEN2034, MGA012, or IBI308.

8. The method of claim 1, wherein the anti-PD-1 antibody is administered at a dose ranging from at least about 0.1 mg/kg to at least about 10.0 mg/kg body weight once about every 1, 2, or 3 weeks.

9. The method of claim 1, wherein the anti-PD-1 antibody is administered at a flat dose of about 240 mg or about 480 mg about once every 1, 2, 3, or 4 weeks.

10. The method of claim 1, wherein the anti-PD-1 antibody comprises nivolumab.

11. The method of claim 10, wherein the anti-PD-1 antibody is administered at a flat dose of about 240 mg once about every 2 weeks.

12. The method of claim 10, wherein the anti-PD-1 antibody is administered at a flat dose of about 360 mg once about every 3 weeks.

13. The method of claim 10, wherein the anti-PD-1 antibody is administered at a flat dose of about 480 mg once about every 4 weeks.

14. The method of claim 1, wherein the anti-PD-1 antibody comprises pembrolizumab.

15. The method of claim 14, wherein the anti-PD-1 antibody is administered at a flat dose of about 200 mg once about every 3 weeks.

16. The method of claim 1, wherein the tumor is recurrent.

17. The method of claim 1, wherein the subject has progressed during or after prior platinum-based doublet chemotherapy.

18. The method of claim 1, wherein the tumor is previously untreated.

19. The method of claim 1, wherein the tumor is a stage IV NSCLC.

20. The method of claim 1, wherein the subject is further identified as having a mutated marker gene comprising KRAS, TP53, CDKN2A, HERC1, or any combination thereof.

* * * * *